(12) United States Patent
Reinitz et al.

(10) Patent No.: US 7,260,544 B1
(45) Date of Patent: Aug. 21, 2007

(54) SYSTEM AND METHODS FOR EVALUATING THE APPEARANCE OF A GEMSTONE

(75) Inventors: Ilene M. Reinitz, New York, NY (US); Mary L. Johnson, San Diego, CA (US); James E. Shigley, Temecula, CA (US); Thomas S. Hemphill, Lexington, MA (US)

(73) Assignee: Gemological Institute of America, Inc., Carlsbad, CA (US)

( * ) Notice: Subject to any disclaimer, the term of this patent is extended or adjusted under 35 U.S.C. 154(b) by 1367 days.

(21) Appl. No.: 09/687,759

(22) Filed: Oct. 12, 2000

(51) Int. Cl.
B44B 5/00 (2006.01)
G01N 21/00 (2006.01)

(52) U.S. Cl. ............... 705/1; 702/35; 356/30; 356/425; 356/31; 356/303; 364/525; 364/507

(58) Field of Classification Search ............ 705/1; 702/35; 364/507; 356/30, 31
See application file for complete search history.

(56) References Cited

U.S. PATENT DOCUMENTS

| | | | |
|---|---|---|---|
| 3,947,120 A | 3/1976 | Bar-Issac et al. | 356/30 |
| 4,266,871 A | 5/1981 | Ritzi | 356/30 |
| 5,615,005 A * | 3/1997 | Valente et al. | 356/30 |
| 5,966,673 A * | 10/1999 | Shannon, Sr. | 702/35 |

FOREIGN PATENT DOCUMENTS

| | | |
|---|---|---|
| DE | 3600115 A1 | 7/1987 |
| IL | 43465 | 12/1976 |
| JP | 57-204440 | 12/1982 |
| JP | 58-728 | 1/1983 |
| JP | 58-38843 | 3/1983 |
| JP | 58-92920 | 6/1983 |
| JP | 5-79993 | 3/1993 |
| JP | 7-333158 | 12/1995 |
| JP | 9-273994 | 10/1997 |
| JP | 11-255511 | 9/1999 |

OTHER PUBLICATIONS

U.S. Appl. No. 09/505,981, filed Feb. 16, 2000, Dejong, Peter et al.

(Continued)

Primary Examiner—James P. Trammell
Assistant Examiner—Daniel L. Greene

(57) ABSTRACT

Of the "four C's," cut has historically been the most complex to understand and assess. This application presents a three-dimensional mathematical model to study the interaction of light with a fully faceted, colorless, symmetrical round-brilliant-cut diamond. With this model, one can analyze how various appearance factors (brilliance, fire, and scintillation) depend on proportions. The model generates images and a numerical measurement of the optical efficiency of the round brilliant—called DCLR—which approximates overall fire. DCLR values change with variations in cut proportions, in particular crown angle, pavilion angle, table size, star facet length, culet size, and lower girdle facet length. The invention describes many combinations of proportions with equal or higher DCLR than "Ideal" cuts, and these DCLR ratings may be balanced with other factors such as brilliance and scintillation to provide a cut grade for an existing diamond or a cut analysis for prospective cut of diamond rough.

8 Claims, 53 Drawing Sheets

OTHER PUBLICATIONS

U.S. Appl. No. 09/687,659, filed Oct. 12, 2000, Reinitz, Dr. Illene et al.

Hemphill T.S., Reinitz I.M., Johnson M.L., Shigley J.E. (Fall 1998) Modeling the appearance of the round brilliant cut diamond: An analysis of brilliance. Gems & Gemology, vol. 34, No. 3, pp. 158-183.

Manson D.V. (1991) Proportion considerations in round brilliant diamonds (abstract), A.S. Keller, Ed., *Facing the Future—Proceedings of the International Gemological Symposium*, Jun. 20-24, 1991, Los Angeles, p. 60.

Suzuki S. (1970) A new design for brilliance plus dispersion. *Australian Gemmologist*, vol. 10, No. 10, pp. 13-24.

Harding B.L. (1975) Faceting limits. Gems & Gemology, vol. 15, No. 3, pp. 78-87.

Dodson J.S. (1978) A statistical assessment of brilliance and fire for polishing gem diamond on the basis of beometrical optics. Ph.D. Thesis, University of London.

Dodson J.S. (1979) The statistical brilliance, sparkliness and fire of the round brilliant-cut diamond. *Diamond Research*, 1979, pp. 13-17.

Tognoni C. (1990) An automatic procedure for computing the optimum cut proportions of gems. *La Gemmologia*, vol. 15, No. 3-4, pp. 23-32.

Kato M. (1982) Re-Examination of Optimum Cutting Angles Between Main Facets of Gemostones Based on Geometrical Optics. *Journal of the Gemmological Society of Japan*, vol. 9, No. 1, 3-17, pp. 127-142.

Kato M. (1991) Evaluation of brilliancy in relation to various combinations of the main facet angles. *Journal of the Gemmological Society of Japan*, vol. 16, No. 1-2, pp. 15-23 (and English translation).

Astric B., Merigoux H., Zecchini P. (1991) Etude theorique de l'aspect d'un diamant taille brilliant en fonction de ses parametres de taille. *Revue de Gemmologie a.f.g.*, No. 107, pp. 17-23 (and English translation).

Astric B., Merigoux H., Zecchini P. (1992) Etude de la vaariation de l'aspect de pierres taillees a l'aide d'image de synthese. *La Gemmologia*, vol. 17, No. 1, pp. 7-31 (and English translation).

Internet (http://www.rockhounds.com/rockshop/gem_designs/gemcad.html) GemCad, a computer program for modeling the appearance of faceted gemstones that has been available for several years (Product Review: GemCad 4.0: Rowland J., Originally Published in the Garnet Gazette Mar. 1994).

Internet (http://www.gemology.ru:8101/octonus) Octonus, a company at Moscow State University formed in 1991, that is involved with conducting research on the computer modeling of diamond appearance. The company sells a commercial computer program for light tracing in polished diamonds. They also present results of their research work on diamond appearance on this web site. Inventor first met representative of this group in Jun. 1999.

Internet (http://www.thunder.prohosting.com/~ultratec/ray.html) GEMRAY, Davis Designs, Strickland R. (last updated Aug. 8, 1999).

Walters G. (Dec. 1996) Cut Grading: Do the Numbers Add Up? Rapaport Diamond Report, vol. 19, No. 45, pp. 49-50.

Gilbertson A., Walters G. (Jan. 1997) What Tolkowsky Really Said. Rapaport Diamond Report, vol. 20, No. 2, pp. 35-37.

Gilbertson A., Walters G. (Feb. 1997) The Measure of Beauty, Rapaport Diamond Report, vol. 20, No. 6, pp. 43-46.

Gilbertson A. (Fall 1999) The Revolution in Cut Grading, Gems & Gemology, p. 157.

Gilbertson A., Walters G., Mcleod K., Wildman M. (1998), Letting Light Speak for Itself, Advancements in the Science of Cut Analysis, Diamond Profile Laboratory.

Lakowski R. (Jul. 1977) C24 Diamond Colour Grading: A Comparative Evaluation, Color 77, Invited Lectures and Extended Abstracts of the Papers to be Presented at the Third Congress of the International Colour Association, Rensselaer Polytechnic Institute, Troy, New York, pp. 473-477.

Dodson J.S. (Apr. 1978) A Statistical Assessment of Brilliance and Fire for the Round Brilliant Cut Diamon, Optica Acta, vol. 25, No. 8, pp. 681-692.

Dodson J.S. (Apr. 1978) The Brilliance, Sparkliness And Fire Of Some Modifications To The Round Brilliant Cut Diamond Style, Optica Acta, vol. 25, No. 8, pp. 693-699.

Dodson J.S. (Apr. 1978) The Brilliance, Sparkliness And Fire Of Several Diamond Simulants, Optica Acta, vol. 25, No. 8, pp. 701-705.

Stern N. (1975) Computer Ray Tracing in Faceted Gemstones. Master of Science Thesis, Feinberg Graduate School of The Weizmann Institute of Science.

Kirkpatrick D. G., Walsh J. P. (Jun. 1985) The Geometry of Beam Tracing, ACM Proceedings of The Symposium on Computer Geometry, pp. 55-61.

Hanrahan R. (May 1986) Using Caching and Breadth-First Search to Speed Up Ray-Tracing (extended abstract), Proceeding of Graphics Interface' 86 and Vision Interface' 86, pp. 56-61.

Ghazanfarpour D. (Feb. 1992) Visualisation Realiste Par Lancer De Pyramides et Subdivision Adaptive, Proceedings of the 11th International Conference of the CADCAM, Computer Graphics and Computer Aided Technologies, pp. 167-180 (and English translation).

Devillers O. (Sep. 1989) Tool to Study the Efficiency of Space Subdivision Structures for Ray Tracing, pp. 467-481.

Getto P. (1989) Fast Ray Tracing of Unevaluated Constructive Solid Geometry Models, Proceedings of GC International' 89, Sringer-Verlag, pp. 563-578..

Glassner A. S. (Oct. 1984) Space Subdivision for Fast Ray Tracing, IEEE Journal of Computer Graphics and Applications, vol. 4, No. 10, pp. 15-22.

Heckbert P.S., Hanrahan P. (Jul. 1984) Beam Tracing Polygonal Objects, Computer Graphics—Proceedings of 1984 SIGGRAPH, vol. 18, No. 3, pp. 119-127.

Ohta M., Mackawa M. (1990) Ray-Bound Tracing for Perfect and Efficient Anti-Aliasing, The Visual Computer, International Journal of Computer Graphics, vol. 6, No. 3, pp. 125-133.

Picott K. P. (Mar. 1992) Extension of the Linear and Area Lighting Models, The IEEE Journal of Computer Graphics and Applications, vol. 12, No. 2, pp. 31-38.

Musgrave F. K. (Sep. 1987) A Realistic Model of Refraction for Computer Graphics, Master of Science in Computer and Information Sciences Thesis, UCSC-CRL-88-11.

Arvo J., Kirk D. (Jul. 1987) Fast Ray Tracing by Ray Classification, Computer Graphics—Proceedings of 1987 SIGGRAPH, vol. 21, No. 4, pp. 55-64.

Shoaff W., Recursive Ray Tracing, Jan. 12, 2000, http://www.cs.fit.edu/wds/classes/adv-graphics/raytrace/raytrace.html.

Yuan Y., Kunii T. L., Inamoto N., Sun L. (1988) GemstoneFire: Adaptive Dispersive Ray Tracing of Polyhedrons, The Visual Computer, International Journal of Computer Graphics, vol. 4, No. 5, pp. 259-270.

Cleary J. G., Wyvill G. (1988) Analysis of An Algorithm for Fast Ray Tracing Using Uniform Space Subdivision, The Visual Comptuer, International Journal of Computer Graphics, vol. 4, No. 2, pp. 65-83.

Bauer M. (1968) Precious Stones, Dover Publications Inc.

Nelson J. B. (Jul. 1989) The Four Optical Attributes of a Diamond, The Journal of Gemmology, vol. 21, No. 7, pp. 434-447.

Wade F.B., Diamonds—A Study of the Factors that Govern Their Value, G. P. Putnam's Sons, The Knickerbocker Press, pp. 52-81.

Whitlock H. P. (Feb. 7, 1917) The Evolution of the Brilliant Cut Diamond, The Jewelers' Circular, vol. LXXIV, No. 1, pp. 115-121.

Dake H. C. (Jan. 1953) Proportions for the Brilliant Cut, The Gemmologist, vol. XXII, No. 258, pp. 17-18.

Inoue K., Quantification and Visualization of Diamond Brilliancy, Journ. Gemmol. Soc., Japan, vol. 20, pp. 153-167.

Lawrence J. (Mar./Apr. 1997) Slow Gear for New Technology, Diamond International, No. 46, pp. 57-63.

Kato M. (1987) Elucidation of the Scintillation, Journal of the Gemmolgoical Society of Japan, vol. 12, No. 1-4, pp. 12-19.

Toriwaki J., Yokoi S. (1987) Rendering Gems by Computer Graphics, Journal of The Gemmolgical Society of Japan, vol. 12, No. 1-4, pp. 3-11.

Rogers D. F., Procedural Elements for Computer Graphics, 2nd Edition, WCB McGraw-Hill 1998, Table of Contents and Chapters 4-5.

Woo M., Neider J., Davis T., OpenGL Programming Guide, 2nd Edition, Addison-Wesley Developers Press 1997, Tables of Contents and Chapters 2, 5, and 7.

Foley J. D., Dam A. V., Feiner S. K., Hughes J. F., Computer Graphics—Priniciples and Practices, 2nd Edition, Addison-Wesley 1990, Table of Contents and Chapters 13, 15-16.

Hall R., Illumination and Color in Computer Generated Imagery, Springer-Verlag, New York 1989, Tables of Contents, Chapters 2-4, and Appendix I.

Long R., Steele N. (1984) *Facet Design*. Seattle Faceting Books, Mercer Island, WA.

* cited by examiner

BOX A:
BASIC DESCRIPTION OF OUR MODEL

We describe a faceted diamond as a convex polyhedron, a three-dimensional object with a surface that is bounded by flat planes and straight edges, with no indentations or clefts. The model requires that all surfaces be faceted, including the girdle, and currently excludes consideration of indented naturals or cavities. To date, we have focused our calculations on the round brilliant cut because of its dominant position in the market, but this model can be used for nearly any fully faceted shape. Our modeled round brilliant has mathematically perfect symmetry, that is, all facets are perfectly shaped, pointed, and aligned. Also, all facet junctions are modeled with the same sharpness and depth.

Because our modeled round brilliant has perfect eight-fold symmetry, only eight numbers (parameters) are required to specify the convex polyhedron that describes its shape (figure A-1). (Modeling other shapes or including asymmetries requires additional parameters.) We defined these eight parameters as:

| | |
|---|---|
| Crown angle | Angle (in degrees) between the bezel facets and the girdle plane |
| Pavilion angle | Angle (in degrees) between the pavilion mains and the girdle plane |
| Table size | Table width (as percent of girdle diameter) |
| Culet size | Culet width (as percent of girdle diameter) |
| Star length | The ratio of the length of the star facets to the distance between the table edge and girdle edge |
| Lower-girdle length | The ratio of the length of the lower-girdle facets to the distance between the center of the culet and girdle edge |
| Girdle thickness | Measured between bezel and pavilion main facets (the thick part of the girdle) and expressed as a percentage of girdle diameter. This differs from the typical use of the term *girdle thickness* (see, e.g., *GIA Diamond Dictionary*, 1993) |
| Girdle facets | Total number of girdle facets |

Other proportions, such as the crown height, pavilion depth, and total depth (expressed as percentages of

*Figure A-1. We used eight parameters—varied across the range given in table 4—to define our geometric model of the round brilliant shape. (A) All linear distances in this profile view can be described as a percentage of the girdle diameter. The enlarged view of the girdle is centered on the position where we measured the girdle thickness. (B) In this view of the table, the star length is shown at 50%, so that the star facets extend halfway from the table to the girdle (when viewed from straight above). (C) In this view of the pavilion, the lower-girdle length is shown at 75%, so that the lower girdle facets extend three-fourths of the distance from the girdle to the culet (when viewed from straight below).*

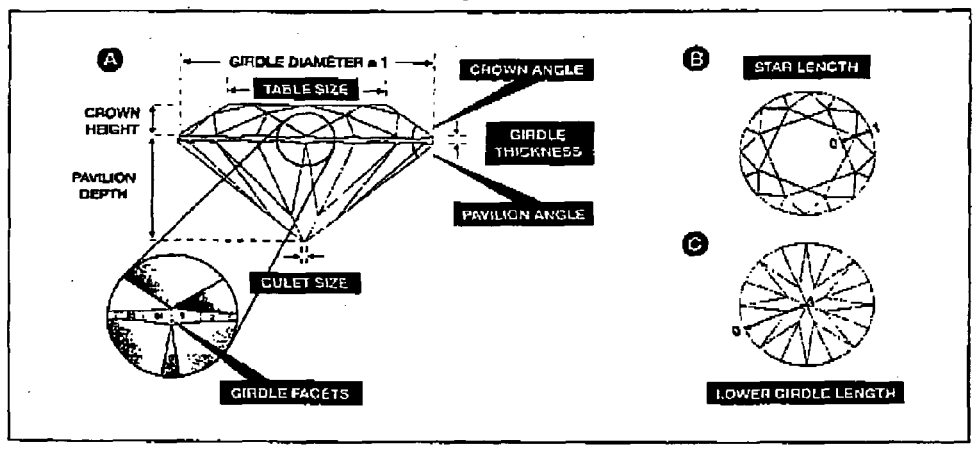

FIG. 1

| Crown Angle | Pavilion Angle | Table Size | Girdle | Star Length | Lower Girdle Length | Culet Size | # of Girdle Facets | Crown Angle | DCLR4 | DCLR3 | DCLR2 |
|---|---|---|---|---|---|---|---|---|---|---|---|
| 20 | 40.5 | 0.56 | 0.005 | 0.5 | 0.75 | 0.03 | 64 | 20 | 4.808136 | 2.290357 | 0.832502 |
| 21 | 40.5 | 0.56 | 0.005 | 0.5 | 0.75 | 0.03 | 64 | 21 | 5.030344 | 2.294424 | 0.787851 |
| 22 | 40.5 | 0.56 | 0.005 | 0.5 | 0.75 | 0.03 | 64 | 22 | 4.746925 | 2.224495 | 0.816247 |
| 23 | 40.5 | 0.56 | 0.005 | 0.5 | 0.75 | 0.03 | 64 | 23 | 4.976609 | 2.33858 | 0.829484 |
| 24 | 40.5 | 0.56 | 0.005 | 0.5 | 0.75 | 0.03 | 64 | 24 | 5.208604 | 2.399793 | 0.833867 |
| 25 | 40.5 | 0.56 | 0.005 | 0.5 | 0.75 | 0.03 | 64 | 25 | 5.320519 | 2.441463 | 0.793886 |
| 26 | 40.5 | 0.56 | 0.005 | 0.5 | 0.75 | 0.03 | 64 | 26 | 5.270065 | 2.391322 | 0.753839 |
| 27 | 40.5 | 0.56 | 0.005 | 0.5 | 0.75 | 0.03 | 64 | 27 | 4.935745 | 2.216659 | 0.755395 |
| 28 | 40.5 | 0.56 | 0.005 | 0.5 | 0.75 | 0.03 | 64 | 28 | 4.930896 | 2.188527 | 0.77895 |
| 29 | 40.5 | 0.56 | 0.005 | 0.5 | 0.75 | 0.03 | 64 | 29 | 4.892483 | 2.183266 | 0.818271 |
| 30 | 40.5 | 0.56 | 0.005 | 0.5 | 0.75 | 0.03 | 64 | 30 | 4.837468 | 2.215199 | 0.847368 |
| 31 | 40.5 | 0.56 | 0.005 | 0.5 | 0.75 | 0.03 | 64 | 31 | 4.976839 | 2.227878 | 0.866889 |
| 32 | 40.5 | 0.56 | 0.005 | 0.5 | 0.75 | 0.03 | 64 | 32 | 5.019174 | 2.277004 | 0.87894 |
| 33 | 40.5 | 0.56 | 0.005 | 0.5 | 0.75 | 0.03 | 64 | 33 | 5.095637 | 2.352677 | 0.892496 |
| 34 | 40.5 | 0.56 | 0.005 | 0.5 | 0.75 | 0.03 | 64 | 34 | 5.266954 | 2.345421 | 0.863241 |
| 35 | 40.5 | 0.56 | 0.005 | 0.5 | 0.75 | 0.03 | 64 | 35 | 5.234717 | 2.266483 | 0.82614 |
| 36 | 40.5 | 0.56 | 0.005 | 0.5 | 0.75 | 0.03 | 64 | 36 | 5.211515 | 2.242278 | 0.788502 |
| 37 | 40.5 | 0.56 | 0.005 | 0.5 | 0.75 | 0.03 | 64 | 37 | 5.202454 | 2.064508 | 0.726241 |
| 38 | 40.5 | 0.56 | 0.005 | 0.5 | 0.75 | 0.03 | 64 | 38 | 4.8685 | 2.044293 | 0.742737 |
| 39 | 40.5 | 0.56 | 0.005 | 0.5 | 0.75 | 0.03 | 64 | 39 | 4.937516 | 2.184872 | 0.794879 |
| 40 | 40.5 | 0.56 | 0.005 | 0.5 | 0.75 | 0.03 | 64 | 40 | 5.051162 | 2.290029 | 0.838353 |
| 41 | 40.5 | 0.56 | 0.005 | 0.5 | 0.75 | 0.03 | 64 | 41 | 5.341886 | 2.37774 | 0.866865 |
| 42 | 40.5 | 0.56 | 0.005 | 0.5 | 0.75 | 0.03 | 64 | 42 | 5.722286 | 2.521091 | 0.862799 |
| 43 | 40.5 | 0.56 | 0.005 | 0.5 | 0.75 | 0.03 | 64 | 43 | 5.690082 | 2.486346 | 0.818338 |
| 44 | 40.5 | 0.56 | 0.005 | 0.5 | 0.75 | 0.03 | 64 | 44 | 6.240864 | 2.632991 | 0.855382 |
| 45 | 40.5 | 0.56 | 0.005 | 0.5 | 0.75 | 0.03 | 64 | 45 | 6.378598 | 2.700116 | 0.851092 |

FIG. 2C

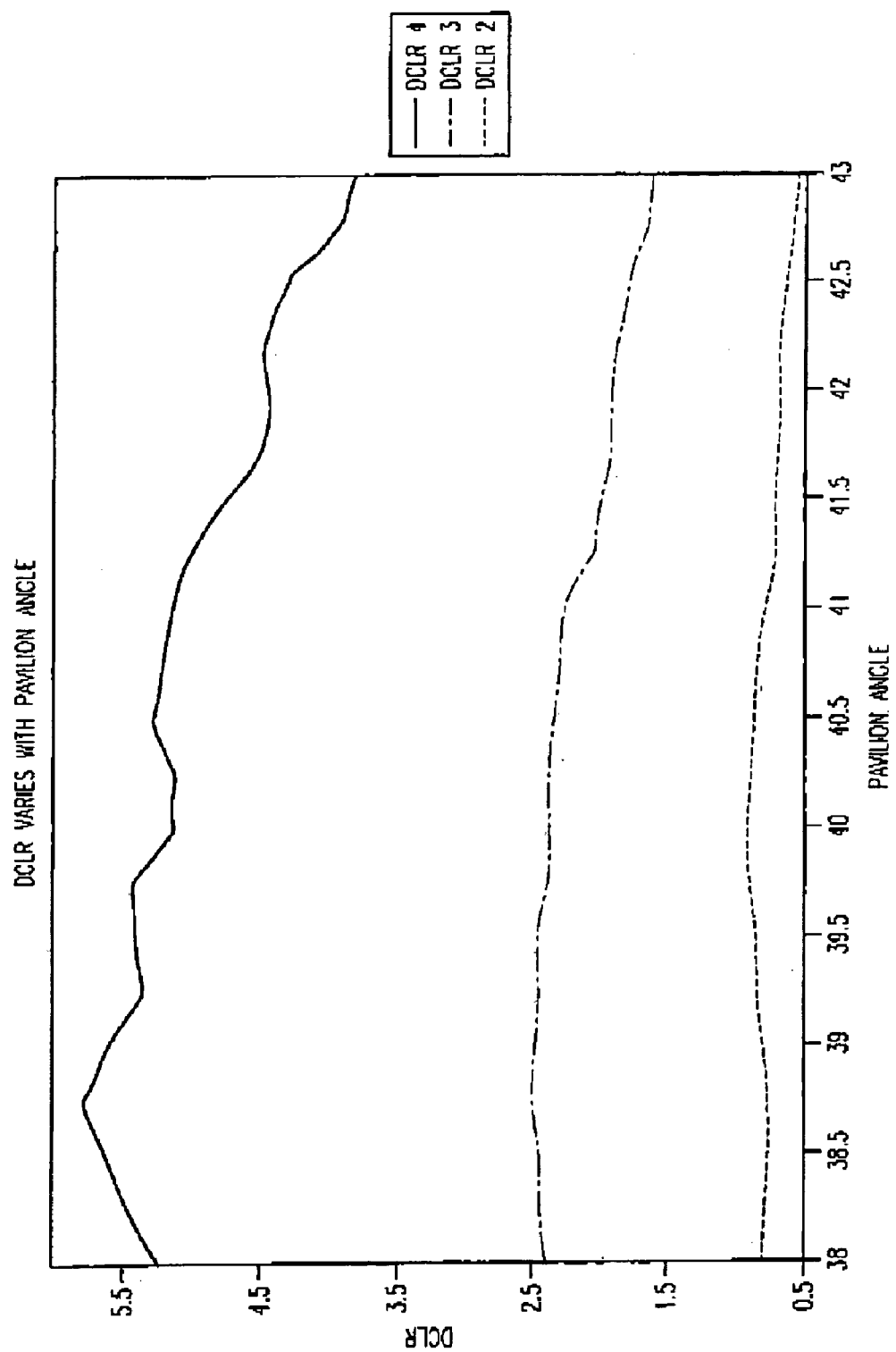

| Crown Angle | Pavilion | Table Size | Girdle | Star Length | Lower Girdle Length | Culet Size | # of Girdle Facets | Pavilion | DCLR4 | DCLR3 | DCLR2 |
|---|---|---|---|---|---|---|---|---|---|---|---|
| 34 | 38 | 0.56 | 0.005 | 0.5 | 0.75 | 0.03 | 64 | 38 | 5.229829 | 2.384659 | 0.810342 |
| 34 | 38.25 | 0.56 | 0.005 | 0.5 | 0.75 | 0.03 | 64 | 38.25 | 5.453779 | 2.430965 | 0.79447 |
| 34 | 38.5 | 0.56 | 0.005 | 0.5 | 0.75 | 0.03 | 64 | 38.5 | 5.638591 | 2.438316 | 0.76528 |
| 34 | 38.75 | 0.56 | 0.005 | 0.5 | 0.75 | 0.03 | 64 | 38.75 | 5.765021 | 2.485844 | 0.765746 |
| 34 | 39 | 0.56 | 0.005 | 0.5 | 0.75 | 0.03 | 64 | 39 | 5.596684 | 2.472669 | 0.810488 |
| 34 | 39.25 | 0.56 | 0.005 | 0.5 | 0.75 | 0.03 | 64 | 39.25 | 5.353917 | 2.458902 | 0.851028 |
| 34 | 39.5 | 0.56 | 0.005 | 0.5 | 0.75 | 0.03 | 64 | 39.5 | 5.401111 | 2.428729 | 0.868444 |
| 34 | 39.75 | 0.56 | 0.005 | 0.5 | 0.75 | 0.03 | 64 | 39.75 | 5.414612 | 2.386446 | 0.901324 |
| 34 | 40 | 0.56 | 0.005 | 0.5 | 0.75 | 0.03 | 64 | 40 | 5.133628 | 2.388464 | 0.908634 |
| 34 | 40.25 | 0.56 | 0.005 | 0.5 | 0.75 | 0.03 | 64 | 40.25 | 5.105611 | 2.387008 | 0.897934 |
| 34 | 40.5 | 0.56 | 0.005 | 0.5 | 0.75 | 0.03 | 64 | 40.5 | 5.266954 | 2.345421 | 0.863241 |
| 34 | 40.75 | 0.56 | 0.005 | 0.5 | 0.75 | 0.03 | 64 | 40.75 | 5.197605 | 2.297761 | 0.831786 |
| 34 | 41 | 0.56 | 0.005 | 0.5 | 0.75 | 0.03 | 64 | 41 | 5.132326 | 2.267499 | 0.794494 |
| 34 | 41.25 | 0.56 | 0.005 | 0.5 | 0.75 | 0.03 | 64 | 41.25 | 5.000269 | 2.048954 | 0.729545 |
| 34 | 41.5 | 0.56 | 0.005 | 0.5 | 0.75 | 0.03 | 64 | 41.5 | 4.728625 | 1.976045 | 0.714573 |
| 34 | 41.75 | 0.56 | 0.005 | 0.5 | 0.75 | 0.03 | 64 | 41.75 | 4.471355 | 1.912248 | 0.700948 |
| 34 | 42 | 0.56 | 0.005 | 0.5 | 0.75 | 0.03 | 64 | 42 | 4.42342 | 1.896277 | 0.688704 |
| 34 | 42.25 | 0.56 | 0.005 | 0.5 | 0.75 | 0.03 | 64 | 42.25 | 4.461586 | 1.866763 | 0.6823 |
| 34 | 42.5 | 0.56 | 0.005 | 0.5 | 0.75 | 0.03 | 64 | 42.5 | 4.302394 | 1.77687 | 0.630612 |
| 34 | 42.75 | 0.56 | 0.005 | 0.5 | 0.75 | 0.03 | 64 | 42.75 | 3.9399 | 1.660786 | 0.584443 |
| 34 | 43 | 0.56 | 0.005 | 0.5 | 0.75 | 0.03 | 64 | 43 | 3.803905 | 1.598593 | 0.554585 |

FIG. 3C

| DCLR (with reference to crown angle and table size) – Low Threshold | | | | | | | |
|---|---|---|---|---|---|---|---|
| Table Size | 20 | 21 | 22 | 23 | 24 | 25 | 26 |
| 0.52 | 4.820357 | 4.939313 | 4.812195 | 4.879748 | 4.932132 | 5.136546 | 5.47201 |
| 0.53 | 4.831093 | 4.950311 | 4.782161 | 4.936139 | 5.029274 | 5.203716 | 5.462488 |
| 0.54 | 4.815453 | 4.973568 | 4.73973 | 4.99687 | 5.064955 | 5.275224 | 5.381007 |
| 0.55 | 4.81028 | 5.009986 | 4.709252 | 5.015546 | 5.160558 | 5.316428 | 5.324799 |
| 0.56 | 4.808136 | 5.030344 | 4.746925 | 4.976609 | 5.208604 | 5.320519 | 5.270066 |
| 0.57 | 4.830171 | 5.026022 | 4.799962 | 4.914508 | 5.230896 | 5.301702 | 5.229205 |
| 0.58 | 4.839072 | 5.026973 | 4.853691 | 4.866287 | 5.127808 | 5.232636 | 5.171616 |
| 0.59 | 4.832706 | 4.982412 | 4.913689 | 4.828904 | 5.028446 | 5.06001 | 5.063859 |
| 0.6 | 4.776394 | 4.960796 | 4.925031 | 4.837146 | 4.928928 | 4.972889 | 4.94316 |
| 0.61 | 4.744611 | 4.902197 | 4.945129 | 4.852798 | 4.834193 | 4.881712 | 4.829108 |
| 0.62 | 4.688475 | 4.801576 | 4.95931 | 4.852435 | 4.67493 | 4.733005 | 4.794239 |
| 0.63 | 4.648858 | 4.677046 | 4.855552 | 4.817368 | 4.600331 | 4.62899 | 4.751064 |
| 0.64 | 4.537254 | 4.648348 | 4.771252 | 4.697781 | 4.578892 | 4.596966 | 4.716511 |
| 0.65 | 4.424109 | 4.57592 | 4.60562 | 4.551181 | 4.548646 | 4.609783 | 4.790281 |
| | | | | | | | |
| 5.917144 | 4.839072 | 5.030344 | 4.95931 | 5.015546 | 5.230896 | 5.320519 | 5.47201 |
| 4.209061 | 4.424109 | 4.57592 | 4.60562 | 4.551181 | 4.548646 | 4.596966 | 4.716511 |

| DCLR (with reference to crown angle and table size) – Low Threshold | | | | | | | |
|---|---|---|---|---|---|---|---|
| Table Size | 27 | 28 | 29 | 30 | 31 | 32 | 33 |
| 0.52 | 5.046131 | 5.022919 | 4.900264 | 4.924492 | 5.300924 | 5.547221 | 5.409065 |
| 0.53 | 5.049688 | 4.971674 | 4.856816 | 4.907846 | 5.193917 | 5.361343 | 5.42549 |
| 0.54 | 5.025958 | 4.971243 | 4.864711 | 4.860688 | 5.180024 | 5.30072 | 5.246033 |
| 0.55 | 5.001634 | 4.987571 | 4.850012 | 4.831711 | 5.041646 | 5.205475 | 5.209404 |
| 0.56 | 4.935745 | 4.930896 | 4.892483 | 4.837468 | 4.978839 | 5.019174 | 5.095637 |
| 0.57 | 4.887668 | 4.885941 | 4.911941 | 4.829027 | 4.941537 | 4.869972 | 5.04464 |
| 0.58 | 4.898555 | 4.891339 | 4.914794 | 4.848868 | 4.867236 | 4.85668 | 4.910879 |
| 0.59 | 4.898404 | 4.923511 | 4.923349 | 4.835056 | 4.829714 | 4.884636 | 4.808952 |
| 0.6 | 4.856815 | 4.979128 | 5.001942 | 4.839071 | 4.871782 | 4.877656 | 4.829757 |
| 0.61 | 4.954681 | 5.025748 | 5.084723 | 4.90441 | 4.855851 | 4.821782 | 4.872046 |
| 0.62 | 4.9282 | 5.052294 | 5.104288 | 4.985726 | 4.928198 | 4.859495 | 4.846723 |
| 0.63 | 4.846364 | 5.05549 | 5.109083 | 5.003274 | 4.924906 | 4.88104 | 4.789814 |
| 0.64 | 4.830715 | 5.021953 | 5.088545 | 4.904007 | 4.980077 | 4.944995 | 4.74344 |
| 0.65 | 4.810596 | 4.966058 | 5.034687 | 4.773245 | 4.898147 | 5.056408 | 4.666156 |
| | | | | | | | |
| 5.917144 | 5.049688 | 5.05549 | 5.109083 | 5.003274 | 5.300924 | 5.547221 | 5.42549 |
| 4.209061 | 4.810596 | 4.885941 | 4.850012 | 4.773245 | 4.829714 | 4.821782 | 4.666156 |

| DCLR (with reference to crown angle and table size) – Low Threshold | | | | | | | |
|---|---|---|---|---|---|---|---|
| Table Size | 34 | 35 | 36 | 37 | 38 | 39 | 40 |
| 0.52 | 5.719851 | 5.597977 | 5.884889 | 5.917144 | 5.80973 | 5.789427 | 5.873313 |
| 0.53 | 5.667446 | 5.469215 | 5.587521 | 5.701767 | 5.446033 | 5.477491 | 5.601686 |
| 0.54 | 5.599147 | 5.50738 | 5.668524 | 5.41251 | 5.147505 | 5.164859 | 5.435375 |
| 0.55 | 5.428893 | 5.377802 | 5.466541 | 5.386262 | 4.957466 | 5.116874 | 5.231116 |
| 0.56 | 5.266954 | 5.234717 | 5.211515 | 2.202454 | 4.8685 | 4.937516 | 5.051162 |
| 0.57 | 5.037557 | 5.061297 | 5.20193 | 5.123727 | 4.72041 | 4.966408 | 4.988474 |
| 0.58 | 4.934068 | 4.926477 | 5.154472 | 4.994656 | 4.809853 | 4.780978 | 5.034633 |
| 0.59 | 4.934716 | 4.874027 | 4.939944 | 4.849796 | 4.74409 | 4.865011 | 5.021238 |
| 0.6 | 4.923382 | 4.867877 | 4.808313 | 4.560933 | 4.618767 | 4.896856 | 4.966398 |
| 0.61 | 4.922016 | 4.850042 | 4.95823 | 4.532966 | 4.411391 | 4.908094 | 4.921952 |
| 0.62 | 4.819245 | 4.816324 | 4.888901 | 4.577857 | 4.231437 | 4.647369 | 4.69606 |
| 0.63 | 4.80074 | 4.803556 | 4.898934 | 4.634762 | 4.320362 | 4.423799 | 4.344308 |
| 0.64 | 4.76932 | 4.77176 | 4.960207 | 4.654107 | 4.333075 | 4.459725 | 4.245546 |
| 0.65 | 4.666667 | 4.762845 | 4.919437 | 4.63904 | 4.543718 | 4.445769 | 4.209061 |
| | | | | | | | |
| 5.917144 | 5.719851 | 5.597977 | 5.884889 | 5.917144 | 5.80973 | 5.789427 | 5.873313 |
| 4.209061 | 4.666667 | 4.762845 | 4.808313 | 4.532966 | 4.231437 | 4.423799 | 4.209061 |

Fig. 4C

| DCLR (with reference to crown angle and table size) – Medium Threshold | | | | | | | |
|---|---|---|---|---|---|---|---|
| Table Size | | | | | | | |
| | 20 | 21 | 22 | 23 | 24 | 25 | 26 |
| 0.52 | 0.869399 | 0.836137 | 0.80803 | 0.835899 | 0.843502 | 0.85091 | 0.809153 |
| 0.53 | 0.877923 | 0.822521 | 0.813364 | 0.838058 | 0.847552 | 0.848716 | 0.796386 |
| 0.54 | 0.864041 | 0.809538 | 0.818503 | 0.837076 | 0.847447 | 0.83708 | 0.779687 |
| 0.55 | 0.848831 | 0.798123 | 0.819221 | 0.833652 | 0.843494 | 0.817627 | 0.76689 |
| 0.56 | 0.832502 | 0.787851 | 0.816247 | 0.829484 | 0.833867 | 0.793886 | 0.753839 |
| 0.57 | 0.815732 | 0.779437 | 0.810141 | 0.819743 | 0.815161 | 0.766867 | 0.741619 |
| 0.58 | 0.797956 | 0.774204 | 0.800595 | 0.807438 | 0.789799 | 0.748017 | 0.732856 |
| 0.59 | 0.778568 | 0.770116 | 0.786796 | 0.790334 | 0.754238 | 0.733273 | 0.727433 |
| 0.6 | 0.75774 | 0.763044 | 0.769118 | 0.764915 | 0.721713 | 0.718529 | 0.722913 |
| 0.61 | 0.736879 | 0.752012 | 0.747005 | 0.729899 | 0.70267 | 0.7069 | 0.719931 |
| 0.62 | 0.718635 | 0.73586 | 0.723917 | 0.692448 | 0.686848 | 0.696845 | 0.706851 |
| 0.63 | 0.7046 | 0.71398 | 0.684854 | 0.667495 | 0.677278 | 0.68524 | 0.695101 |
| 0.64 | 0.690372 | 0.683461 | 0.658024 | 0.65122 | 0.668167 | 0.673809 | 0.684811 |
| 0.65 | 0.673199 | 0.650935 | 0.626648 | 0.642425 | 0.658586 | 0.663739 | 0.677502 |
| | | | | | | | |
| 0.925808 | 0.869399 | 0.836137 | 0.819221 | 0.838058 | 0.847552 | 0.85091 | 0.809153 |
| 0.626648 | 0.673199 | 0.650935 | 0.626648 | 0.642425 | 0.658586 | 0.663739 | 0.677502 |

| DCLR (with reference to crown angle and table size) – MediumThreshold | | | | | | | |
|---|---|---|---|---|---|---|---|
| Table Size | | | | | | | |
| | 27 | 28 | 29 | 30 | 31 | 32 | 33 |
| 0.52 | 0.777319 | 0.778176 | 0.822632 | 0.843431 | 0.847797 | 0.861754 | 0.875922 |
| 0.53 | 0.771709 | 0.783916 | 0.830842 | 0.846235 | 0.850115 | 0.86672 | 0.883218 |
| 0.54 | 0.763208 | 0.790628 | 0.850807 | 0.845471 | 0.856028 | 0.87168 | 0.889323 |
| 0.55 | 0.757037 | 0.788203 | 0.825114 | 0.845811 | 0.86181 | 0.875469 | 0.891391 |
| 0.56 | 0.755395 | 0.77895 | 0.818271 | 0.847369 | 0.866889 | 0.87894 | 0.892496 |
| 0.57 | 0.752256 | 0.768499 | 0.812823 | 0.847118 | 0.870053 | 0.883652 | 0.887093 |
| 0.58 | 0.743976 | 0.764024 | 0.805049 | 0.844276 | 0.870545 | 0.884338 | 0.886611 |
| 0.59 | 0.738604 | 0.760982 | 0.796679 | 0.838495 | 0.867996 | 0.882911 | 0.888422 |
| 0.6 | 0.733238 | 0.756402 | 0.79058 | 0.830705 | 0.862142 | 0.878539 | 0.887673 |
| 0.61 | 0.728434 | 0.751028 | 0.785106 | 0.823538 | 0.853612 | 0.871361 | 0.884483 |
| 0.62 | 0.728386 | 0.747616 | 0.778597 | 0.818689 | 0.843502 | 0.86203 | 0.876854 |
| 0.63 | 0.720619 | 0.748032 | 0.775226 | 0.812894 | 0.834812 | 0.851162 | 0.871194 |
| 0.64 | 0.712404 | 0.74136 | 0.776011 | 0.808094 | 0.826394 | 0.838456 | 0.861161 |
| 0.65 | 0.703279 | 0.732282 | 0.771764 | 0.807634 | 0.818321 | 0.828758 | 0.847599 |
| | | | | | | | |
| 0.925808 | 0.777319 | 0.790628 | 0.830842 | 0.847369 | 0.870545 | 0.884338 | 0.892496 |
| 0.626648 | 0.703279 | 0.732282 | 0.771764 | 0.807634 | 0.818321 | 0.828758 | 0.847599 |

| DCLR (with reference to crown angle and table size) –Medium Threshold | | | | | | | |
|---|---|---|---|---|---|---|---|
| Table Size | | | | | | | |
| | 34 | 35 | 36 | 37 | 38 | 39 | 40 |
| 0.52 | 0.884455 | 0.874472 | 0.83522 | 0.794012 | 0.820641 | 0.879217 | 0.925808 |
| 0.53 | 0.876516 | 0.856473 | 0.817092 | 0.762049 | 0.789167 | 0.867094 | 0.904074 |
| 0.54 | 0.869909 | 0.839013 | 0.805369 | 0.740686 | 0.765218 | 0.839051 | 0.883163 |
| 0.55 | 0.865573 | 0.828396 | 0.796559 | 0.733089 | 0.749023 | 0.816077 | 0.859523 |
| 0.56 | 0.863241 | 0.82614 | 0.788502 | 0.726241 | 0.742737 | 0.794879 | 0.838353 |
| 0.57 | 0.863287 | 0.833798 | 0.79141 | 0.718304 | 0.739348 | 0.781494 | 0.81613 |
| 0.58 | 0.871497 | 0.841303 | 0.796993 | 0.708974 | 0.737052 | 0.774727 | 0.798629 |
| 0.59 | 0.876342 | 0.847675 | 0.79937 | 0.701276 | 0.731596 | 0.765057 | 0.791844 |
| 0.6 | 0.877821 | 0.852095 | 0.800216 | 0.695151 | 0.723074 | 0.757208 | 0.779571 |
| 0.61 | 0.875527 | 0.853844 | 0.80037 | 0.68666 | 0.715178 | 0.747575 | 0.7609 |
| 0.62 | 0.872329 | 0.851574 | 0.798912 | 0.678443 | 0.705287 | 0.734623 | 0.742909 |
| 0.63 | 0.868553 | 0.84678 | 0.795258 | 0.671959 | 0.691424 | 0.721272 | 0.72133 |
| 0.64 | 0.863065 | 0.842193 | 0.788609 | 0.665847 | 0.677519 | 0.701312 | 0.700518 |
| 0.65 | 0.856115 | 0.836879 | 0.781369 | 0.657474 | 0.662932 | 0.677162 | 0.677832 |
| | | | | | | | |
| 0.925808 | 0.884455 | 0.874472 | 0.83522 | 0.794012 | 0.820641 | 0.879217 | 0.925808 |
| 0.626648 | 0.856115 | 0.82614 | 0.781369 | 0.657474 | 0.662932 | 0.677162 | 0.677832 |

Fig. 5C

| DCLR (with reference to crown angle and table size) – High Threshold | | | | | | | |
|---|---|---|---|---|---|---|---|
| Table Size | 20 | 21 | 22 | 23 | 24 | 25 | 26 |
| 0.52 | 2.30223 | 2.335418 | 2.193281 | 2.26173 | 2.37404 | 2.507397 | 2.526301 |
| 0.53 | 2.304005 | 2.329233 | 2.206791 | 2.306826 | 2.39802 | 2.514777 | 2.509276 |
| 0.54 | 2.313594 | 2.324573 | 2.213602 | 2.324592 | 2.403448 | 2.508406 | 2.478646 |
| 0.55 | 2.309849 | 2.312601 | 2.220023 | 2.336642 | 2.405159 | 2.484451 | 2.438782 |
| 0.56 | 2.290357 | 2.294424 | 2.224496 | 2.33858 | 2.399793 | 2.441463 | 2.391322 |
| 0.57 | 2.271913 | 2.271483 | 2.227569 | 2.333174 | 2.383975 | 2.386016 | 2.351939 |
| 0.58 | 2.256496 | 2.245258 | 2.224163 | 2.304914 | 2.360532 | 2.314879 | 2.301797 |
| 0.59 | 2.232624 | 2.202266 | 2.212221 | 2.260972 | 2.311398 | 2.259275 | 2.232498 |
| 0.6 | 2.208264 | 2.159124 | 2.200003 | 2.212965 | 2.237939 | 2.210266 | 2.178597 |
| 0.61 | 2.173768 | 2.12016 | 2.173376 | 2.17039 | 2.13402 | 2.141835 | 2.149987 |
| 0.62 | 2.122214 | 2.096023 | 2.123691 | 2.127622 | 2.072749 | 2.078855 | 2.126691 |
| 0.63 | 2.06516 | 2.062477 | 2.080321 | 2.051564 | 2.025091 | 2.050181 | 2.090416 |
| 0.64 | 2.008445 | 2.013197 | 2.020619 | 1.992772 | 1.989728 | 2.045131 | 2.068072 |
| 0.65 | 1.955188 | 1.937305 | 1.918244 | 1.933478 | 1.958347 | 2.032557 | 2.061226 |
| | | | | | | | |
| 2.634142 | 2.313594 | 2.335418 | 2.227569 | 2.33858 | 2.405159 | 2.514777 | 2.526301 |
| 1.817691 | 1.955188 | 1.937305 | 1.918244 | 1.933478 | 1.958347 | 2.032557 | 2.061226 |

| DCLR (with reference to crown angle and table size) – High Threshold | | | | | | | |
|---|---|---|---|---|---|---|---|
| Table Size | 27 | 28 | 29 | 30 | 31 | 32 | 33 |
| 0.52 | 2.292136 | 2.274878 | 2.213491 | 2.263117 | 2.318694 | 2.396675 | 2.404173 |
| 0.53 | 2.298946 | 2.263959 | 2.214281 | 2.254018 | 2.292316 | 2.357868 | 2.407772 |
| 0.54 | 2.285992 | 2.241246 | 2.210366 | 2.236267 | 2.258911 | 2.338892 | 2.402759 |
| 0.55 | 2.257812 | 2.216801 | 2.205081 | 2.230745 | 2.23362 | 2.307276 | 2.387627 |
| 0.56 | 2.216659 | 2.188527 | 2.193266 | 2.215199 | 2.227878 | 2.277004 | 2.352677 |
| 0.57 | 2.174897 | 2.168027 | 2.165533 | 2.209583 | 2.229816 | 2.269163 | 2.308357 |
| 0.58 | 2.145702 | 2.154863 | 2.149589 | 2.200822 | 2.236743 | 2.287629 | 2.271622 |
| 0.59 | 2.133239 | 2.144914 | 2.143788 | 2.186567 | 2.241172 | 2.295577 | 2.27709 |
| 0.6 | 2.131499 | 2.149113 | 2.144203 | 2.173946 | 2.236122 | 2.295137 | 2.289057 |
| 0.61 | 2.119507 | 2.155081 | 2.15407 | 2.155259 | 2.237656 | 2.28136 | 2.294391 |
| 0.62 | 2.105778 | 2.154286 | 2.170974 | 2.145525 | 2.232452 | 2.271611 | 2.292635 |
| 0.63 | 2.09862 | 2.127028 | 2.180911 | 2.147401 | 2.22679 | 2.264624 | 2.270502 |
| 0.64 | 2.069036 | 2.106709 | 2.147721 | 2.146403 | 2.251035 | 2.259674 | 2.227586 |
| 0.65 | 2.060949 | 2.075713 | 2.090885 | 2.101592 | 2.257497 | 2.276021 | 2.198133 |
| | | | | | | | |
| 2.634142 | 2.298946 | 2.274878 | 2.214281 | 2.263117 | 2.318694 | 2.396675 | 2.407772 |
| 1.817691 | 2.060949 | 2.075713 | 2.090885 | 2.101592 | 2.22679 | 2.259674 | 2.198133 |

| DCLR (with reference to crown angle and table size) – High Threshold | | | | | | | |
|---|---|---|---|---|---|---|---|
| Table Size | 34 | 35 | 36 | 37 | 38 | 39 | 40 |
| 0.52 | 2.497725 | 2.465286 | 2.491756 | 2.44923 | 2.439982 | 2.564655 | 2.634142 |
| 0.53 | 2.482186 | 2.416049 | 2.418603 | 2.314221 | 2.3111 | 2.42418 | 2.558103 |
| 0.54 | 2.43167 | 2.406068 | 2.41833 | 2.163918 | 2.17034 | 2.336082 | 2.479787 |
| 0.55 | 2.386556 | 2.3448 | 2.355507 | 2.12493 | 2.084375 | 2.253937 | 2.383294 |
| 0.56 | 2.345421 | 2.266483 | 2.242278 | 2.064508 | 2.044293 | 2.194872 | 2.290029 |
| 0.57 | 2.313417 | 2.228194 | 2.211097 | 2.043476 | 2.015128 | 2.145181 | 2.237913 |
| 0.58 | 2.273146 | 2.240134 | 2.194433 | 1.999885 | 2.008567 | 2.113333 | 2.21557 |
| 0.59 | 2.257595 | 2.239302 | 2.189499 | 1.957835 | 1.984806 | 2.123374 | 2.162441 |
| 0.6 | 2.245972 | 2.247063 | 2.193257 | 1.904927 | 1.918563 | 2.095038 | 2.143703 |
| 0.61 | 2.254045 | 2.256015 | 2.216941 | 1.905148 | 1.861386 | 2.041885 | 2.078729 |
| 0.62 | 2.248172 | 2.237498 | 2.212457 | 1.896957 | 1.817691 | 1.987117 | 1.998416 |
| 0.63 | 2.248214 | 2.24508 | 2.19211 | 1.899925 | 1.823452 | 1.910596 | 1.942233 |
| 0.64 | 2.230171 | 2.245706 | 2.211771 | 1.881567 | 1.819499 | 1.869007 | 1.895533 |
| 0.65 | 2.193809 | 2.230203 | 2.219945 | 1.891284 | 1.826914 | 1.88438 | 1.869818 |
| | | | | | | | |
| 2.634142 | 2.497725 | 2.465286 | 2.491756 | 2.44923 | 2.439982 | 2.564655 | 2.634142 |
| 1.817691 | 2.193809 | 2.228194 | 2.189499 | 1.881567 | 1.817691 | 1.88438 | 1.869818 |

| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
|---|---|---|---|---|---|---|---|---|---|---|
| 34 | 40.5 | 0.56 | 0.005 | 0.3 | 0.75 | 0.03 | 64 | 5.611284 | 10 | 4 |
| 34 | 40.5 | 0.56 | 0.005 | 0.32 | 0.75 | 0.03 | 64 | 5.528535 | 10 | 4 |
| 34 | 40.5 | 0.56 | 0.005 | 0.34 | 0.75 | 0.03 | 64 | 5.467026 | 10 | 4 |
| 34 | 40.5 | 0.56 | 0.005 | 0.36 | 0.75 | 0.03 | 64 | 5.385497 | 10 | 4 |
| 34 | 40.5 | 0.56 | 0.005 | 0.38 | 0.75 | 0.03 | 64 | 5.397657 | 10 | 4 |
| 34 | 40.5 | 0.56 | 0.005 | 0.4 | 0.75 | 0.03 | 64 | 5.319126 | 10 | 4 |
| 34 | 40.5 | 0.56 | 0.005 | 0.42 | 0.75 | 0.03 | 64 | 5.248807 | 10 | 4 |
| 34 | 40.5 | 0.56 | 0.005 | 0.44 | 0.75 | 0.03 | 64 | 5.188517 | 10 | 4 |
| 34 | 40.5 | 0.56 | 0.005 | 0.46 | 0.75 | 0.03 | 64 | 5.181513 | 10 | 4 |
| 34 | 40.5 | 0.56 | 0.005 | 0.48 | 0.75 | 0.03 | 64 | 5.180843 | 10 | 4 |
| 34 | 40.5 | 0.56 | 0.005 | 0.5 | 0.75 | 0.03 | 64 | 5.266954 | 10 | 4 |
| 34 | 40.5 | 0.56 | 0.005 | 0.52 | 0.75 | 0.03 | 64 | 5.31061 | 10 | 4 |
| 34 | 40.5 | 0.56 | 0.005 | 0.54 | 0.75 | 0.03 | 64 | 5.406484 | 10 | 4 |
| 34 | 40.5 | 0.56 | 0.005 | 0.56 | 0.75 | 0.03 | 64 | 5.436373 | 10 | 4 |
| 34 | 40.5 | 0.56 | 0.005 | 0.58 | 0.75 | 0.03 | 64 | 5.383246 | 10 | 4 |
| 34 | 40.5 | 0.56 | 0.005 | 0.6 | 0.75 | 0.03 | 64 | 5.402035 | 10 | 4 |
| 34 | 40.5 | 0.56 | 0.005 | 0.62 | 0.75 | 0.03 | 64 | 5.429171 | 10 | 4 |
| 34 | 40.5 | 0.56 | 0.005 | 0.64 | 0.75 | 0.03 | 64 | 5.634116 | 10 | 4 |
| 34 | 40.5 | 0.56 | 0.005 | 0.66 | 0.75 | 0.03 | 64 | 5.597479 | 10 | 4 |
| 34 | 40.5 | 0.56 | 0.005 | 0.68 | 0.75 | 0.03 | 64 | 5.522144 | 10 | 4 |
| 34 | 40.5 | 0.56 | 0.005 | 0.7 | 0.75 | 0.03 | 64 | 5.515765 | 10 | 4 |
| 34 | 40.5 | 0.56 | 0.005 | 0.72 | 0.75 | 0.03 | 64 | 5.357773 | 10 | 4 |
| 34 | 40.5 | 0.56 | 0.005 | 0.74 | 0.75 | 0.03 | 64 | 5.126675 | 10 | 4 |
| 36 | 40.5 | 0.56 | 0.005 | 0.3 | 0.75 | 0.03 | 64 | 5.630651 | 10 | 4 |
| 36 | 40.5 | 0.56 | 0.005 | 0.32 | 0.75 | 0.03 | 64 | 5.69428 | 10 | 4 |
| 36 | 40.5 | 0.56 | 0.005 | 0.34 | 0.75 | 0.03 | 64 | 5.471578 | 10 | 4 |
| 36 | 40.5 | 0.56 | 0.005 | 0.36 | 0.75 | 0.03 | 64 | 5.358874 | 10 | 4 |
| 36 | 40.5 | 0.56 | 0.005 | 0.38 | 0.75 | 0.03 | 64 | 5.228163 | 10 | 4 |
| 36 | 40.5 | 0.56 | 0.005 | 0.4 | 0.75 | 0.03 | 64 | 5.153474 | 10 | 4 |
| 36 | 40.5 | 0.56 | 0.005 | 0.42 | 0.75 | 0.03 | 64 | 5.157299 | 10 | 4 |
| 36 | 40.5 | 0.56 | 0.005 | 0.44 | 0.75 | 0.03 | 64 | 5.179285 | 10 | 4 |
| 36 | 40.5 | 0.56 | 0.005 | 0.46 | 0.75 | 0.03 | 64 | 5.315996 | 10 | 4 |
| 36 | 40.5 | 0.56 | 0.005 | 0.48 | 0.75 | 0.03 | 64 | 5.207225 | 10 | 4 |
| 36 | 40.5 | 0.56 | 0.005 | 0.5 | 0.75 | 0.03 | 64 | 5.211515 | 10 | 4 |
| 36 | 40.5 | 0.56 | 0.005 | 0.52 | 0.75 | 0.03 | 64 | 5.397549 | 10 | 4 |
| 36 | 40.5 | 0.56 | 0.005 | 0.54 | 0.75 | 0.03 | 64 | 5.594171 | 10 | 4 |
| 36 | 40.5 | 0.56 | 0.005 | 0.56 | 0.75 | 0.03 | 64 | 5.689546 | 10 | 4 |
| 36 | 40.5 | 0.56 | 0.005 | 0.58 | 0.75 | 0.03 | 64 | 5.599288 | 10 | 4 |
| 36 | 40.5 | 0.56 | 0.005 | 0.6 | 0.75 | 0.03 | 64 | 5.853835 | 10 | 4 |
| 36 | 40.5 | 0.56 | 0.005 | 0.62 | 0.75 | 0.03 | 64 | 5.468048 | 10 | 4 |
| 36 | 40.5 | 0.56 | 0.005 | 0.64 | 0.75 | 0.03 | 64 | 5.337958 | 10 | 4 |
| 36 | 40.5 | 0.56 | 0.005 | 0.66 | 0.75 | 0.03 | 64 | 5.163907 | 10 | 4 |
| 36 | 40.5 | 0.56 | 0.005 | 0.68 | 0.75 | 0.03 | 64 | 5.061842 | 10 | 4 |
| 36 | 40.5 | 0.56 | 0.005 | 0.7 | 0.75 | 0.03 | 64 | 5.004612 | 10 | 4 |
| 36 | 40.5 | 0.56 | 0.005 | 0.72 | 0.75 | 0.03 | 64 | 4.839458 | 10 | 4 |
| 36 | 40.5 | 0.56 | 0.005 | 0.74 | 0.75 | 0.03 | 64 | 4.93131 | 10 | 4 |
| 25 | 40.5 | 0.56 | 0.005 | 0.3 | 0.75 | 0.03 | 64 | 5.041583 | 10 | 4 |
| 25 | 40.5 | 0.56 | 0.005 | 0.32 | 0.75 | 0.03 | 64 | 5.039889 | 10 | 4 |
| 25 | 40.5 | 0.56 | 0.005 | 0.34 | 0.75 | 0.03 | 64 | 5.014502 | 10 | 4 |
| 25 | 40.5 | 0.56 | 0.005 | 0.36 | 0.75 | 0.03 | 64 | 5.024592 | 10 | 4 |

Fig. 7B

| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
|---|---|---|---|---|---|---|---|---|---|---|
| 25 | 40.5 | 0.56 | 0.005 | 0.38 | 0.75 | 0.03 | 64 | 5.032936 | 10 | 4 |
| 25 | 40.5 | 0.56 | 0.005 | 0.4 | 0.75 | 0.03 | 64 | 5.082992 | 10 | 4 |
| 25 | 40.5 | 0.56 | 0.005 | 0.42 | 0.75 | 0.03 | 64 | 5.097748 | 10 | 4 |
| 25 | 40.5 | 0.56 | 0.005 | 0.44 | 0.75 | 0.03 | 64 | 5.136455 | 10 | 4 |
| 25 | 40.5 | 0.56 | 0.005 | 0.46 | 0.75 | 0.03 | 64 | 5.203904 | 10 | 4 |
| 25 | 40.5 | 0.56 | 0.005 | 0.48 | 0.75 | 0.03 | 64 | 5.248361 | 10 | 4 |
| 25 | 40.5 | 0.56 | 0.005 | 0.5 | 0.75 | 0.03 | 64 | 5.320519 | 10 | 4 |
| 25 | 40.5 | 0.56 | 0.005 | 0.52 | 0.75 | 0.03 | 64 | 5.363032 | 10 | 4 |
| 25 | 40.5 | 0.56 | 0.005 | 0.54 | 0.75 | 0.03 | 64 | 5.406238 | 10 | 4 |
| 25 | 40.5 | 0.56 | 0.005 | 0.56 | 0.75 | 0.03 | 64 | 5.387797 | 10 | 4 |
| 25 | 40.5 | 0.56 | 0.005 | 0.58 | 0.75 | 0.03 | 64 | 5.306217 | 10 | 4 |
| 25 | 40.5 | 0.56 | 0.005 | 0.6 | 0.75 | 0.03 | 64 | 5.252345 | 10 | 4 |
| 25 | 40.5 | 0.56 | 0.005 | 0.62 | 0.75 | 0.03 | 64 | 5.148876 | 10 | 4 |
| 25 | 40.5 | 0.56 | 0.005 | 0.64 | 0.75 | 0.03 | 64 | 5.025955 | 10 | 4 |
| 25 | 40.5 | 0.56 | 0.005 | 0.66 | 0.75 | 0.03 | 64 | 4.929556 | 10 | 4 |
| 25 | 40.5 | 0.56 | 0.005 | 0.68 | 0.75 | 0.03 | 64 | 4.894349 | 10 | 4 |
| 25 | 40.5 | 0.56 | 0.005 | 0.7 | 0.75 | 0.03 | 64 | 4.916253 | 10 | 4 |
| 25 | 40.5 | 0.56 | 0.005 | 0.72 | 0.75 | 0.03 | 64 | 4.820984 | 10 | 4 |
| 25 | 40.5 | 0.56 | 0.005 | 0.74 | 0.75 | 0.03 | 64 | 4.777098 | 10 | 4 |

| Fig. 8 | | | | | | | | | | |
|---|---|---|---|---|---|---|---|---|---|---|
| Crown Angle | Pavillion Angle | Table Size | Culet Size | Star Length | Lower Girdle Length | Girdle Thickness | # of Girdle Facets | DCLR3 | Wavelength Sampling Interval (nm) | Brightness Cutoff Threshold Factor |
| 34 | 40.5 | 0.56 | 0.005 | 0.34 | 0.75 | 0.03 | 64 | 2.447601 | 10 | 3 |
| 34 | 40.5 | 0.56 | 0.005 | 0.36 | 0.75 | 0.03 | 64 | 2.373012 | 10 | 3 |
| 34 | 40.5 | 0.56 | 0.005 | 0.34 | 0.75 | 0.03 | 64 | 2.421435 | 10 | 3 |
| 34 | 40.5 | 0.56 | 0.005 | 0.36 | 0.75 | 0.03 | 64 | 2.45529 | 10 | 3 |
| 34 | 40.5 | 0.56 | 0.005 | 0.38 | 0.75 | 0.03 | 64 | 2.432463 | 10 | 3 |
| 34 | 40.5 | 0.56 | 0.005 | 0.4 | 0.75 | 0.03 | 64 | 2.400016 | 10 | 3 |
| 34 | 40.5 | 0.56 | 0.005 | 0.42 | 0.75 | 0.03 | 64 | 2.364763 | 10 | 3 |
| 34 | 40.5 | 0.56 | 0.005 | 0.44 | 0.75 | 0.03 | 64 | 2.33638 | 10 | 3 |
| 34 | 40.5 | 0.56 | 0.005 | 0.46 | 0.75 | 0.03 | 64 | 2.351346 | 10 | 3 |
| 34 | 40.5 | 0.56 | 0.005 | 0.48 | 0.75 | 0.03 | 64 | 2.35375 | 10 | 3 |
| 34 | 40.5 | 0.56 | 0.005 | 0.5 | 0.75 | 0.03 | 64 | 2.345421 | 10 | 3 |
| 34 | 40.5 | 0.56 | 0.005 | 0.52 | 0.75 | 0.03 | 64 | 2.348337 | 10 | 3 |
| 34 | 40.5 | 0.56 | 0.005 | 0.54 | 0.75 | 0.03 | 64 | 2.348061 | 10 | 3 |
| 34 | 40.5 | 0.56 | 0.005 | 0.56 | 0.75 | 0.03 | 64 | 2.349984 | 10 | 3 |
| 34 | 40.5 | 0.56 | 0.005 | 0.58 | 0.75 | 0.03 | 64 | 2.367726 | 10 | 3 |
| 34 | 40.5 | 0.56 | 0.005 | 0.6 | 0.75 | 0.03 | 64 | 2.397798 | 10 | 3 |
| 34 | 40.5 | 0.56 | 0.005 | 0.62 | 0.75 | 0.03 | 64 | 2.409934 | 10 | 3 |
| 34 | 40.5 | 0.56 | 0.005 | 0.64 | 0.75 | 0.03 | 64 | 2.413453 | 10 | 3 |
| 34 | 40.5 | 0.56 | 0.005 | 0.66 | 0.75 | 0.03 | 64 | 2.382642 | 10 | 3 |
| 34 | 40.5 | 0.56 | 0.005 | 0.68 | 0.75 | 0.03 | 64 | 2.374008 | 10 | 3 |
| 34 | 40.5 | 0.56 | 0.005 | 0.7 | 0.75 | 0.03 | 64 | 2.370136 | 10 | 3 |
| 34 | 40.5 | 0.56 | 0.005 | 0.72 | 0.75 | 0.03 | 64 | 2.338764 | 10 | 3 |
| 34 | 40.5 | 0.56 | 0.005 | 0.74 | 0.75 | 0.03 | 64 | 2.295892 | 10 | 3 |

| Fig. 9 | | | | | | | | | | |
|---|---|---|---|---|---|---|---|---|---|---|
| Crown Angle | Pavillion Angle | Table Size | Culet Size | Star Length | Lower Girdle Length | Girdle Thickness | # of Girdle Facets | DCLR2 | Wavelength Sampling Interval (nm) | Brightness Cutoff Threshold Factor |
| 34 | 40.5 | 0.56 | 0.005 | 0.3 | 0.75 | 0.03 | 64 | 0.811378 | 10 | 2 |
| 34 | 40.5 | 0.56 | 0.005 | 0.32 | 0.75 | 0.03 | 64 | 0.814937 | 10 | 2 |
| 34 | 40.5 | 0.56 | 0.005 | 0.34 | 0.75 | 0.03 | 64 | 0.833334 | 10 | 2 |
| 34 | 40.5 | 0.56 | 0.005 | 0.36 | 0.75 | 0.03 | 64 | 0.84361 | 10 | 2 |
| 34 | 40.5 | 0.56 | 0.005 | 0.38 | 0.75 | 0.03 | 64 | 0.844934 | 10 | 2 |
| 34 | 40.5 | 0.56 | 0.005 | 0.4 | 0.75 | 0.03 | 64 | 0.842936 | 10 | 2 |
| 34 | 40.5 | 0.56 | 0.005 | 0.42 | 0.75 | 0.03 | 64 | 0.844056 | 10 | 2 |
| 34 | 40.5 | 0.56 | 0.005 | 0.44 | 0.75 | 0.03 | 64 | 0.849681 | 10 | 2 |
| 34 | 40.5 | 0.56 | 0.005 | 0.46 | 0.75 | 0.03 | 64 | 0.85376 | 10 | 2 |
| 34 | 40.5 | 0.56 | 0.005 | 0.48 | 0.75 | 0.03 | 64 | 0.858143 | 10 | 2 |
| 34 | 40.5 | 0.56 | 0.005 | 0.5 | 0.75 | 0.03 | 64 | 0.863241 | 10 | 2 |
| 34 | 40.5 | 0.56 | 0.005 | 0.52 | 0.75 | 0.03 | 64 | 0.869004 | 10 | 2 |
| 34 | 40.5 | 0.56 | 0.005 | 0.54 | 0.75 | 0.03 | 64 | 0.874994 | 10 | 2 |
| 34 | 40.5 | 0.56 | 0.005 | 0.56 | 0.75 | 0.03 | 64 | 0.880953 | 10 | 2 |
| 34 | 40.5 | 0.56 | 0.005 | 0.58 | 0.75 | 0.03 | 64 | 0.885524 | 10 | 2 |
| 34 | 40.5 | 0.56 | 0.005 | 0.6 | 0.75 | 0.03 | 64 | 0.882234 | 10 | 2 |
| 34 | 40.5 | 0.56 | 0.005 | 0.62 | 0.75 | 0.03 | 64 | 0.871531 | 10 | 2 |
| 34 | 40.5 | 0.56 | 0.005 | 0.64 | 0.75 | 0.03 | 64 | 0.858103 | 10 | 2 |
| 34 | 40.5 | 0.56 | 0.005 | 0.66 | 0.75 | 0.03 | 64 | 0.84354 | 10 | 2 |
| 34 | 40.5 | 0.56 | 0.005 | 0.68 | 0.75 | 0.03 | 64 | 0.830189 | 10 | 2 |
| 34 | 40.5 | 0.56 | 0.005 | 0.7 | 0.75 | 0.03 | 64 | 0.825651 | 10 | 2 |
| 34 | 40.5 | 0.56 | 0.005 | 0.72 | 0.75 | 0.03 | 64 | 0.826947 | 10 | 2 |
| 34 | 40.5 | 0.56 | 0.005 | 0.74 | 0.75 | 0.03 | 64 | 0.827076 | 10 | 2 |

Fig. 10A

| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
|---|---|---|---|---|---|---|---|---|---|---|
| 34 | 38 | 0.52 | 0.005 | 0.5 | 0.75 | 0.03 | 64 | 5.493277 | 10 | 4 |
| 34 | 38.25 | 0.52 | 0.005 | 0.5 | 0.75 | 0.03 | 64 | 5.805845 | 10 | 4 |
| 34 | 38.5 | 0.52 | 0.005 | 0.5 | 0.75 | 0.03 | 64 | 5.942586 | 10 | 4 |
| 34 | 38.75 | 0.52 | 0.005 | 0.5 | 0.75 | 0.03 | 64 | 5.73637 | 10 | 4 |
| 34 | 39 | 0.52 | 0.005 | 0.5 | 0.75 | 0.03 | 64 | 5.420115 | 10 | 4 |
| 34 | 39.25 | 0.52 | 0.005 | 0.5 | 0.75 | 0.03 | 64 | 5.73459 | 10 | 4 |
| 34 | 39.5 | 0.52 | 0.005 | 0.5 | 0.75 | 0.03 | 64 | 5.727515 | 10 | 4 |
| 34 | 39.75 | 0.52 | 0.005 | 0.5 | 0.75 | 0.03 | 64 | 5.530222 | 10 | 4 |
| 34 | 40 | 0.52 | 0.005 | 0.5 | 0.75 | 0.03 | 64 | 5.438755 | 10 | 4 |
| 34 | 40.25 | 0.52 | 0.005 | 0.5 | 0.75 | 0.03 | 64 | 5.609786 | 10 | 4 |
| 34 | 40.5 | 0.52 | 0.005 | 0.5 | 0.75 | 0.03 | 64 | 5.719851 | 10 | 4 |
| 34 | 40.75 | 0.52 | 0.005 | 0.5 | 0.75 | 0.03 | 64 | 5.513499 | 10 | 4 |
| 34 | 41 | 0.52 | 0.005 | 0.5 | 0.75 | 0.03 | 64 | 5.717267 | 10 | 4 |
| 34 | 41.25 | 0.52 | 0.005 | 0.5 | 0.75 | 0.03 | 64 | 5.499554 | 10 | 4 |
| 34 | 41.5 | 0.52 | 0.005 | 0.5 | 0.75 | 0.03 | 64 | 5.133205 | 10 | 4 |
| 34 | 41.75 | 0.52 | 0.005 | 0.5 | 0.75 | 0.03 | 64 | 4.903186 | 10 | 4 |
| 34 | 42 | 0.52 | 0.005 | 0.5 | 0.75 | 0.03 | 64 | 4.680863 | 10 | 4 |
| 34 | 42.25 | 0.52 | 0.005 | 0.5 | 0.75 | 0.03 | 64 | 4.548648 | 10 | 4 |
| 34 | 42.5 | 0.52 | 0.005 | 0.5 | 0.75 | 0.03 | 64 | 4.545021 | 10 | 4 |
| 34 | 42.75 | 0.52 | 0.005 | 0.5 | 0.75 | 0.03 | 64 | 4.067325 | 10 | 4 |
| 34 | 43 | 0.52 | 0.005 | 0.5 | 0.75 | 0.03 | 64 | 3.921024 | 10 | 4 |
| 34 | 38 | 0.53 | 0.005 | 0.5 | 0.75 | 0.03 | 64 | 5.717495 | 10 | 4 |
| 34 | 38.25 | 0.53 | 0.005 | 0.5 | 0.75 | 0.03 | 64 | 5.810591 | 10 | 4 |
| 34 | 38.5 | 0.53 | 0.005 | 0.5 | 0.75 | 0.03 | 64 | 5.926244 | 10 | 4 |
| 34 | 38.75 | 0.53 | 0.005 | 0.5 | 0.75 | 0.03 | 64 | 5.767832 | 10 | 4 |
| 34 | 39 | 0.53 | 0.005 | 0.5 | 0.75 | 0.03 | 64 | 5.419467 | 10 | 4 |
| 34 | 39.25 | 0.53 | 0.005 | 0.5 | 0.75 | 0.03 | 64 | 5.689173 | 10 | 4 |
| 34 | 39.5 | 0.53 | 0.005 | 0.5 | 0.75 | 0.03 | 64 | 5.611356 | 10 | 4 |
| 34 | 39.75 | 0.53 | 0.005 | 0.5 | 0.75 | 0.03 | 64 | 5.348584 | 10 | 4 |
| 34 | 40 | 0.53 | 0.005 | 0.5 | 0.75 | 0.03 | 64 | 5.371505 | 10 | 4 |
| 34 | 40.25 | 0.53 | 0.005 | 0.5 | 0.75 | 0.03 | 64 | 5.571745 | 10 | 4 |
| 34 | 40.5 | 0.53 | 0.005 | 0.5 | 0.75 | 0.03 | 64 | 5.667448 | 10 | 4 |
| 34 | 40.75 | 0.53 | 0.005 | 0.5 | 0.75 | 0.03 | 64 | 5.597261 | 10 | 4 |
| 34 | 41 | 0.53 | 0.005 | 0.5 | 0.75 | 0.03 | 64 | 5.578154 | 10 | 4 |
| 34 | 41.25 | 0.53 | 0.005 | 0.5 | 0.75 | 0.03 | 64 | 5.412163 | 10 | 4 |
| 34 | 41.5 | 0.53 | 0.005 | 0.5 | 0.75 | 0.03 | 64 | 5.049304 | 10 | 4 |
| 34 | 41.75 | 0.53 | 0.005 | 0.5 | 0.75 | 0.03 | 64 | 4.730424 | 10 | 4 |
| 34 | 42 | 0.53 | 0.005 | 0.5 | 0.75 | 0.03 | 64 | 4.570047 | 10 | 4 |
| 34 | 42.25 | 0.53 | 0.005 | 0.5 | 0.75 | 0.03 | 64 | 4.523695 | 10 | 4 |
| 34 | 42.5 | 0.53 | 0.005 | 0.5 | 0.75 | 0.03 | 64 | 4.477343 | 10 | 4 |
| 34 | 42.75 | 0.53 | 0.005 | 0.5 | 0.75 | 0.03 | 64 | 4.037887 | 10 | 4 |
| 34 | 43 | 0.53 | 0.005 | 0.5 | 0.75 | 0.03 | 64 | 3.877986 | 10 | 4 |
| 34 | 38 | 0.54 | 0.005 | 0.5 | 0.75 | 0.03 | 64 | 5.622371 | 10 | 4 |
| 34 | 38.25 | 0.54 | 0.005 | 0.5 | 0.75 | 0.03 | 64 | 5.678961 | 10 | 4 |
| 34 | 38.5 | 0.54 | 0.005 | 0.5 | 0.75 | 0.03 | 64 | 5.899668 | 10 | 4 |
| 34 | 38.75 | 0.54 | 0.005 | 0.5 | 0.75 | 0.03 | 64 | 5.757424 | 10 | 4 |
| 34 | 39 | 0.54 | 0.005 | 0.5 | 0.75 | 0.03 | 64 | 5.423527 | 10 | 4 |
| 34 | 39.25 | 0.54 | 0.005 | 0.5 | 0.75 | 0.03 | 64 | 5.53263 | 10 | 4 |
| 34 | 39.5 | 0.54 | 0.005 | 0.5 | 0.75 | 0.03 | 64 | 5.568131 | 10 | 4 |
| 34 | 39.75 | 0.54 | 0.005 | 0.5 | 0.75 | 0.03 | 64 | 5.343607 | 10 | 4 |
| 34 | 40 | 0.54 | 0.005 | 0.5 | 0.75 | 0.03 | 64 | 5.178168 | 10 | 4 |
| 34 | 40.25 | 0.54 | 0.005 | 0.5 | 0.75 | 0.03 | 64 | 5.312555 | 10 | 4 |
| 34 | 40.5 | 0.54 | 0.005 | 0.5 | 0.75 | 0.03 | 64 | 5.599147 | 10 | 4 |
| 34 | 40.75 | 0.54 | 0.005 | 0.5 | 0.75 | 0.03 | 64 | 5.426709 | 10 | 4 |
| 34 | 41 | 0.54 | 0.005 | 0.5 | 0.75 | 0.03 | 64 | 5.405064 | 10 | 4 |
| 34 | 41.25 | 0.54 | 0.005 | 0.5 | 0.75 | 0.03 | 64 | 5.213119 | 10 | 4 |

Fig. 10B

| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
|---|---|---|---|---|---|---|---|---|---|---|
| 34 | 41.5 | 0.54 | 0.005 | 0.5 | 0.75 | 0.03 | 64 | 5.003045 | 10 | 4 |
| 34 | 41.75 | 0.54 | 0.005 | 0.5 | 0.75 | 0.03 | 64 | 4.623531 | 10 | 4 |
| 34 | 42 | 0.54 | 0.005 | 0.5 | 0.75 | 0.03 | 64 | 4.533406 | 10 | 4 |
| 34 | 42.25 | 0.54 | 0.005 | 0.5 | 0.75 | 0.03 | 64 | 4.463817 | 10 | 4 |
| 34 | 42.5 | 0.54 | 0.005 | 0.5 | 0.75 | 0.03 | 64 | 4.334422 | 10 | 4 |
| 34 | 42.75 | 0.54 | 0.005 | 0.5 | 0.75 | 0.03 | 64 | 4.030265 | 10 | 4 |
| 34 | 43 | 0.54 | 0.005 | 0.5 | 0.75 | 0.03 | 64 | 3.937283 | 10 | 4 |
| 34 | 38 | 0.55 | 0.005 | 0.5 | 0.75 | 0.03 | 64 | 5.424596 | 10 | 4 |
| 34 | 38.25 | 0.55 | 0.005 | 0.5 | 0.75 | 0.03 | 64 | 5.596816 | 10 | 4 |
| 34 | 38.5 | 0.55 | 0.005 | 0.5 | 0.75 | 0.03 | 64 | 5.822916 | 10 | 4 |
| 34 | 38.75 | 0.55 | 0.005 | 0.5 | 0.75 | 0.03 | 64 | 5.775823 | 10 | 4 |
| 34 | 39 | 0.55 | 0.005 | 0.5 | 0.75 | 0.03 | 64 | 5.481692 | 10 | 4 |
| 34 | 39.25 | 0.55 | 0.005 | 0.5 | 0.75 | 0.03 | 64 | 5.450962 | 10 | 4 |
| 34 | 39.5 | 0.55 | 0.005 | 0.5 | 0.75 | 0.03 | 64 | 5.513478 | 10 | 4 |
| 34 | 39.75 | 0.55 | 0.005 | 0.5 | 0.75 | 0.03 | 64 | 5.417895 | 10 | 4 |
| 34 | 40 | 0.55 | 0.005 | 0.5 | 0.75 | 0.03 | 64 | 5.030628 | 10 | 4 |
| 34 | 40.25 | 0.55 | 0.005 | 0.5 | 0.75 | 0.03 | 64 | 5.182121 | 10 | 4 |
| 34 | 40.5 | 0.55 | 0.005 | 0.5 | 0.75 | 0.03 | 64 | 5.428893 | 10 | 4 |
| 34 | 40.75 | 0.55 | 0.005 | 0.5 | 0.75 | 0.03 | 64 | 5.329691 | 10 | 4 |
| 34 | 41 | 0.55 | 0.005 | 0.5 | 0.75 | 0.03 | 64 | 5.289889 | 10 | 4 |
| 34 | 41.25 | 0.55 | 0.005 | 0.5 | 0.75 | 0.03 | 64 | 5.129013 | 10 | 4 |
| 34 | 41.5 | 0.55 | 0.005 | 0.5 | 0.75 | 0.03 | 64 | 4.885418 | 10 | 4 |
| 34 | 41.75 | 0.55 | 0.005 | 0.5 | 0.75 | 0.03 | 64 | 4.483177 | 10 | 4 |
| 34 | 42 | 0.55 | 0.005 | 0.5 | 0.75 | 0.03 | 64 | 4.452805 | 10 | 4 |
| 34 | 42.25 | 0.55 | 0.005 | 0.5 | 0.75 | 0.03 | 64 | 4.434488 | 10 | 4 |
| 34 | 42.5 | 0.55 | 0.005 | 0.5 | 0.75 | 0.03 | 64 | 4.301845 | 10 | 4 |
| 34 | 42.75 | 0.55 | 0.005 | 0.5 | 0.75 | 0.03 | 64 | 3.988017 | 10 | 4 |
| 34 | 43 | 0.55 | 0.005 | 0.5 | 0.75 | 0.03 | 64 | 3.892357 | 10 | 4 |
| 34 | 38 | 0.56 | 0.005 | 0.5 | 0.75 | 0.03 | 64 | 5.229829 | 10 | 4 |
| 34 | 38.25 | 0.56 | 0.005 | 0.5 | 0.75 | 0.03 | 64 | 5.453779 | 10 | 4 |
| 34 | 38.5 | 0.56 | 0.005 | 0.5 | 0.75 | 0.03 | 64 | 5.638591 | 10 | 4 |
| 34 | 38.75 | 0.56 | 0.005 | 0.5 | 0.75 | 0.03 | 64 | 5.765021 | 10 | 4 |
| 34 | 39 | 0.56 | 0.005 | 0.5 | 0.75 | 0.03 | 64 | 5.596684 | 10 | 4 |
| 34 | 39.25 | 0.56 | 0.005 | 0.5 | 0.75 | 0.03 | 64 | 5.353917 | 10 | 4 |
| 34 | 39.5 | 0.56 | 0.005 | 0.5 | 0.75 | 0.03 | 64 | 5.401111 | 10 | 4 |
| 34 | 39.75 | 0.56 | 0.005 | 0.5 | 0.75 | 0.03 | 64 | 5.414612 | 10 | 4 |
| 34 | 40 | 0.56 | 0.005 | 0.5 | 0.75 | 0.03 | 64 | 5.133628 | 10 | 4 |
| 34 | 40.25 | 0.56 | 0.005 | 0.5 | 0.75 | 0.03 | 64 | 5.105611 | 10 | 4 |
| 34 | 40.5 | 0.56 | 0.005 | 0.5 | 0.75 | 0.03 | 64 | 5.266954 | 10 | 4 |
| 34 | 40.75 | 0.56 | 0.005 | 0.5 | 0.75 | 0.03 | 64 | 5.197605 | 10 | 4 |
| 34 | 41 | 0.56 | 0.005 | 0.5 | 0.75 | 0.03 | 64 | 5.132326 | 10 | 4 |
| 34 | 41.25 | 0.56 | 0.005 | 0.5 | 0.75 | 0.03 | 64 | 5.000269 | 10 | 4 |
| 34 | 41.5 | 0.56 | 0.005 | 0.5 | 0.75 | 0.03 | 64 | 4.728625 | 10 | 4 |
| 34 | 41.75 | 0.56 | 0.005 | 0.5 | 0.75 | 0.03 | 64 | 4.471355 | 10 | 4 |
| 34 | 42 | 0.56 | 0.005 | 0.5 | 0.75 | 0.03 | 64 | 4.42342 | 10 | 4 |
| 34 | 42.25 | 0.56 | 0.005 | 0.5 | 0.75 | 0.03 | 64 | 4.461586 | 10 | 4 |
| 34 | 42.5 | 0.56 | 0.005 | 0.5 | 0.75 | 0.03 | 64 | 4.302394 | 10 | 4 |
| 34 | 42.75 | 0.56 | 0.005 | 0.5 | 0.75 | 0.03 | 64 | 3.9399 | 10 | 4 |
| 34 | 43 | 0.56 | 0.005 | 0.5 | 0.75 | 0.03 | 64 | 3.803905 | 10 | 4 |
| 34 | 38 | 0.57 | 0.005 | 0.5 | 0.75 | 0.03 | 64 | 4.93232 | 10 | 4 |
| 34 | 38.25 | 0.57 | 0.005 | 0.5 | 0.75 | 0.03 | 64 | 5.206947 | 10 | 4 |
| 34 | 38.5 | 0.57 | 0.005 | 0.5 | 0.75 | 0.03 | 64 | 5.572394 | 10 | 4 |
| 34 | 38.75 | 0.57 | 0.005 | 0.5 | 0.75 | 0.03 | 64 | 5.652302 | 10 | 4 |
| 34 | 39 | 0.57 | 0.005 | 0.5 | 0.75 | 0.03 | 64 | 5.555333 | 10 | 4 |
| 34 | 39.25 | 0.57 | 0.005 | 0.5 | 0.75 | 0.03 | 64 | 5.316009 | 10 | 4 |
| 34 | 39.5 | 0.57 | 0.005 | 0.5 | 0.75 | 0.03 | 64 | 5.300094 | 10 | 4 |
| 34 | 39.75 | 0.57 | 0.005 | 0.5 | 0.75 | 0.03 | 64 | 5.397194 | 10 | 4 |

Fig. 10C

| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
|---|---|---|---|---|---|---|---|---|---|---|
| 34 | 40 | 0.57 | 0.005 | 0.5 | 0.75 | 0.03 | 64 | 5.075396 | 10 | 4 |
| 34 | 40.25 | 0.57 | 0.005 | 0.5 | 0.75 | 0.03 | 64 | 4.959463 | 10 | 4 |
| 34 | 40.5 | 0.57 | 0.005 | 0.5 | 0.75 | 0.03 | 64 | 5.037557 | 10 | 4 |
| 34 | 40.75 | 0.57 | 0.005 | 0.5 | 0.75 | 0.03 | 64 | 5.096533 | 10 | 4 |
| 34 | 41 | 0.57 | 0.005 | 0.5 | 0.75 | 0.03 | 64 | 5.018315 | 10 | 4 |
| 34 | 41.25 | 0.57 | 0.005 | 0.5 | 0.75 | 0.03 | 64 | 4.968305 | 10 | 4 |
| 34 | 41.5 | 0.57 | 0.005 | 0.5 | 0.75 | 0.03 | 64 | 4.764407 | 10 | 4 |
| 34 | 41.75 | 0.57 | 0.005 | 0.5 | 0.75 | 0.03 | 64 | 4.485349 | 10 | 4 |
| 34 | 42 | 0.57 | 0.005 | 0.5 | 0.75 | 0.03 | 64 | 4.321794 | 10 | 4 |
| 34 | 42.25 | 0.57 | 0.005 | 0.5 | 0.75 | 0.03 | 64 | 4.463833 | 10 | 4 |
| 34 | 42.5 | 0.57 | 0.005 | 0.5 | 0.75 | 0.03 | 64 | 4.288975 | 10 | 4 |
| 34 | 42.75 | 0.57 | 0.005 | 0.5 | 0.75 | 0.03 | 64 | 3.89191 | 10 | 4 |
| 34 | 43 | 0.57 | 0.005 | 0.5 | 0.75 | 0.03 | 64 | 3.668917 | 10 | 4 |
| 34 | 38 | 0.58 | 0.005 | 0.5 | 0.75 | 0.03 | 64 | 4.89769 | 10 | 4 |
| 34 | 38.25 | 0.58 | 0.005 | 0.5 | 0.75 | 0.03 | 64 | 4.905187 | 10 | 4 |
| 34 | 38.5 | 0.58 | 0.005 | 0.5 | 0.75 | 0.03 | 64 | 5.405338 | 10 | 4 |
| 34 | 38.75 | 0.58 | 0.005 | 0.5 | 0.75 | 0.03 | 64 | 5.604507 | 10 | 4 |
| 34 | 39 | 0.58 | 0.005 | 0.5 | 0.75 | 0.03 | 64 | 5.424502 | 10 | 4 |
| 34 | 39.25 | 0.58 | 0.005 | 0.5 | 0.75 | 0.03 | 64 | 5.229388 | 10 | 4 |
| 34 | 39.5 | 0.58 | 0.005 | 0.5 | 0.75 | 0.03 | 64 | 5.147347 | 10 | 4 |
| 34 | 39.75 | 0.58 | 0.005 | 0.5 | 0.75 | 0.03 | 64 | 5.314294 | 10 | 4 |
| 34 | 40 | 0.58 | 0.005 | 0.5 | 0.75 | 0.03 | 64 | 5.018439 | 10 | 4 |
| 34 | 40.25 | 0.58 | 0.005 | 0.5 | 0.75 | 0.03 | 64 | 4.792406 | 10 | 4 |
| 34 | 40.5 | 0.58 | 0.005 | 0.5 | 0.75 | 0.03 | 64 | 4.934068 | 10 | 4 |
| 34 | 40.75 | 0.58 | 0.005 | 0.5 | 0.75 | 0.03 | 64 | 5.085083 | 10 | 4 |
| 34 | 41 | 0.58 | 0.005 | 0.5 | 0.75 | 0.03 | 64 | 5.018061 | 10 | 4 |
| 34 | 41.25 | 0.58 | 0.005 | 0.5 | 0.75 | 0.03 | 64 | 4.944051 | 10 | 4 |
| 34 | 41.5 | 0.58 | 0.005 | 0.5 | 0.75 | 0.03 | 64 | 4.762533 | 10 | 4 |
| 34 | 41.75 | 0.58 | 0.005 | 0.5 | 0.75 | 0.03 | 64 | 4.439249 | 10 | 4 |
| 34 | 42 | 0.58 | 0.005 | 0.5 | 0.75 | 0.03 | 64 | 4.266388 | 10 | 4 |
| 34 | 42.25 | 0.58 | 0.005 | 0.5 | 0.75 | 0.03 | 64 | 4.453432 | 10 | 4 |
| 34 | 42.5 | 0.58 | 0.005 | 0.5 | 0.75 | 0.03 | 64 | 4.314914 | 10 | 4 |
| 34 | 42.75 | 0.58 | 0.005 | 0.5 | 0.75 | 0.03 | 64 | 3.875559 | 10 | 4 |
| 34 | 43 | 0.58 | 0.005 | 0.5 | 0.75 | 0.03 | 64 | 3.538107 | 10 | 4 |
| 34 | 38 | 0.59 | 0.005 | 0.5 | 0.75 | 0.03 | 64 | 4.842274 | 10 | 4 |
| 34 | 38.25 | 0.59 | 0.005 | 0.5 | 0.75 | 0.03 | 64 | 4.754307 | 10 | 4 |
| 34 | 38.5 | 0.59 | 0.005 | 0.5 | 0.75 | 0.03 | 64 | 5.221967 | 10 | 4 |
| 34 | 38.75 | 0.59 | 0.005 | 0.5 | 0.75 | 0.03 | 64 | 5.33594 | 10 | 4 |
| 34 | 39 | 0.59 | 0.005 | 0.5 | 0.75 | 0.03 | 64 | 5.314924 | 10 | 4 |
| 34 | 39.25 | 0.59 | 0.005 | 0.5 | 0.75 | 0.03 | 64 | 5.222291 | 10 | 4 |
| 34 | 39.5 | 0.59 | 0.005 | 0.5 | 0.75 | 0.03 | 64 | 5.142299 | 10 | 4 |
| 34 | 39.75 | 0.59 | 0.005 | 0.5 | 0.75 | 0.03 | 64 | 5.242247 | 10 | 4 |
| 34 | 40 | 0.59 | 0.005 | 0.5 | 0.75 | 0.03 | 64 | 5.068558 | 10 | 4 |
| 34 | 40.25 | 0.59 | 0.005 | 0.5 | 0.75 | 0.03 | 64 | 4.801819 | 10 | 4 |
| 34 | 40.5 | 0.59 | 0.005 | 0.5 | 0.75 | 0.03 | 64 | 4.934716 | 10 | 4 |
| 34 | 40.75 | 0.59 | 0.005 | 0.5 | 0.75 | 0.03 | 64 | 5.041384 | 10 | 4 |
| 34 | 41 | 0.59 | 0.005 | 0.5 | 0.75 | 0.03 | 64 | 4.98427 | 10 | 4 |
| 34 | 41.25 | 0.59 | 0.005 | 0.5 | 0.75 | 0.03 | 64 | 4.963404 | 10 | 4 |
| 34 | 41.5 | 0.59 | 0.005 | 0.5 | 0.75 | 0.03 | 64 | 4.643272 | 10 | 4 |
| 34 | 41.75 | 0.59 | 0.005 | 0.5 | 0.75 | 0.03 | 64 | 4.387925 | 10 | 4 |
| 34 | 42 | 0.59 | 0.005 | 0.5 | 0.75 | 0.03 | 64 | 4.273769 | 10 | 4 |
| 34 | 42.25 | 0.59 | 0.005 | 0.5 | 0.75 | 0.03 | 64 | 4.367913 | 10 | 4 |
| 34 | 42.5 | 0.59 | 0.005 | 0.5 | 0.75 | 0.03 | 64 | 4.212573 | 10 | 4 |
| 34 | 42.75 | 0.59 | 0.005 | 0.5 | 0.75 | 0.03 | 64 | 3.891038 | 10 | 4 |
| 34 | 43 | 0.59 | 0.005 | 0.5 | 0.75 | 0.03 | 64 | 3.563555 | 10 | 4 |
| 34 | 38 | 0.6 | 0.005 | 0.5 | 0.75 | 0.03 | 64 | 4.673238 | 10 | 4 |
| 34 | 38.25 | 0.6 | 0.005 | 0.5 | 0.75 | 0.03 | 64 | 4.599346 | 10 | 4 |

Fig. 10D

| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
|---|---|---|---|---|---|---|---|---|---|---|
| 34 | 38.5 | 0.6 | 0.005 | 0.5 | 0.75 | 0.03 | 64 | 5.071326 | 10 | 4 |
| 34 | 38.75 | 0.6 | 0.005 | 0.5 | 0.75 | 0.03 | 64 | 5.183723 | 10 | 4 |
| 34 | 39 | 0.6 | 0.005 | 0.5 | 0.75 | 0.03 | 64 | 5.199297 | 10 | 4 |
| 34 | 39.25 | 0.6 | 0.005 | 0.5 | 0.75 | 0.03 | 64 | 5.275915 | 10 | 4 |
| 34 | 39.5 | 0.6 | 0.005 | 0.5 | 0.75 | 0.03 | 64 | 5.193584 | 10 | 4 |
| 34 | 39.75 | 0.6 | 0.005 | 0.5 | 0.75 | 0.03 | 64 | 5.247627 | 10 | 4 |
| 34 | 40 | 0.6 | 0.005 | 0.5 | 0.75 | 0.03 | 64 | 5.072312 | 10 | 4 |
| 34 | 40.25 | 0.6 | 0.005 | 0.5 | 0.75 | 0.03 | 64 | 4.781289 | 10 | 4 |
| 34 | 40.5 | 0.6 | 0.005 | 0.5 | 0.75 | 0.03 | 64 | 4.923382 | 10 | 4 |
| 34 | 40.75 | 0.6 | 0.005 | 0.5 | 0.75 | 0.03 | 64 | 4.944674 | 10 | 4 |
| 34 | 41 | 0.6 | 0.005 | 0.5 | 0.75 | 0.03 | 64 | 4.937654 | 10 | 4 |
| 34 | 41.25 | 0.6 | 0.005 | 0.5 | 0.75 | 0.03 | 64 | 4.927164 | 10 | 4 |
| 34 | 41.5 | 0.6 | 0.005 | 0.5 | 0.75 | 0.03 | 64 | 4.719866 | 10 | 4 |
| 34 | 41.75 | 0.6 | 0.005 | 0.5 | 0.75 | 0.03 | 64 | 4.510105 | 10 | 4 |
| 34 | 42 | 0.6 | 0.005 | 0.5 | 0.75 | 0.03 | 64 | 4.272734 | 10 | 4 |
| 34 | 42.25 | 0.6 | 0.005 | 0.5 | 0.75 | 0.03 | 64 | 4.187286 | 10 | 4 |
| 34 | 42.5 | 0.6 | 0.005 | 0.5 | 0.75 | 0.03 | 64 | 4.043926 | 10 | 4 |
| 34 | 42.75 | 0.6 | 0.005 | 0.5 | 0.75 | 0.03 | 64 | 3.776883 | 10 | 4 |
| 34 | 43 | 0.6 | 0.005 | 0.5 | 0.75 | 0.03 | 64 | 3.517216 | 10 | 4 |
| 34 | 38 | 0.61 | 0.005 | 0.5 | 0.75 | 0.03 | 64 | 4.572618 | 10 | 4 |
| 34 | 38.25 | 0.61 | 0.005 | 0.5 | 0.75 | 0.03 | 64 | 4.673075 | 10 | 4 |
| 34 | 38.5 | 0.61 | 0.005 | 0.5 | 0.75 | 0.03 | 64 | 4.964236 | 10 | 4 |
| 34 | 38.75 | 0.61 | 0.005 | 0.5 | 0.75 | 0.03 | 64 | 5.096562 | 10 | 4 |
| 34 | 39 | 0.61 | 0.005 | 0.5 | 0.75 | 0.03 | 64 | 5.010287 | 10 | 4 |
| 34 | 39.25 | 0.61 | 0.005 | 0.5 | 0.75 | 0.03 | 64 | 5.289823 | 10 | 4 |
| 34 | 39.5 | 0.61 | 0.005 | 0.5 | 0.75 | 0.03 | 64 | 5.250743 | 10 | 4 |
| 34 | 39.75 | 0.61 | 0.005 | 0.5 | 0.75 | 0.03 | 64 | 5.196805 | 10 | 4 |
| 34 | 40 | 0.61 | 0.005 | 0.5 | 0.75 | 0.03 | 64 | 5.017651 | 10 | 4 |
| 34 | 40.25 | 0.61 | 0.005 | 0.5 | 0.75 | 0.03 | 64 | 4.822792 | 10 | 4 |
| 34 | 40.5 | 0.61 | 0.005 | 0.5 | 0.75 | 0.03 | 64 | 4.922016 | 10 | 4 |
| 34 | 40.75 | 0.61 | 0.005 | 0.5 | 0.75 | 0.03 | 64 | 4.878578 | 10 | 4 |
| 34 | 41 | 0.61 | 0.005 | 0.5 | 0.75 | 0.03 | 64 | 4.981758 | 10 | 4 |
| 34 | 41.25 | 0.61 | 0.005 | 0.5 | 0.75 | 0.03 | 64 | 4.88136 | 10 | 4 |
| 34 | 41.5 | 0.61 | 0.005 | 0.5 | 0.75 | 0.03 | 64 | 4.704769 | 10 | 4 |
| 34 | 41.75 | 0.61 | 0.005 | 0.5 | 0.75 | 0.03 | 64 | 4.559749 | 10 | 4 |
| 34 | 42 | 0.61 | 0.005 | 0.5 | 0.75 | 0.03 | 64 | 4.312059 | 10 | 4 |
| 34 | 42.25 | 0.61 | 0.005 | 0.5 | 0.75 | 0.03 | 64 | 4.041883 | 10 | 4 |
| 34 | 42.5 | 0.61 | 0.005 | 0.5 | 0.75 | 0.03 | 64 | 3.906976 | 10 | 4 |
| 34 | 42.75 | 0.61 | 0.005 | 0.5 | 0.75 | 0.03 | 64 | 3.607952 | 10 | 4 |
| 34 | 43 | 0.61 | 0.005 | 0.5 | 0.75 | 0.03 | 64 | 3.397672 | 10 | 4 |
| 34 | 38 | 0.62 | 0.005 | 0.5 | 0.75 | 0.03 | 64 | 4.431196 | 10 | 4 |
| 34 | 38.25 | 0.62 | 0.005 | 0.5 | 0.75 | 0.03 | 64 | 4.711157 | 10 | 4 |
| 34 | 38.5 | 0.62 | 0.005 | 0.5 | 0.75 | 0.03 | 64 | 4.79142 | 10 | 4 |
| 34 | 38.75 | 0.62 | 0.005 | 0.5 | 0.75 | 0.03 | 64 | 5.107477 | 10 | 4 |
| 34 | 39 | 0.62 | 0.005 | 0.5 | 0.75 | 0.03 | 64 | 4.948804 | 10 | 4 |
| 34 | 39.25 | 0.62 | 0.005 | 0.5 | 0.75 | 0.03 | 64 | 5.242472 | 10 | 4 |
| 34 | 39.5 | 0.62 | 0.005 | 0.5 | 0.75 | 0.03 | 64 | 5.308088 | 10 | 4 |
| 34 | 39.75 | 0.62 | 0.005 | 0.5 | 0.75 | 0.03 | 64 | 5.208467 | 10 | 4 |
| 34 | 40 | 0.62 | 0.005 | 0.5 | 0.75 | 0.03 | 64 | 4.939575 | 10 | 4 |
| 34 | 40.25 | 0.62 | 0.005 | 0.5 | 0.75 | 0.03 | 64 | 4.79219 | 10 | 4 |
| 34 | 40.5 | 0.62 | 0.005 | 0.5 | 0.75 | 0.03 | 64 | 4.819245 | 10 | 4 |
| 34 | 40.75 | 0.62 | 0.005 | 0.5 | 0.75 | 0.03 | 64 | 4.834752 | 10 | 4 |
| 34 | 41 | 0.62 | 0.005 | 0.5 | 0.75 | 0.03 | 64 | 4.86977 | 10 | 4 |
| 34 | 41.25 | 0.62 | 0.005 | 0.5 | 0.75 | 0.03 | 64 | 4.779608 | 10 | 4 |
| 34 | 41.5 | 0.62 | 0.005 | 0.5 | 0.75 | 0.03 | 64 | 4.717905 | 10 | 4 |
| 34 | 41.75 | 0.62 | 0.005 | 0.5 | 0.75 | 0.03 | 64 | 4.5101 | 10 | 4 |
| 34 | 42 | 0.62 | 0.005 | 0.5 | 0.75 | 0.03 | 64 | 4.294812 | 10 | 4 |

Fig. 10E

| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
|---|---|---|---|---|---|---|---|---|---|---|
| 34 | 42.25 | 0.62 | 0.005 | 0.5 | 0.75 | 0.03 | 64 | 4.041671 | 10 | 4 |
| 34 | 42.5 | 0.62 | 0.005 | 0.5 | 0.75 | 0.03 | 64 | 3.845437 | 10 | 4 |
| 34 | 42.75 | 0.62 | 0.005 | 0.5 | 0.75 | 0.03 | 64 | 3.488905 | 10 | 4 |
| 34 | 43 | 0.62 | 0.005 | 0.5 | 0.75 | 0.03 | 64 | 3.245714 | 10 | 4 |
| 34 | 38 | 0.63 | 0.005 | 0.5 | 0.75 | 0.03 | 64 | 4.444624 | 10 | 4 |
| 34 | 38.25 | 0.63 | 0.005 | 0.5 | 0.75 | 0.03 | 64 | 4.707872 | 10 | 4 |
| 34 | 38.5 | 0.63 | 0.005 | 0.5 | 0.75 | 0.03 | 64 | 4.712884 | 10 | 4 |
| 34 | 38.75 | 0.63 | 0.005 | 0.5 | 0.75 | 0.03 | 64 | 4.997234 | 10 | 4 |
| 34 | 39 | 0.63 | 0.005 | 0.5 | 0.75 | 0.03 | 64 | 4.976386 | 10 | 4 |
| 34 | 39.25 | 0.63 | 0.005 | 0.5 | 0.75 | 0.03 | 64 | 5.241674 | 10 | 4 |
| 34 | 39.5 | 0.63 | 0.005 | 0.5 | 0.75 | 0.03 | 64 | 5.337666 | 10 | 4 |
| 34 | 39.75 | 0.63 | 0.005 | 0.5 | 0.75 | 0.03 | 64 | 5.1678 | 10 | 4 |
| 34 | 40 | 0.63 | 0.005 | 0.5 | 0.75 | 0.03 | 64 | 4.868893 | 10 | 4 |
| 34 | 40.25 | 0.63 | 0.005 | 0.5 | 0.75 | 0.03 | 64 | 4.738868 | 10 | 4 |
| 34 | 40.5 | 0.63 | 0.005 | 0.5 | 0.75 | 0.03 | 64 | 4.80074 | 10 | 4 |
| 34 | 40.75 | 0.63 | 0.005 | 0.5 | 0.75 | 0.03 | 64 | 4.89628 | 10 | 4 |
| 34 | 41 | 0.63 | 0.005 | 0.5 | 0.75 | 0.03 | 64 | 4.779172 | 10 | 4 |
| 34 | 41.25 | 0.63 | 0.005 | 0.5 | 0.75 | 0.03 | 64 | 4.772348 | 10 | 4 |
| 34 | 41.5 | 0.63 | 0.005 | 0.5 | 0.75 | 0.03 | 64 | 4.665951 | 10 | 4 |
| 34 | 41.75 | 0.63 | 0.005 | 0.5 | 0.75 | 0.03 | 64 | 4.491212 | 10 | 4 |
| 34 | 42 | 0.63 | 0.005 | 0.5 | 0.75 | 0.03 | 64 | 4.2586 | 10 | 4 |
| 34 | 42.25 | 0.63 | 0.005 | 0.5 | 0.75 | 0.03 | 64 | 3.949061 | 10 | 4 |
| 34 | 42.5 | 0.63 | 0.005 | 0.5 | 0.75 | 0.03 | 64 | 3.749323 | 10 | 4 |
| 34 | 42.75 | 0.63 | 0.005 | 0.5 | 0.75 | 0.03 | 64 | 3.367393 | 10 | 4 |
| 34 | 43 | 0.63 | 0.005 | 0.5 | 0.75 | 0.03 | 64 | 3.175437 | 10 | 4 |
| 34 | 38 | 0.64 | 0.005 | 0.5 | 0.75 | 0.03 | 64 | 4.375601 | 10 | 4 |
| 34 | 38.25 | 0.64 | 0.005 | 0.5 | 0.75 | 0.03 | 64 | 4.653965 | 10 | 4 |
| 34 | 38.5 | 0.64 | 0.005 | 0.5 | 0.75 | 0.03 | 64 | 4.851339 | 10 | 4 |
| 34 | 38.75 | 0.64 | 0.005 | 0.5 | 0.75 | 0.03 | 64 | 4.910555 | 10 | 4 |
| 34 | 39 | 0.64 | 0.005 | 0.5 | 0.75 | 0.03 | 64 | 4.890862 | 10 | 4 |
| 34 | 39.25 | 0.64 | 0.005 | 0.5 | 0.75 | 0.03 | 64 | 5.230752 | 10 | 4 |
| 34 | 39.5 | 0.64 | 0.005 | 0.5 | 0.75 | 0.03 | 64 | 5.237599 | 10 | 4 |
| 34 | 39.75 | 0.64 | 0.005 | 0.5 | 0.75 | 0.03 | 64 | 5.154108 | 10 | 4 |
| 34 | 40 | 0.64 | 0.005 | 0.5 | 0.75 | 0.03 | 64 | 4.799762 | 10 | 4 |
| 34 | 40.25 | 0.64 | 0.005 | 0.5 | 0.75 | 0.03 | 64 | 4.806213 | 10 | 4 |
| 34 | 40.5 | 0.64 | 0.005 | 0.5 | 0.75 | 0.03 | 64 | 4.76932 | 10 | 4 |
| 34 | 40.75 | 0.64 | 0.005 | 0.5 | 0.75 | 0.03 | 64 | 4.762513 | 10 | 4 |
| 34 | 41 | 0.64 | 0.005 | 0.5 | 0.75 | 0.03 | 64 | 4.830222 | 10 | 4 |
| 34 | 41.25 | 0.64 | 0.005 | 0.5 | 0.75 | 0.03 | 64 | 4.644581 | 10 | 4 |
| 34 | 41.5 | 0.64 | 0.005 | 0.5 | 0.75 | 0.03 | 64 | 4.584929 | 10 | 4 |
| 34 | 41.75 | 0.64 | 0.005 | 0.5 | 0.75 | 0.03 | 64 | 4.363803 | 10 | 4 |
| 34 | 42 | 0.64 | 0.005 | 0.5 | 0.75 | 0.03 | 64 | 4.284305 | 10 | 4 |
| 34 | 42.25 | 0.64 | 0.005 | 0.5 | 0.75 | 0.03 | 64 | 3.78676 | 10 | 4 |
| 34 | 42.5 | 0.64 | 0.005 | 0.5 | 0.75 | 0.03 | 64 | 3.684077 | 10 | 4 |
| 34 | 42.75 | 0.64 | 0.005 | 0.5 | 0.75 | 0.03 | 64 | 3.192547 | 10 | 4 |
| 34 | 43 | 0.64 | 0.005 | 0.5 | 0.75 | 0.03 | 64 | 3.3293 | 10 | 4 |
| 34 | 38 | 0.65 | 0.005 | 0.5 | 0.75 | 0.03 | 64 | 4.213167 | 10 | 4 |
| 34 | 38.25 | 0.65 | 0.005 | 0.5 | 0.75 | 0.03 | 64 | 4.606747 | 10 | 4 |
| 34 | 38.5 | 0.65 | 0.005 | 0.5 | 0.75 | 0.03 | 64 | 4.887867 | 10 | 4 |
| 34 | 38.75 | 0.65 | 0.005 | 0.5 | 0.75 | 0.03 | 64 | 4.792631 | 10 | 4 |
| 34 | 39 | 0.65 | 0.005 | 0.5 | 0.75 | 0.03 | 64 | 4.895459 | 10 | 4 |
| 34 | 39.25 | 0.65 | 0.005 | 0.5 | 0.75 | 0.03 | 64 | 5.234235 | 10 | 4 |
| 34 | 39.5 | 0.65 | 0.005 | 0.5 | 0.75 | 0.03 | 64 | 5.261138 | 10 | 4 |
| 34 | 39.75 | 0.65 | 0.005 | 0.5 | 0.75 | 0.03 | 64 | 5.383435 | 10 | 4 |
| 34 | 40 | 0.65 | 0.005 | 0.5 | 0.75 | 0.03 | 64 | 4.753519 | 10 | 4 |
| 34 | 40.25 | 0.65 | 0.005 | 0.5 | 0.75 | 0.03 | 64 | 4.761221 | 10 | 4 |
| 34 | 40.5 | 0.65 | 0.005 | 0.5 | 0.75 | 0.03 | 64 | 4.686667 | 10 | 4 |

| Fig. 10F | | | | | | | | | | |
|---|---|---|---|---|---|---|---|---|---|---|
| Crown Angle | Pavillion Angle | Table Size | Culet Size | Star Length | Lower Girdle Length | Girdle Thickness | # of Girdle Facets | DCLR4 | Wavelength Sampling Interval (nm) | Brightness Cutoff Threshold Factor |
| 34 | 40.75 | 0.65 | 0.005 | 0.5 | 0.75 | 0.03 | 64 | 4.722319 | 10 | 4 |
| 34 | 41 | 0.65 | 0.005 | 0.5 | 0.75 | 0.03 | 64 | 4.880547 | 10 | 4 |
| 34 | 41.25 | 0.65 | 0.005 | 0.5 | 0.75 | 0.03 | 64 | 4.640121 | 10 | 4 |
| 34 | 41.5 | 0.65 | 0.005 | 0.5 | 0.75 | 0.03 | 64 | 4.50616 | 10 | 4 |
| 34 | 41.75 | 0.65 | 0.005 | 0.5 | 0.75 | 0.03 | 64 | 4.242882 | 10 | 4 |
| 34 | 42 | 0.65 | 0.005 | 0.5 | 0.75 | 0.03 | 64 | 4.070292 | 10 | 4 |
| 34 | 42.25 | 0.65 | 0.005 | 0.5 | 0.75 | 0.03 | 64 | 3.746429 | 10 | 4 |
| 34 | 42.5 | 0.65 | 0.005 | 0.5 | 0.75 | 0.03 | 64 | 3.579245 | 10 | 4 |
| 34 | 42.75 | 0.65 | 0.005 | 0.5 | 0.75 | 0.03 | 64 | 3.103817 | 10 | 4 |
| 34 | 43 | 0.65 | 0.005 | 0.5 | 0.75 | 0.03 | 64 | 3.192281 | 10 | 4 |

Fig. 11A

| Crown Angle | Pavillion Angle | Table Size | Culet Size | Star Length | Lower Girdle Length | Girdle Thickness | # of Girdle Facets | DCLR3 | Wavelength Sampling Interval (nm) | Brightness Cutoff Threshold Factor |
|---|---|---|---|---|---|---|---|---|---|---|
| 34 | 38 | 0.52 | 0.005 | 0.5 | 0.75 | 0.03 | 64 | 2.56024 | 10 | 3 |
| 34 | 38.25 | 0.52 | 0.005 | 0.5 | 0.75 | 0.03 | 64 | 2.62372 | 10 | 3 |
| 34 | 38.5 | 0.52 | 0.005 | 0.5 | 0.75 | 0.03 | 64 | 2.637903 | 10 | 3 |
| 34 | 38.75 | 0.52 | 0.005 | 0.5 | 0.75 | 0.03 | 64 | 2.45408 | 10 | 3 |
| 34 | 39 | 0.52 | 0.005 | 0.5 | 0.75 | 0.03 | 64 | 2.521807 | 10 | 3 |
| 34 | 39.25 | 0.52 | 0.005 | 0.5 | 0.75 | 0.03 | 64 | 2.628378 | 10 | 3 |
| 34 | 39.5 | 0.52 | 0.005 | 0.5 | 0.75 | 0.03 | 64 | 2.586273 | 10 | 3 |
| 34 | 39.75 | 0.52 | 0.005 | 0.5 | 0.75 | 0.03 | 64 | 2.484274 | 10 | 3 |
| 34 | 40 | 0.52 | 0.005 | 0.5 | 0.75 | 0.03 | 64 | 2.42121 | 10 | 3 |
| 34 | 40.25 | 0.52 | 0.005 | 0.5 | 0.75 | 0.03 | 64 | 2.502591 | 10 | 3 |
| 34 | 40.5 | 0.52 | 0.005 | 0.5 | 0.75 | 0.03 | 64 | 2.497725 | 10 | 3 |
| 34 | 40.75 | 0.52 | 0.005 | 0.5 | 0.75 | 0.03 | 64 | 2.402551 | 10 | 3 |
| 34 | 41 | 0.52 | 0.005 | 0.5 | 0.75 | 0.03 | 64 | 2.495177 | 10 | 3 |
| 34 | 41.25 | 0.52 | 0.005 | 0.5 | 0.75 | 0.03 | 64 | 2.304985 | 10 | 3 |
| 34 | 41.5 | 0.52 | 0.005 | 0.5 | 0.75 | 0.03 | 64 | 2.216605 | 10 | 3 |
| 34 | 41.75 | 0.52 | 0.005 | 0.5 | 0.75 | 0.03 | 64 | 2.168096 | 10 | 3 |
| 34 | 42 | 0.52 | 0.005 | 0.5 | 0.75 | 0.03 | 64 | 2.069741 | 10 | 3 |
| 34 | 42.25 | 0.52 | 0.005 | 0.5 | 0.75 | 0.03 | 64 | 1.949909 | 10 | 3 |
| 34 | 42.5 | 0.52 | 0.005 | 0.5 | 0.75 | 0.03 | 64 | 1.922056 | 10 | 3 |
| 34 | 42.75 | 0.52 | 0.005 | 0.5 | 0.75 | 0.03 | 64 | 1.772726 | 10 | 3 |
| 34 | 43 | 0.52 | 0.005 | 0.5 | 0.75 | 0.03 | 64 | 1.751846 | 10 | 3 |
| 34 | 38 | 0.53 | 0.005 | 0.5 | 0.75 | 0.03 | 64 | 2.585623 | 10 | 3 |
| 34 | 38.25 | 0.53 | 0.005 | 0.5 | 0.75 | 0.03 | 64 | 2.631226 | 10 | 3 |
| 34 | 38.5 | 0.53 | 0.005 | 0.5 | 0.75 | 0.03 | 64 | 2.607705 | 10 | 3 |
| 34 | 38.75 | 0.53 | 0.005 | 0.5 | 0.75 | 0.03 | 64 | 2.489197 | 10 | 3 |
| 34 | 39 | 0.53 | 0.005 | 0.5 | 0.75 | 0.03 | 64 | 2.505629 | 10 | 3 |
| 34 | 39.25 | 0.53 | 0.005 | 0.5 | 0.75 | 0.03 | 64 | 2.577765 | 10 | 3 |
| 34 | 39.5 | 0.53 | 0.005 | 0.5 | 0.75 | 0.03 | 64 | 2.554002 | 10 | 3 |
| 34 | 39.75 | 0.53 | 0.005 | 0.5 | 0.75 | 0.03 | 64 | 2.451161 | 10 | 3 |
| 34 | 40 | 0.53 | 0.005 | 0.5 | 0.75 | 0.03 | 64 | 2.387227 | 10 | 3 |
| 34 | 40.25 | 0.53 | 0.005 | 0.5 | 0.75 | 0.03 | 64 | 2.465355 | 10 | 3 |
| 34 | 40.5 | 0.53 | 0.005 | 0.5 | 0.75 | 0.03 | 64 | 2.482186 | 10 | 3 |
| 34 | 40.75 | 0.53 | 0.005 | 0.6 | 0.75 | 0.03 | 64 | 2.397814 | 10 | 3 |
| 34 | 41 | 0.53 | 0.005 | 0.5 | 0.75 | 0.03 | 64 | 2.405243 | 10 | 3 |
| 34 | 41.25 | 0.53 | 0.005 | 0.5 | 0.75 | 0.03 | 64 | 2.219772 | 10 | 3 |
| 34 | 41.5 | 0.53 | 0.005 | 0.5 | 0.75 | 0.03 | 64 | 2.159837 | 10 | 3 |
| 34 | 41.75 | 0.53 | 0.005 | 0.5 | 0.75 | 0.03 | 64 | 2.109897 | 10 | 3 |
| 34 | 42 | 0.53 | 0.005 | 0.5 | 0.75 | 0.03 | 64 | 2.01383 | 10 | 3 |
| 34 | 42.25 | 0.53 | 0.005 | 0.5 | 0.75 | 0.03 | 64 | 1.911171 | 10 | 3 |
| 34 | 42.5 | 0.53 | 0.005 | 0.5 | 0.75 | 0.03 | 64 | 1.855773 | 10 | 3 |
| 34 | 42.75 | 0.53 | 0.005 | 0.5 | 0.75 | 0.03 | 64 | 1.709568 | 10 | 3 |
| 34 | 43 | 0.53 | 0.005 | 0.5 | 0.75 | 0.03 | 64 | 1.712729 | 10 | 3 |
| 34 | 38 | 0.54 | 0.005 | 0.5 | 0.75 | 0.03 | 64 | 2.558642 | 10 | 3 |
| 34 | 38.25 | 0.54 | 0.005 | 0.5 | 0.75 | 0.03 | 64 | 2.602757 | 10 | 3 |
| 34 | 38.5 | 0.54 | 0.005 | 0.5 | 0.75 | 0.03 | 64 | 2.572777 | 10 | 3 |
| 34 | 38.75 | 0.54 | 0.005 | 0.5 | 0.75 | 0.03 | 64 | 2.497193 | 10 | 3 |
| 34 | 39 | 0.54 | 0.005 | 0.5 | 0.75 | 0.03 | 64 | 2.485891 | 10 | 3 |
| 34 | 39.25 | 0.54 | 0.005 | 0.5 | 0.75 | 0.03 | 64 | 2.529724 | 10 | 3 |
| 34 | 39.5 | 0.54 | 0.005 | 0.5 | 0.75 | 0.03 | 64 | 2.520005 | 10 | 3 |
| 34 | 39.75 | 0.54 | 0.005 | 0.5 | 0.75 | 0.03 | 64 | 2.430968 | 10 | 3 |
| 34 | 40 | 0.54 | 0.005 | 0.5 | 0.75 | 0.03 | 64 | 2.373474 | 10 | 3 |
| 34 | 40.25 | 0.54 | 0.005 | 0.5 | 0.75 | 0.03 | 64 | 2.42504 | 10 | 3 |

Fig. 11B

| Crown Angle | Pavillion Angle | Table Size | Culet Size | Star Length | Lower Girdle Length | Girdle Thickness | # of Girdle Facets | DCLR3 | Wavelength Sampling Interval (nm) | Brightness Cutoff Threshold Factor |
|---|---|---|---|---|---|---|---|---|---|---|
| 34 | 40.5 | 0.54 | 0.005 | 0.5 | 0.75 | 0.03 | 64 | 2.43167 | 10 | 3 |
| 34 | 40.75 | 0.54 | 0.005 | 0.5 | 0.75 | 0.03 | 64 | 2.362006 | 10 | 3 |
| 34 | 41 | 0.54 | 0.005 | 0.5 | 0.75 | 0.03 | 64 | 2.362826 | 10 | 3 |
| 34 | 41.25 | 0.54 | 0.005 | 0.5 | 0.75 | 0.03 | 64 | 2.151353 | 10 | 3 |
| 34 | 41.5 | 0.54 | 0.005 | 0.5 | 0.75 | 0.03 | 64 | 2.097091 | 10 | 3 |
| 34 | 41.75 | 0.54 | 0.005 | 0.5 | 0.75 | 0.03 | 64 | 2.055188 | 10 | 3 |
| 34 | 42 | 0.54 | 0.005 | 0.5 | 0.75 | 0.03 | 64 | 1.974824 | 10 | 3 |
| 34 | 42.25 | 0.54 | 0.005 | 0.5 | 0.75 | 0.03 | 64 | 1.879331 | 10 | 3 |
| 34 | 42.5 | 0.54 | 0.005 | 0.5 | 0.75 | 0.03 | 64 | 1.829478 | 10 | 3 |
| 34 | 42.75 | 0.54 | 0.005 | 0.5 | 0.75 | 0.03 | 64 | 1.568495 | 10 | 3 |
| 34 | 43 | 0.54 | 0.005 | 0.5 | 0.75 | 0.03 | 64 | 1.663354 | 10 | 3 |
| 34 | 38 | 0.55 | 0.005 | 0.5 | 0.75 | 0.03 | 64 | 2.487371 | 10 | 3 |
| 34 | 38.25 | 0.55 | 0.005 | 0.5 | 0.75 | 0.03 | 64 | 2.535877 | 10 | 3 |
| 34 | 38.5 | 0.55 | 0.005 | 0.5 | 0.75 | 0.03 | 64 | 2.506953 | 10 | 3 |
| 34 | 38.75 | 0.55 | 0.005 | 0.5 | 0.75 | 0.03 | 64 | 2.499127 | 10 | 3 |
| 34 | 39 | 0.55 | 0.005 | 0.5 | 0.75 | 0.03 | 64 | 2.479138 | 10 | 3 |
| 34 | 39.25 | 0.55 | 0.005 | 0.5 | 0.75 | 0.03 | 64 | 2.497332 | 10 | 3 |
| 34 | 39.5 | 0.55 | 0.005 | 0.5 | 0.75 | 0.03 | 64 | 2.47153 | 10 | 3 |
| 34 | 39.75 | 0.55 | 0.005 | 0.5 | 0.75 | 0.03 | 64 | 2.408166 | 10 | 3 |
| 34 | 40 | 0.55 | 0.005 | 0.5 | 0.75 | 0.03 | 64 | 2.380299 | 10 | 3 |
| 34 | 40.25 | 0.55 | 0.005 | 0.5 | 0.75 | 0.03 | 64 | 2.411317 | 10 | 3 |
| 34 | 40.5 | 0.55 | 0.005 | 0.5 | 0.75 | 0.03 | 64 | 2.386556 | 10 | 3 |
| 34 | 40.75 | 0.55 | 0.005 | 0.5 | 0.75 | 0.03 | 64 | 2.322224 | 10 | 3 |
| 34 | 41 | 0.55 | 0.005 | 0.5 | 0.75 | 0.03 | 64 | 2.307629 | 10 | 3 |
| 34 | 41.25 | 0.55 | 0.005 | 0.5 | 0.75 | 0.03 | 64 | 2.092016 | 10 | 3 |
| 34 | 41.5 | 0.55 | 0.005 | 0.5 | 0.75 | 0.03 | 64 | 2.011882 | 10 | 3 |
| 34 | 41.75 | 0.55 | 0.005 | 0.5 | 0.75 | 0.03 | 64 | 1.972341 | 10 | 3 |
| 34 | 42 | 0.55 | 0.005 | 0.5 | 0.75 | 0.03 | 64 | 1.931296 | 10 | 3 |
| 34 | 42.25 | 0.55 | 0.005 | 0.5 | 0.75 | 0.03 | 64 | 1.876851 | 10 | 3 |
| 34 | 42.5 | 0.55 | 0.005 | 0.5 | 0.75 | 0.03 | 64 | 1.795366 | 10 | 3 |
| 34 | 42.75 | 0.55 | 0.005 | 0.5 | 0.75 | 0.03 | 64 | 1.666759 | 10 | 3 |
| 34 | 43 | 0.55 | 0.005 | 0.5 | 0.75 | 0.03 | 64 | 1.628133 | 10 | 3 |
| 34 | 38 | 0.56 | 0.005 | 0.5 | 0.75 | 0.03 | 64 | 2.384859 | 10 | 3 |
| 34 | 38.25 | 0.56 | 0.005 | 0.5 | 0.75 | 0.03 | 64 | 2.430965 | 10 | 3 |
| 34 | 38.5 | 0.56 | 0.005 | 0.5 | 0.75 | 0.03 | 64 | 2.438316 | 10 | 3 |
| 34 | 38.75 | 0.56 | 0.005 | 0.5 | 0.75 | 0.03 | 64 | 2.485844 | 10 | 3 |
| 34 | 39 | 0.56 | 0.005 | 0.5 | 0.75 | 0.03 | 64 | 2.472669 | 10 | 3 |
| 34 | 39.25 | 0.56 | 0.005 | 0.5 | 0.75 | 0.03 | 64 | 2.458902 | 10 | 3 |
| 34 | 39.5 | 0.56 | 0.005 | 0.5 | 0.75 | 0.03 | 64 | 2.428729 | 10 | 3 |
| 34 | 39.75 | 0.56 | 0.005 | 0.5 | 0.75 | 0.03 | 64 | 2.386446 | 10 | 3 |
| 34 | 40 | 0.56 | 0.005 | 0.5 | 0.75 | 0.03 | 64 | 2.368464 | 10 | 3 |
| 34 | 40.25 | 0.56 | 0.005 | 0.5 | 0.75 | 0.03 | 64 | 2.357008 | 10 | 3 |
| 34 | 40.5 | 0.56 | 0.005 | 0.5 | 0.75 | 0.03 | 64 | 2.345421 | 10 | 3 |
| 34 | 40.75 | 0.56 | 0.005 | 0.5 | 0.75 | 0.03 | 64 | 2.297761 | 10 | 3 |
| 34 | 41 | 0.56 | 0.005 | 0.5 | 0.75 | 0.03 | 64 | 2.267499 | 10 | 3 |
| 34 | 41.25 | 0.56 | 0.005 | 0.5 | 0.75 | 0.03 | 64 | 2.048954 | 10 | 3 |
| 34 | 41.5 | 0.56 | 0.005 | 0.5 | 0.75 | 0.03 | 64 | 1.976045 | 10 | 3 |
| 34 | 41.75 | 0.56 | 0.005 | 0.5 | 0.75 | 0.03 | 64 | 1.912248 | 10 | 3 |
| 34 | 42 | 0.56 | 0.005 | 0.5 | 0.75 | 0.03 | 64 | 1.895277 | 10 | 3 |
| 34 | 42.25 | 0.56 | 0.005 | 0.5 | 0.75 | 0.03 | 64 | 1.866763 | 10 | 3 |
| 34 | 42.5 | 0.56 | 0.005 | 0.5 | 0.75 | 0.03 | 64 | 1.77687 | 10 | 3 |
| 34 | 42.75 | 0.56 | 0.005 | 0.5 | 0.75 | 0.03 | 64 | 1.660786 | 10 | 3 |

Fig. 11C

| Crown Angle | Pavillion Angle | Table Size | Culet Size | Star Length | Lower Girdle Length | Girdle Thickness | # of Girdle Facets | DCLR3 | Wavelength Sampling Interval (nm) | Brightness Cutoff Threshold Factor |
|---|---|---|---|---|---|---|---|---|---|---|
| 34 | 43 | 0.56 | 0.005 | 0.5 | 0.75 | 0.03 | 64 | 1.598593 | 10 | 3 |
| 34 | 38 | 0.57 | 0.005 | 0.5 | 0.75 | 0.03 | 64 | 2.29322 | 10 | 3 |
| 34 | 38.25 | 0.57 | 0.005 | 0.5 | 0.75 | 0.03 | 64 | 2.318528 | 10 | 3 |
| 34 | 38.5 | 0.57 | 0.005 | 0.5 | 0.75 | 0.03 | 64 | 2.371713 | 10 | 3 |
| 34 | 38.75 | 0.57 | 0.005 | 0.5 | 0.75 | 0.03 | 64 | 2.440226 | 10 | 3 |
| 34 | 39 | 0.57 | 0.005 | 0.5 | 0.75 | 0.03 | 64 | 2.439588 | 10 | 3 |
| 34 | 39.25 | 0.57 | 0.005 | 0.5 | 0.75 | 0.03 | 64 | 2.424983 | 10 | 3 |
| 34 | 39.5 | 0.57 | 0.005 | 0.5 | 0.75 | 0.03 | 64 | 2.407552 | 10 | 3 |
| 34 | 39.75 | 0.57 | 0.005 | 0.5 | 0.75 | 0.03 | 64 | 2.343643 | 10 | 3 |
| 34 | 40 | 0.57 | 0.005 | 0.5 | 0.75 | 0.03 | 64 | 2.331335 | 10 | 3 |
| 34 | 40.25 | 0.57 | 0.005 | 0.5 | 0.75 | 0.03 | 64 | 2.321218 | 10 | 3 |
| 34 | 40.5 | 0.57 | 0.005 | 0.5 | 0.75 | 0.03 | 64 | 2.313417 | 10 | 3 |
| 34 | 40.75 | 0.57 | 0.005 | 0.5 | 0.75 | 0.03 | 64 | 2.261803 | 10 | 3 |
| 34 | 41 | 0.57 | 0.005 | 0.5 | 0.75 | 0.03 | 64 | 2.240168 | 10 | 3 |
| 34 | 41.25 | 0.57 | 0.005 | 0.5 | 0.75 | 0.03 | 64 | 2.048184 | 10 | 3 |
| 34 | 41.5 | 0.57 | 0.005 | 0.5 | 0.75 | 0.03 | 64 | 1.976444 | 10 | 3 |
| 34 | 41.75 | 0.57 | 0.005 | 0.5 | 0.75 | 0.03 | 64 | 1.891455 | 10 | 3 |
| 34 | 42 | 0.57 | 0.005 | 0.5 | 0.75 | 0.03 | 64 | 1.870176 | 10 | 3 |
| 34 | 42.25 | 0.57 | 0.005 | 0.5 | 0.75 | 0.03 | 64 | 1.849415 | 10 | 3 |
| 34 | 42.5 | 0.57 | 0.005 | 0.5 | 0.75 | 0.03 | 64 | 1.758388 | 10 | 3 |
| 34 | 42.75 | 0.57 | 0.005 | 0.5 | 0.75 | 0.03 | 64 | 1.625158 | 10 | 3 |
| 34 | 43 | 0.57 | 0.005 | 0.5 | 0.75 | 0.03 | 64 | 1.562979 | 10 | 3 |
| 34 | 38 | 0.58 | 0.005 | 0.5 | 0.75 | 0.03 | 64 | 2.2449 | 10 | 3 |
| 34 | 38.25 | 0.58 | 0.005 | 0.5 | 0.75 | 0.03 | 64 | 2.200018 | 10 | 3 |
| 34 | 38.5 | 0.58 | 0.005 | 0.5 | 0.75 | 0.03 | 64 | 2.314943 | 10 | 3 |
| 34 | 38.75 | 0.58 | 0.005 | 0.5 | 0.75 | 0.03 | 64 | 2.380773 | 10 | 3 |
| 34 | 39 | 0.58 | 0.005 | 0.5 | 0.75 | 0.03 | 64 | 2.393095 | 10 | 3 |
| 34 | 39.25 | 0.58 | 0.005 | 0.5 | 0.75 | 0.03 | 64 | 2.40404 | 10 | 3 |
| 34 | 39.5 | 0.58 | 0.005 | 0.5 | 0.75 | 0.03 | 64 | 2.383528 | 10 | 3 |
| 34 | 39.75 | 0.58 | 0.005 | 0.5 | 0.75 | 0.03 | 64 | 2.325183 | 10 | 3 |
| 34 | 40 | 0.58 | 0.005 | 0.5 | 0.75 | 0.03 | 64 | 2.302531 | 10 | 3 |
| 34 | 40.25 | 0.58 | 0.005 | 0.5 | 0.75 | 0.03 | 64 | 2.2962 | 10 | 3 |
| 34 | 40.5 | 0.58 | 0.005 | 0.5 | 0.75 | 0.03 | 64 | 2.273146 | 10 | 3 |
| 34 | 40.75 | 0.58 | 0.005 | 0.5 | 0.75 | 0.03 | 64 | 2.259006 | 10 | 3 |
| 34 | 41 | 0.58 | 0.005 | 0.5 | 0.75 | 0.03 | 64 | 2.25262 | 10 | 3 |
| 34 | 41.25 | 0.58 | 0.005 | 0.5 | 0.75 | 0.03 | 64 | 2.052269 | 10 | 3 |
| 34 | 41.5 | 0.58 | 0.005 | 0.5 | 0.75 | 0.03 | 64 | 1.987241 | 10 | 3 |
| 34 | 41.75 | 0.58 | 0.005 | 0.5 | 0.75 | 0.03 | 64 | 1.888162 | 10 | 3 |
| 34 | 42 | 0.58 | 0.005 | 0.5 | 0.75 | 0.03 | 64 | 1.843398 | 10 | 3 |
| 34 | 42.25 | 0.58 | 0.005 | 0.5 | 0.75 | 0.03 | 64 | 1.83487 | 10 | 3 |
| 34 | 42.5 | 0.58 | 0.005 | 0.5 | 0.75 | 0.03 | 64 | 1.738423 | 10 | 3 |
| 34 | 42.75 | 0.58 | 0.005 | 0.5 | 0.75 | 0.03 | 64 | 1.599105 | 10 | 3 |
| 34 | 43 | 0.58 | 0.005 | 0.5 | 0.75 | 0.03 | 64 | 1.535505 | 10 | 3 |
| 34 | 38 | 0.59 | 0.005 | 0.5 | 0.75 | 0.03 | 64 | 2.184323 | 10 | 3 |
| 34 | 38.25 | 0.59 | 0.005 | 0.5 | 0.75 | 0.03 | 64 | 2.109861 | 10 | 3 |
| 34 | 38.5 | 0.59 | 0.005 | 0.5 | 0.75 | 0.03 | 64 | 2.225028 | 10 | 3 |
| 34 | 38.75 | 0.59 | 0.005 | 0.5 | 0.75 | 0.03 | 64 | 2.341652 | 10 | 3 |
| 34 | 39 | 0.59 | 0.005 | 0.5 | 0.75 | 0.03 | 64 | 2.377811 | 10 | 3 |
| 34 | 39.25 | 0.59 | 0.005 | 0.5 | 0.75 | 0.03 | 64 | 2.415963 | 10 | 3 |
| 34 | 39.5 | 0.59 | 0.005 | 0.5 | 0.75 | 0.03 | 64 | 2.350964 | 10 | 3 |
| 34 | 39.75 | 0.59 | 0.005 | 0.5 | 0.75 | 0.03 | 64 | 2.311079 | 10 | 3 |
| 34 | 40 | 0.59 | 0.005 | 0.5 | 0.75 | 0.03 | 64 | 2.303502 | 10 | 3 |

Fig. 11D

| Crown Angle | Pavilion Angle | Table Size | Culet Size | Star Length | Lower Girdle Length | Girdle Thickness | # of Girdle Facets | DCLR3 | Wavelength Sampling Interval (nm) | Brightness Cutoff Threshold Factor |
|---|---|---|---|---|---|---|---|---|---|---|
| 34 | 40.25 | 0.59 | 0.005 | 0.5 | 0.75 | 0.03 | 64 | 2.305293 | 10 | 3 |
| 34 | 40.5 | 0.59 | 0.005 | 0.5 | 0.75 | 0.03 | 64 | 2.257595 | 10 | 3 |
| 34 | 40.75 | 0.59 | 0.005 | 0.5 | 0.75 | 0.03 | 64 | 2.244672 | 10 | 3 |
| 34 | 41 | 0.59 | 0.005 | 0.5 | 0.75 | 0.03 | 64 | 2.248976 | 10 | 3 |
| 34 | 41.25 | 0.59 | 0.005 | 0.5 | 0.75 | 0.03 | 64 | 2.044514 | 10 | 3 |
| 34 | 41.5 | 0.59 | 0.005 | 0.5 | 0.75 | 0.03 | 64 | 1.96695 | 10 | 3 |
| 34 | 41.75 | 0.59 | 0.005 | 0.5 | 0.75 | 0.03 | 64 | 1.897437 | 10 | 3 |
| 34 | 42 | 0.59 | 0.005 | 0.5 | 0.75 | 0.03 | 64 | 1.827485 | 10 | 3 |
| 34 | 42.25 | 0.59 | 0.005 | 0.5 | 0.75 | 0.03 | 64 | 1.807431 | 10 | 3 |
| 34 | 42.5 | 0.59 | 0.005 | 0.5 | 0.75 | 0.03 | 64 | 1.701863 | 10 | 3 |
| 34 | 42.75 | 0.59 | 0.005 | 0.5 | 0.75 | 0.03 | 64 | 1.565639 | 10 | 3 |
| 34 | 43 | 0.59 | 0.005 | 0.5 | 0.75 | 0.03 | 64 | 1.505227 | 10 | 3 |
| 34 | 38 | 0.6 | 0.005 | 0.5 | 0.75 | 0.03 | 64 | 2.116379 | 10 | 3 |
| 34 | 38.25 | 0.6 | 0.005 | 0.5 | 0.75 | 0.03 | 64 | 2.034801 | 10 | 3 |
| 34 | 38.5 | 0.6 | 0.005 | 0.5 | 0.75 | 0.03 | 64 | 2.163161 | 10 | 3 |
| 34 | 38.75 | 0.6 | 0.005 | 0.5 | 0.75 | 0.03 | 64 | 2.317819 | 10 | 3 |
| 34 | 39 | 0.6 | 0.005 | 0.5 | 0.75 | 0.03 | 64 | 2.379017 | 10 | 3 |
| 34 | 39.25 | 0.6 | 0.005 | 0.5 | 0.75 | 0.03 | 64 | 2.441714 | 10 | 3 |
| 34 | 39.5 | 0.6 | 0.005 | 0.5 | 0.75 | 0.03 | 64 | 2.360155 | 10 | 3 |
| 34 | 39.75 | 0.6 | 0.005 | 0.5 | 0.75 | 0.03 | 64 | 2.303409 | 10 | 3 |
| 34 | 40 | 0.6 | 0.005 | 0.5 | 0.75 | 0.03 | 64 | 2.302245 | 10 | 3 |
| 34 | 40.25 | 0.6 | 0.005 | 0.5 | 0.75 | 0.03 | 64 | 2.32489 | 10 | 3 |
| 34 | 40.5 | 0.6 | 0.005 | 0.5 | 0.75 | 0.03 | 64 | 2.245972 | 10 | 3 |
| 34 | 40.75 | 0.6 | 0.005 | 0.5 | 0.75 | 0.03 | 64 | 2.227878 | 10 | 3 |
| 34 | 41 | 0.6 | 0.005 | 0.5 | 0.75 | 0.03 | 64 | 2.252926 | 10 | 3 |
| 34 | 41.25 | 0.6 | 0.005 | 0.5 | 0.75 | 0.03 | 64 | 2.052099 | 10 | 3 |
| 34 | 41.5 | 0.6 | 0.005 | 0.5 | 0.75 | 0.03 | 64 | 1.97704 | 10 | 3 |
| 34 | 41.75 | 0.6 | 0.005 | 0.5 | 0.75 | 0.03 | 64 | 1.896367 | 10 | 3 |
| 34 | 42 | 0.6 | 0.005 | 0.5 | 0.75 | 0.03 | 64 | 1.821832 | 10 | 3 |
| 34 | 42.25 | 0.6 | 0.005 | 0.5 | 0.75 | 0.03 | 64 | 1.788714 | 10 | 3 |
| 34 | 42.5 | 0.6 | 0.005 | 0.5 | 0.75 | 0.03 | 64 | 1.685721 | 10 | 3 |
| 34 | 42.75 | 0.6 | 0.005 | 0.5 | 0.75 | 0.03 | 64 | 1.530645 | 10 | 3 |
| 34 | 43 | 0.6 | 0.005 | 0.5 | 0.75 | 0.03 | 64 | 1.464473 | 10 | 3 |
| 34 | 38 | 0.61 | 0.005 | 0.5 | 0.75 | 0.03 | 64 | 2.080339 | 10 | 3 |
| 34 | 38.25 | 0.61 | 0.005 | 0.5 | 0.75 | 0.03 | 64 | 2.029245 | 10 | 3 |
| 34 | 38.5 | 0.61 | 0.005 | 0.5 | 0.75 | 0.03 | 64 | 2.130434 | 10 | 3 |
| 34 | 38.75 | 0.61 | 0.005 | 0.5 | 0.75 | 0.03 | 64 | 2.287073 | 10 | 3 |
| 34 | 39 | 0.61 | 0.005 | 0.5 | 0.75 | 0.03 | 64 | 2.360598 | 10 | 3 |
| 34 | 39.25 | 0.61 | 0.005 | 0.5 | 0.75 | 0.03 | 64 | 2.475646 | 10 | 3 |
| 34 | 39.5 | 0.61 | 0.005 | 0.5 | 0.75 | 0.03 | 64 | 2.363741 | 10 | 3 |
| 34 | 39.75 | 0.61 | 0.005 | 0.5 | 0.75 | 0.03 | 64 | 2.296805 | 10 | 3 |
| 34 | 40 | 0.61 | 0.005 | 0.5 | 0.75 | 0.03 | 64 | 2.300797 | 10 | 3 |
| 34 | 40.25 | 0.61 | 0.005 | 0.5 | 0.75 | 0.03 | 64 | 2.317179 | 10 | 3 |
| 34 | 40.5 | 0.61 | 0.005 | 0.5 | 0.75 | 0.03 | 64 | 2.254045 | 10 | 3 |
| 34 | 40.75 | 0.61 | 0.005 | 0.5 | 0.75 | 0.03 | 64 | 2.213688 | 10 | 3 |
| 34 | 41 | 0.61 | 0.005 | 0.5 | 0.75 | 0.03 | 64 | 2.243129 | 10 | 3 |
| 34 | 41.25 | 0.61 | 0.005 | 0.5 | 0.75 | 0.03 | 64 | 2.031185 | 10 | 3 |
| 34 | 41.5 | 0.61 | 0.005 | 0.5 | 0.75 | 0.03 | 64 | 1.965116 | 10 | 3 |
| 34 | 41.75 | 0.61 | 0.005 | 0.5 | 0.75 | 0.03 | 64 | 1.879425 | 10 | 3 |
| 34 | 42 | 0.61 | 0.005 | 0.5 | 0.75 | 0.03 | 64 | 1.809611 | 10 | 3 |
| 34 | 42.25 | 0.61 | 0.005 | 0.5 | 0.75 | 0.03 | 64 | 1.768348 | 10 | 3 |
| 34 | 42.5 | 0.61 | 0.005 | 0.5 | 0.75 | 0.03 | 64 | 1.679952 | 10 | 3 |

Fig. 11E

| Crown Angle | Pavillion Angle | Table Size | Culet Size | Star Length | Lower Girdle Length | Girdle Thickness | # of Girdle Facets | DCLR3 | Wavelength Sampling Interval (nm) | Brightness Cutoff Threshold Factor |
|---|---|---|---|---|---|---|---|---|---|---|
| 34 | 42.75 | 0.61 | 0.005 | 0.5 | 0.75 | 0.03 | 64 | 1.484666 | 10 | 3 |
| 34 | 43 | 0.61 | 0.005 | 0.5 | 0.75 | 0.03 | 64 | 1.43055 | 10 | 3 |
| 34 | 38 | 0.62 | 0.005 | 0.5 | 0.75 | 0.03 | 64 | 2.030561 | 10 | 3 |
| 34 | 38.25 | 0.62 | 0.005 | 0.5 | 0.75 | 0.03 | 64 | 2.034123 | 10 | 3 |
| 34 | 38.5 | 0.62 | 0.005 | 0.5 | 0.75 | 0.03 | 64 | 2.090965 | 10 | 3 |
| 34 | 38.75 | 0.62 | 0.005 | 0.5 | 0.75 | 0.03 | 64 | 2.255456 | 10 | 3 |
| 34 | 39 | 0.62 | 0.005 | 0.5 | 0.75 | 0.03 | 64 | 2.349043 | 10 | 3 |
| 34 | 39.25 | 0.62 | 0.005 | 0.5 | 0.75 | 0.03 | 64 | 2.47217 | 10 | 3 |
| 34 | 39.5 | 0.62 | 0.005 | 0.5 | 0.75 | 0.03 | 64 | 2.355233 | 10 | 3 |
| 34 | 39.75 | 0.62 | 0.005 | 0.5 | 0.75 | 0.03 | 64 | 2.295602 | 10 | 3 |
| 34 | 40 | 0.62 | 0.005 | 0.5 | 0.75 | 0.03 | 64 | 2.304955 | 10 | 3 |
| 34 | 40.25 | 0.62 | 0.005 | 0.5 | 0.75 | 0.03 | 64 | 2.30649 | 10 | 3 |
| 34 | 40.5 | 0.62 | 0.005 | 0.5 | 0.75 | 0.03 | 64 | 2.248172 | 10 | 3 |
| 34 | 40.75 | 0.62 | 0.005 | 0.5 | 0.75 | 0.03 | 64 | 2.199159 | 10 | 3 |
| 34 | 41 | 0.62 | 0.005 | 0.5 | 0.75 | 0.03 | 64 | 2.22692 | 10 | 3 |
| 34 | 41.25 | 0.62 | 0.005 | 0.5 | 0.75 | 0.03 | 64 | 2.005718 | 10 | 3 |
| 34 | 41.5 | 0.62 | 0.005 | 0.5 | 0.75 | 0.03 | 64 | 1.951076 | 10 | 3 |
| 34 | 41.75 | 0.62 | 0.005 | 0.5 | 0.75 | 0.03 | 64 | 1.868956 | 10 | 3 |
| 34 | 42 | 0.62 | 0.005 | 0.5 | 0.75 | 0.03 | 64 | 1.772161 | 10 | 3 |
| 34 | 42.25 | 0.62 | 0.005 | 0.5 | 0.75 | 0.03 | 64 | 1.734037 | 10 | 3 |
| 34 | 42.5 | 0.62 | 0.005 | 0.5 | 0.75 | 0.03 | 64 | 1.655716 | 10 | 3 |
| 34 | 42.75 | 0.62 | 0.005 | 0.5 | 0.75 | 0.03 | 64 | 1.475449 | 10 | 3 |
| 34 | 43 | 0.62 | 0.005 | 0.5 | 0.75 | 0.03 | 64 | 1.401287 | 10 | 3 |
| 34 | 38 | 0.63 | 0.005 | 0.5 | 0.75 | 0.03 | 64 | 1.994225 | 10 | 3 |
| 34 | 38.25 | 0.63 | 0.005 | 0.5 | 0.75 | 0.03 | 64 | 2.015877 | 10 | 3 |
| 34 | 38.5 | 0.63 | 0.005 | 0.5 | 0.75 | 0.03 | 64 | 2.045052 | 10 | 3 |
| 34 | 38.75 | 0.63 | 0.005 | 0.5 | 0.75 | 0.03 | 64 | 2.221786 | 10 | 3 |
| 34 | 39 | 0.63 | 0.005 | 0.5 | 0.75 | 0.03 | 64 | 2.346742 | 10 | 3 |
| 34 | 39.25 | 0.63 | 0.005 | 0.5 | 0.75 | 0.03 | 64 | 2.490031 | 10 | 3 |
| 34 | 39.5 | 0.63 | 0.005 | 0.5 | 0.75 | 0.03 | 64 | 2.376295 | 10 | 3 |
| 34 | 39.75 | 0.63 | 0.005 | 0.5 | 0.75 | 0.03 | 64 | 2.28009 | 10 | 3 |
| 34 | 40 | 0.63 | 0.005 | 0.5 | 0.75 | 0.03 | 64 | 2.297561 | 10 | 3 |
| 34 | 40.25 | 0.63 | 0.005 | 0.5 | 0.75 | 0.03 | 64 | 2.276601 | 10 | 3 |
| 34 | 40.5 | 0.63 | 0.005 | 0.5 | 0.75 | 0.03 | 64 | 2.248214 | 10 | 3 |
| 34 | 40.75 | 0.63 | 0.005 | 0.5 | 0.75 | 0.03 | 64 | 2.217128 | 10 | 3 |
| 34 | 41 | 0.63 | 0.005 | 0.5 | 0.75 | 0.03 | 64 | 2.208079 | 10 | 3 |
| 34 | 41.25 | 0.63 | 0.005 | 0.5 | 0.75 | 0.03 | 64 | 1.970603 | 10 | 3 |
| 34 | 41.5 | 0.63 | 0.005 | 0.5 | 0.75 | 0.03 | 64 | 1.92719 | 10 | 3 |
| 34 | 41.75 | 0.63 | 0.005 | 0.5 | 0.75 | 0.03 | 64 | 1.846185 | 10 | 3 |
| 34 | 42 | 0.63 | 0.005 | 0.5 | 0.75 | 0.03 | 64 | 1.745782 | 10 | 3 |
| 34 | 42.25 | 0.63 | 0.005 | 0.5 | 0.75 | 0.03 | 64 | 1.680691 | 10 | 3 |
| 34 | 42.5 | 0.63 | 0.005 | 0.5 | 0.75 | 0.03 | 64 | 1.627788 | 10 | 3 |
| 34 | 42.75 | 0.63 | 0.005 | 0.5 | 0.75 | 0.03 | 64 | 1.449062 | 10 | 3 |
| 34 | 43 | 0.63 | 0.005 | 0.5 | 0.75 | 0.03 | 64 | 1.378223 | 10 | 3 |
| 34 | 38 | 0.64 | 0.005 | 0.5 | 0.75 | 0.03 | 64 | 1.937163 | 10 | 3 |
| 34 | 38.25 | 0.64 | 0.005 | 0.5 | 0.75 | 0.03 | 64 | 1.986278 | 10 | 3 |
| 34 | 38.5 | 0.64 | 0.005 | 0.5 | 0.75 | 0.03 | 64 | 2.104674 | 10 | 3 |
| 34 | 38.75 | 0.64 | 0.005 | 0.5 | 0.75 | 0.03 | 64 | 2.177021 | 10 | 3 |
| 34 | 39 | 0.64 | 0.005 | 0.5 | 0.75 | 0.03 | 64 | 2.339914 | 10 | 3 |
| 34 | 39.25 | 0.64 | 0.005 | 0.5 | 0.75 | 0.03 | 64 | 2.485933 | 10 | 3 |
| 34 | 39.5 | 0.64 | 0.005 | 0.5 | 0.75 | 0.03 | 64 | 2.371974 | 10 | 3 |
| 34 | 39.75 | 0.64 | 0.005 | 0.5 | 0.75 | 0.03 | 64 | 2.260436 | 10 | 3 |

Fig. 11F

| Crown Angle | Pavillion Angle | Table Size | Culet Size | Star Length | Lower Girdle Length | Girdle Thickness | # of Girdle Facets | DCLR3 | Wavelength Sampling Interval (nm) | Brightness Cutoff Threshold Factor |
|---|---|---|---|---|---|---|---|---|---|---|
| 34 | 40 | 0.64 | 0.005 | 0.5 | 0.75 | 0.03 | 64 | 2.288242 | 10 | 3 |
| 34 | 40.25 | 0.64 | 0.005 | 0.5 | 0.75 | 0.03 | 64 | 2.259336 | 10 | 3 |
| 34 | 40.5 | 0.64 | 0.005 | 0.5 | 0.75 | 0.03 | 64 | 2.230171 | 10 | 3 |
| 34 | 40.75 | 0.64 | 0.005 | 0.5 | 0.75 | 0.03 | 64 | 2.196695 | 10 | 3 |
| 34 | 41 | 0.64 | 0.005 | 0.5 | 0.75 | 0.03 | 64 | 2.200361 | 10 | 3 |
| 34 | 41.25 | 0.64 | 0.005 | 0.5 | 0.75 | 0.03 | 64 | 1.928936 | 10 | 3 |
| 34 | 41.5 | 0.64 | 0.005 | 0.5 | 0.75 | 0.03 | 64 | 1.887913 | 10 | 3 |
| 34 | 41.75 | 0.64 | 0.005 | 0.5 | 0.75 | 0.03 | 64 | 1.829684 | 10 | 3 |
| 34 | 42 | 0.64 | 0.005 | 0.5 | 0.75 | 0.03 | 64 | 1.694517 | 10 | 3 |
| 34 | 42.25 | 0.64 | 0.005 | 0.5 | 0.75 | 0.03 | 64 | 1.641441 | 10 | 3 |
| 34 | 42.5 | 0.64 | 0.005 | 0.5 | 0.75 | 0.03 | 64 | 1.593743 | 10 | 3 |
| 34 | 42.75 | 0.64 | 0.005 | 0.5 | 0.75 | 0.03 | 64 | 1.399281 | 10 | 3 |
| 34 | 43 | 0.64 | 0.005 | 0.5 | 0.75 | 0.03 | 64 | 1.381328 | 10 | 3 |
| 34 | 38 | 0.65 | 0.005 | 0.5 | 0.75 | 0.03 | 64 | 1.875263 | 10 | 3 |
| 34 | 38.25 | 0.65 | 0.005 | 0.5 | 0.75 | 0.03 | 64 | 1.950259 | 10 | 3 |
| 34 | 38.5 | 0.65 | 0.005 | 0.5 | 0.75 | 0.03 | 64 | 2.111066 | 10 | 3 |
| 34 | 38.75 | 0.65 | 0.005 | 0.5 | 0.75 | 0.03 | 64 | 2.122745 | 10 | 3 |
| 34 | 39 | 0.65 | 0.005 | 0.5 | 0.75 | 0.03 | 64 | 2.318192 | 10 | 3 |
| 34 | 39.25 | 0.65 | 0.005 | 0.5 | 0.75 | 0.03 | 64 | 2.471633 | 10 | 3 |
| 34 | 39.5 | 0.65 | 0.005 | 0.5 | 0.75 | 0.03 | 64 | 2.353229 | 10 | 3 |
| 34 | 39.75 | 0.65 | 0.005 | 0.5 | 0.75 | 0.03 | 64 | 2.272917 | 10 | 3 |
| 34 | 40 | 0.65 | 0.005 | 0.5 | 0.75 | 0.03 | 64 | 2.274338 | 10 | 3 |
| 34 | 40.25 | 0.65 | 0.005 | 0.5 | 0.75 | 0.03 | 64 | 2.239931 | 10 | 3 |
| 34 | 40.5 | 0.65 | 0.005 | 0.5 | 0.75 | 0.03 | 64 | 2.193609 | 10 | 3 |
| 34 | 40.75 | 0.65 | 0.005 | 0.5 | 0.75 | 0.03 | 64 | 2.195184 | 10 | 3 |
| 34 | 41 | 0.65 | 0.005 | 0.5 | 0.75 | 0.03 | 64 | 2.202781 | 10 | 3 |
| 34 | 41.25 | 0.65 | 0.005 | 0.5 | 0.75 | 0.03 | 64 | 1.906847 | 10 | 3 |
| 34 | 41.5 | 0.65 | 0.005 | 0.5 | 0.75 | 0.03 | 64 | 1.837126 | 10 | 3 |
| 34 | 41.75 | 0.65 | 0.005 | 0.5 | 0.75 | 0.03 | 64 | 1.776166 | 10 | 3 |
| 34 | 42 | 0.65 | 0.005 | 0.5 | 0.75 | 0.03 | 64 | 1.634451 | 10 | 3 |
| 34 | 42.25 | 0.65 | 0.005 | 0.5 | 0.75 | 0.03 | 64 | 1.59568 | 10 | 3 |
| 34 | 42.5 | 0.65 | 0.005 | 0.5 | 0.75 | 0.03 | 64 | 1.544586 | 10 | 3 |
| 34 | 42.75 | 0.65 | 0.005 | 0.5 | 0.75 | 0.03 | 64 | 1.350065 | 10 | 3 |
| 34 | 43 | 0.65 | 0.005 | 0.5 | 0.75 | 0.03 | 64 | 1.359024 | 10 | 3 |

Fig. 12A

| Crown Angle | Pavillion Angle | Table Size | Culet Size | Star Length | Lower Girdle Length | Girdle Thickness | # of Girdle Facets | DCLR2 | Wavelength Sampling Interval (nm) | Brightness Cutoff Threshold Factor |
|---|---|---|---|---|---|---|---|---|---|---|
| 34 | 0.52 | 0.005 | 0.005 | 0.5 | 0.75 | 0.03 | 64 | 0.830853 | 10 | 2 |
| 34 | 0.52 | 0.005 | 0.005 | 0.5 | 0.75 | 0.03 | 64 | 0.815603 | 10 | 2 |
| 34 | 38.5 | 0.52 | 0.005 | 0.5 | 0.75 | 0.03 | 64 | 0.775263 | 10 | 2 |
| 34 | 38.75 | 0.52 | 0.005 | 0.5 | 0.75 | 0.03 | 64 | 0.782148 | 10 | 2 |
| 34 | 39 | 0.52 | 0.005 | 0.5 | 0.75 | 0.03 | 64 | 0.842428 | 10 | 2 |
| 34 | 39.25 | 0.52 | 0.005 | 0.5 | 0.75 | 0.03 | 64 | 0.868842 | 10 | 2 |
| 34 | 39.5 | 0.52 | 0.005 | 0.5 | 0.75 | 0.03 | 64 | 0.887367 | 10 | 2 |
| 34 | 39.75 | 0.52 | 0.005 | 0.5 | 0.75 | 0.03 | 64 | 0.897572 | 10 | 2 |
| 34 | 40 | 0.52 | 0.005 | 0.5 | 0.75 | 0.03 | 64 | 0.912094 | 10 | 2 |
| 34 | 40.25 | 0.52 | 0.005 | 0.5 | 0.75 | 0.03 | 64 | 0.903303 | 10 | 2 |
| 34 | 40.5 | 0.52 | 0.005 | 0.5 | 0.75 | 0.03 | 64 | 0.884455 | 10 | 2 |
| 34 | 40.75 | 0.52 | 0.005 | 0.5 | 0.75 | 0.03 | 64 | 0.859532 | 10 | 2 |
| 34 | 41 | 0.52 | 0.005 | 0.5 | 0.75 | 0.03 | 64 | 0.835571 | 10 | 2 |
| 34 | 41.25 | 0.52 | 0.005 | 0.5 | 0.75 | 0.03 | 64 | 0.792055 | 10 | 2 |
| 34 | 41.5 | 0.52 | 0.005 | 0.5 | 0.75 | 0.03 | 64 | 0.794604 | 10 | 2 |
| 34 | 41.75 | 0.52 | 0.005 | 0.5 | 0.75 | 0.03 | 64 | 0.777571 | 10 | 2 |
| 34 | 42 | 0.52 | 0.005 | 0.5 | 0.75 | 0.03 | 64 | 0.755794 | 10 | 2 |
| 34 | 42.25 | 0.52 | 0.005 | 0.5 | 0.75 | 0.03 | 64 | 0.741343 | 10 | 2 |
| 34 | 42.5 | 0.52 | 0.005 | 0.5 | 0.75 | 0.03 | 64 | 0.679849 | 10 | 2 |
| 34 | 42.75 | 0.52 | 0.005 | 0.5 | 0.75 | 0.03 | 64 | 0.632107 | 10 | 2 |
| 34 | 43 | 0.52 | 0.005 | 0.5 | 0.75 | 0.03 | 64 | 0.621588 | 10 | 2 |
| 34 | 38 | 0.53 | 0.005 | 0.5 | 0.75 | 0.03 | 64 | 0.825816 | 10 | 2 |
| 34 | 38.25 | 0.53 | 0.005 | 0.5 | 0.75 | 0.03 | 64 | 0.81762 | 10 | 2 |
| 34 | 38.5 | 0.53 | 0.005 | 0.5 | 0.75 | 0.03 | 64 | 0.775303 | 10 | 2 |
| 34 | 38.75 | 0.53 | 0.005 | 0.5 | 0.75 | 0.03 | 64 | 0.781034 | 10 | 2 |
| 34 | 39 | 0.53 | 0.005 | 0.5 | 0.75 | 0.03 | 64 | 0.839315 | 10 | 2 |
| 34 | 39.25 | 0.53 | 0.005 | 0.5 | 0.75 | 0.03 | 64 | 0.883481 | 10 | 2 |
| 34 | 39.5 | 0.53 | 0.005 | 0.5 | 0.75 | 0.03 | 64 | 0.883092 | 10 | 2 |
| 34 | 39.75 | 0.53 | 0.005 | 0.5 | 0.75 | 0.03 | 64 | 0.898849 | 10 | 2 |
| 34 | 40 | 0.53 | 0.005 | 0.5 | 0.75 | 0.03 | 64 | 0.914231 | 10 | 2 |
| 34 | 40.25 | 0.53 | 0.005 | 0.5 | 0.75 | 0.03 | 64 | 0.905167 | 10 | 2 |
| 34 | 40.5 | 0.53 | 0.005 | 0.5 | 0.75 | 0.03 | 64 | 0.876516 | 10 | 2 |
| 34 | 40.75 | 0.53 | 0.005 | 0.5 | 0.75 | 0.03 | 64 | 0.849069 | 10 | 2 |
| 34 | 41 | 0.53 | 0.005 | 0.5 | 0.75 | 0.03 | 64 | 0.81637 | 10 | 2 |
| 34 | 41.25 | 0.53 | 0.005 | 0.5 | 0.75 | 0.03 | 64 | 0.767044 | 10 | 2 |
| 34 | 41.5 | 0.53 | 0.005 | 0.5 | 0.75 | 0.03 | 64 | 0.760056 | 10 | 2 |
| 34 | 41.75 | 0.53 | 0.005 | 0.5 | 0.75 | 0.03 | 64 | 0.753359 | 10 | 2 |
| 34 | 42 | 0.53 | 0.005 | 0.5 | 0.75 | 0.03 | 64 | 0.74058 | 10 | 2 |
| 34 | 42.25 | 0.53 | 0.005 | 0.5 | 0.75 | 0.03 | 64 | 0.723485 | 10 | 2 |
| 34 | 42.5 | 0.53 | 0.005 | 0.5 | 0.75 | 0.03 | 64 | 0.661301 | 10 | 2 |
| 34 | 42.75 | 0.53 | 0.005 | 0.5 | 0.75 | 0.03 | 64 | 0.612867 | 10 | 2 |
| 34 | 43 | 0.53 | 0.005 | 0.5 | 0.75 | 0.03 | 64 | 0.598343 | 10 | 2 |
| 34 | 38 | 0.54 | 0.005 | 0.5 | 0.75 | 0.03 | 64 | 0.820859 | 10 | 2 |
| 34 | 38.25 | 0.54 | 0.005 | 0.5 | 0.75 | 0.03 | 64 | 0.812162 | 10 | 2 |
| 34 | 38.5 | 0.54 | 0.005 | 0.5 | 0.75 | 0.03 | 64 | 0.773305 | 10 | 2 |
| 34 | 38.75 | 0.54 | 0.005 | 0.5 | 0.75 | 0.03 | 64 | 0.778817 | 10 | 2 |
| 34 | 39 | 0.54 | 0.005 | 0.5 | 0.75 | 0.03 | 64 | 0.828487 | 10 | 2 |
| 34 | 39.25 | 0.54 | 0.005 | 0.5 | 0.75 | 0.03 | 64 | 0.872852 | 10 | 2 |
| 34 | 39.5 | 0.54 | 0.005 | 0.5 | 0.75 | 0.03 | 64 | 0.878725 | 10 | 2 |
| 34 | 39.75 | 0.54 | 0.005 | 0.5 | 0.75 | 0.03 | 64 | 0.905091 | 10 | 2 |
| 34 | 40 | 0.54 | 0.005 | 0.5 | 0.75 | 0.03 | 64 | 0.917503 | 10 | 2 |
| 34 | 40.25 | 0.54 | 0.005 | 0.5 | 0.75 | 0.03 | 64 | 0.906994 | 10 | 2 |

Fig. 12B

| Crown Angle | Pavillion Angle | Table Size | Culet Size | Star Length | Lower Girdle Length | Girdle Thickness | # of Girdle Facets | DCLR2 | Wavelength Sampling Interval (nm) | Brightness Cutoff Threshold Factor |
|---|---|---|---|---|---|---|---|---|---|---|
| 34 | 40.5 | 0.54 | 0.005 | 0.5 | 0.75 | 0.03 | 64 | 0.869909 | 10 | 2 |
| 34 | 40.75 | 0.54 | 0.005 | 0.5 | 0.75 | 0.03 | 64 | 0.840489 | 10 | 2 |
| 34 | 41 | 0.54 | 0.005 | 0.5 | 0.75 | 0.03 | 64 | 0.804084 | 10 | 2 |
| 34 | 41.25 | 0.54 | 0.005 | 0.5 | 0.75 | 0.03 | 64 | 0.747225 | 10 | 2 |
| 34 | 41.5 | 0.54 | 0.005 | 0.5 | 0.75 | 0.03 | 64 | 0.726934 | 10 | 2 |
| 34 | 41.75 | 0.54 | 0.005 | 0.5 | 0.75 | 0.03 | 64 | 0.721268 | 10 | 2 |
| 34 | 42 | 0.54 | 0.005 | 0.5 | 0.75 | 0.03 | 64 | 0.723958 | 10 | 2 |
| 34 | 42.25 | 0.54 | 0.005 | 0.5 | 0.75 | 0.03 | 64 | 0.712998 | 10 | 2 |
| 34 | 42.5 | 0.54 | 0.005 | 0.5 | 0.75 | 0.03 | 64 | 0.648709 | 10 | 2 |
| 34 | 42.75 | 0.54 | 0.005 | 0.5 | 0.75 | 0.03 | 64 | 0.596706 | 10 | 2 |
| 34 | 43 | 0.54 | 0.005 | 0.5 | 0.75 | 0.03 | 64 | 0.577741 | 10 | 2 |
| 34 | 38 | 0.55 | 0.005 | 0.5 | 0.75 | 0.03 | 64 | 0.814714 | 10 | 2 |
| 34 | 38.25 | 0.55 | 0.005 | 0.5 | 0.75 | 0.03 | 64 | 0.801091 | 10 | 2 |
| 34 | 38.5 | 0.55 | 0.005 | 0.5 | 0.75 | 0.03 | 64 | 0.771957 | 10 | 2 |
| 34 | 38.75 | 0.55 | 0.005 | 0.5 | 0.75 | 0.03 | 64 | 0.771773 | 10 | 2 |
| 34 | 39 | 0.55 | 0.005 | 0.5 | 0.75 | 0.03 | 64 | 0.816006 | 10 | 2 |
| 34 | 39.25 | 0.55 | 0.005 | 0.5 | 0.75 | 0.03 | 64 | 0.860403 | 10 | 2 |
| 34 | 39.5 | 0.55 | 0.005 | 0.5 | 0.75 | 0.03 | 64 | 0.874857 | 10 | 2 |
| 34 | 39.75 | 0.55 | 0.005 | 0.5 | 0.75 | 0.03 | 64 | 0.904774 | 10 | 2 |
| 34 | 40 | 0.55 | 0.005 | 0.5 | 0.75 | 0.03 | 64 | 0.917906 | 10 | 2 |
| 34 | 40.25 | 0.55 | 0.005 | 0.5 | 0.75 | 0.03 | 64 | 0.902202 | 10 | 2 |
| 34 | 40.5 | 0.55 | 0.005 | 0.5 | 0.75 | 0.03 | 64 | 0.865573 | 10 | 2 |
| 34 | 40.75 | 0.55 | 0.005 | 0.5 | 0.75 | 0.03 | 64 | 0.836369 | 10 | 2 |
| 34 | 41 | 0.55 | 0.005 | 0.5 | 0.75 | 0.03 | 64 | 0.797574 | 10 | 2 |
| 34 | 41.25 | 0.55 | 0.005 | 0.5 | 0.75 | 0.03 | 64 | 0.733143 | 10 | 2 |
| 34 | 41.5 | 0.55 | 0.005 | 0.5 | 0.75 | 0.03 | 64 | 0.716023 | 10 | 2 |
| 34 | 41.75 | 0.55 | 0.005 | 0.5 | 0.75 | 0.03 | 64 | 0.704124 | 10 | 2 |
| 34 | 42 | 0.55 | 0.005 | 0.5 | 0.75 | 0.03 | 64 | 0.70276 | 10 | 2 |
| 34 | 42.25 | 0.55 | 0.005 | 0.5 | 0.75 | 0.03 | 64 | 0.698674 | 10 | 2 |
| 34 | 42.5 | 0.55 | 0.005 | 0.5 | 0.75 | 0.03 | 64 | 0.64128 | 10 | 2 |
| 34 | 42.75 | 0.55 | 0.005 | 0.5 | 0.75 | 0.03 | 64 | 0.585637 | 10 | 2 |
| 34 | 43 | 0.55 | 0.005 | 0.5 | 0.75 | 0.03 | 64 | 0.562732 | 10 | 2 |
| 34 | 38 | 0.56 | 0.005 | 0.5 | 0.75 | 0.03 | 64 | 0.810342 | 10 | 2 |
| 34 | 38.25 | 0.56 | 0.005 | 0.5 | 0.75 | 0.03 | 64 | 0.79447 | 10 | 2 |
| 34 | 38.5 | 0.56 | 0.005 | 0.5 | 0.75 | 0.03 | 64 | 0.76528 | 10 | 2 |
| 34 | 38.75 | 0.56 | 0.005 | 0.5 | 0.75 | 0.03 | 64 | 0.765746 | 10 | 2 |
| 34 | 39 | 0.56 | 0.005 | 0.5 | 0.75 | 0.03 | 64 | 0.810468 | 10 | 2 |
| 34 | 39.25 | 0.56 | 0.005 | 0.5 | 0.75 | 0.03 | 64 | 0.851028 | 10 | 2 |
| 34 | 39.5 | 0.56 | 0.005 | 0.5 | 0.75 | 0.03 | 64 | 0.868444 | 10 | 2 |
| 34 | 39.75 | 0.56 | 0.005 | 0.5 | 0.75 | 0.03 | 64 | 0.901324 | 10 | 2 |
| 34 | 40 | 0.56 | 0.005 | 0.5 | 0.75 | 0.03 | 64 | 0.906834 | 10 | 2 |
| 34 | 40.25 | 0.56 | 0.005 | 0.5 | 0.75 | 0.03 | 64 | 0.897934 | 10 | 2 |
| 34 | 40.5 | 0.56 | 0.005 | 0.5 | 0.75 | 0.03 | 64 | 0.863241 | 10 | 2 |
| 34 | 40.75 | 0.56 | 0.005 | 0.5 | 0.75 | 0.03 | 64 | 0.831768 | 10 | 2 |
| 34 | 41 | 0.56 | 0.005 | 0.5 | 0.75 | 0.03 | 64 | 0.794494 | 10 | 2 |
| 34 | 41.25 | 0.56 | 0.005 | 0.5 | 0.75 | 0.03 | 64 | 0.729545 | 10 | 2 |
| 34 | 41.5 | 0.56 | 0.005 | 0.5 | 0.75 | 0.03 | 64 | 0.714573 | 10 | 2 |
| 34 | 41.75 | 0.56 | 0.005 | 0.5 | 0.75 | 0.03 | 64 | 0.700948 | 10 | 2 |
| 34 | 42 | 0.56 | 0.005 | 0.5 | 0.75 | 0.03 | 64 | 0.688704 | 10 | 2 |
| 34 | 42.25 | 0.56 | 0.005 | 0.5 | 0.75 | 0.03 | 64 | 0.6823 | 10 | 2 |
| 34 | 42.5 | 0.56 | 0.005 | 0.5 | 0.75 | 0.03 | 64 | 0.630612 | 10 | 2 |
| 34 | 42.75 | 0.56 | 0.005 | 0.5 | 0.75 | 0.03 | 64 | 0.584443 | 10 | 2 |

Fig. 12C

| Crown Angle | Pavillion Angle | Table Size | Culet Size | Star Length | Lower Girdle Length | Girdle Thickness | # of Girdle Facets | DCLR2 | Wavelength Sampling Interval (nm) | Brightness Cutoff Threshold Factor |
|---|---|---|---|---|---|---|---|---|---|---|
| 34 | 43 | 0.56 | 0.005 | 0.5 | 0.75 | 0.03 | 64 | 0.554585 | 10 | 2 |
| 34 | 38 | 0.57 | 0.005 | 0.5 | 0.75 | 0.03 | 64 | 0.799847 | 10 | 2 |
| 34 | 38.25 | 0.57 | 0.005 | 0.5 | 0.75 | 0.03 | 64 | 0.785196 | 10 | 2 |
| 34 | 38.5 | 0.57 | 0.005 | 0.5 | 0.75 | 0.03 | 64 | 0.757498 | 10 | 2 |
| 34 | 38.75 | 0.57 | 0.005 | 0.5 | 0.75 | 0.03 | 64 | 0.767361 | 10 | 2 |
| 34 | 39 | 0.57 | 0.005 | 0.5 | 0.75 | 0.03 | 64 | 0.813698 | 10 | 2 |
| 34 | 39.25 | 0.57 | 0.005 | 0.5 | 0.75 | 0.03 | 64 | 0.847284 | 10 | 2 |
| 34 | 39.5 | 0.57 | 0.005 | 0.5 | 0.75 | 0.03 | 64 | 0.859142 | 10 | 2 |
| 34 | 39.75 | 0.57 | 0.005 | 0.5 | 0.75 | 0.03 | 64 | 0.893763 | 10 | 2 |
| 34 | 40 | 0.57 | 0.005 | 0.5 | 0.75 | 0.03 | 64 | 0.902374 | 10 | 2 |
| 34 | 40.25 | 0.57 | 0.005 | 0.5 | 0.75 | 0.03 | 64 | 0.892721 | 10 | 2 |
| 34 | 40.5 | 0.57 | 0.005 | 0.5 | 0.75 | 0.03 | 64 | 0.863287 | 10 | 2 |
| 34 | 40.75 | 0.57 | 0.005 | 0.5 | 0.75 | 0.03 | 64 | 0.835853 | 10 | 2 |
| 34 | 41 | 0.57 | 0.005 | 0.5 | 0.75 | 0.03 | 64 | 0.798168 | 10 | 2 |
| 34 | 41.25 | 0.57 | 0.005 | 0.5 | 0.75 | 0.03 | 64 | 0.727064 | 10 | 2 |
| 34 | 41.5 | 0.57 | 0.005 | 0.5 | 0.75 | 0.03 | 64 | 0.711888 | 10 | 2 |
| 34 | 41.75 | 0.57 | 0.005 | 0.5 | 0.75 | 0.03 | 64 | 0.698537 | 10 | 2 |
| 34 | 42 | 0.57 | 0.005 | 0.5 | 0.75 | 0.03 | 64 | 0.68543 | 10 | 2 |
| 34 | 42.25 | 0.57 | 0.005 | 0.5 | 0.75 | 0.03 | 64 | 0.667086 | 10 | 2 |
| 34 | 42.5 | 0.57 | 0.005 | 0.5 | 0.75 | 0.03 | 64 | 0.614259 | 10 | 2 |
| 34 | 42.75 | 0.57 | 0.005 | 0.5 | 0.75 | 0.03 | 64 | 0.578013 | 10 | 2 |
| 34 | 43 | 0.57 | 0.005 | 0.5 | 0.75 | 0.03 | 64 | 0.55583 | 10 | 2 |
| 34 | 38 | 0.58 | 0.005 | 0.5 | 0.75 | 0.03 | 64 | 0.771551 | 10 | 2 |
| 34 | 38.25 | 0.58 | 0.005 | 0.5 | 0.75 | 0.03 | 64 | 0.770125 | 10 | 2 |
| 34 | 38.5 | 0.58 | 0.005 | 0.5 | 0.75 | 0.03 | 64 | 0.750826 | 10 | 2 |
| 34 | 38.75 | 0.58 | 0.005 | 0.5 | 0.75 | 0.03 | 64 | 0.776609 | 10 | 2 |
| 34 | 39 | 0.58 | 0.005 | 0.5 | 0.75 | 0.03 | 64 | 0.822064 | 10 | 2 |
| 34 | 39.25 | 0.58 | 0.005 | 0.5 | 0.75 | 0.03 | 64 | 0.845895 | 10 | 2 |
| 34 | 39.5 | 0.58 | 0.005 | 0.5 | 0.75 | 0.03 | 64 | 0.845349 | 10 | 2 |
| 34 | 39.75 | 0.58 | 0.005 | 0.5 | 0.75 | 0.03 | 64 | 0.880472 | 10 | 2 |
| 34 | 40 | 0.58 | 0.005 | 0.5 | 0.75 | 0.03 | 64 | 0.898266 | 10 | 2 |
| 34 | 40.25 | 0.58 | 0.005 | 0.5 | 0.75 | 0.03 | 64 | 0.895248 | 10 | 2 |
| 34 | 40.5 | 0.58 | 0.005 | 0.5 | 0.75 | 0.03 | 64 | 0.871497 | 10 | 2 |
| 34 | 40.75 | 0.58 | 0.005 | 0.5 | 0.75 | 0.03 | 64 | 0.841391 | 10 | 2 |
| 34 | 41 | 0.58 | 0.005 | 0.5 | 0.75 | 0.03 | 64 | 0.798846 | 10 | 2 |
| 34 | 41.25 | 0.58 | 0.005 | 0.5 | 0.75 | 0.03 | 64 | 0.724288 | 10 | 2 |
| 34 | 41.5 | 0.58 | 0.005 | 0.5 | 0.75 | 0.03 | 64 | 0.708505 | 10 | 2 |
| 34 | 41.75 | 0.58 | 0.005 | 0.5 | 0.75 | 0.03 | 64 | 0.69511 | 10 | 2 |
| 34 | 42 | 0.58 | 0.005 | 0.5 | 0.75 | 0.03 | 64 | 0.683728 | 10 | 2 |
| 34 | 42.25 | 0.58 | 0.005 | 0.5 | 0.75 | 0.03 | 64 | 0.648917 | 10 | 2 |
| 34 | 42.5 | 0.58 | 0.005 | 0.5 | 0.75 | 0.03 | 64 | 0.603822 | 10 | 2 |
| 34 | 42.75 | 0.58 | 0.005 | 0.5 | 0.75 | 0.03 | 64 | 0.566235 | 10 | 2 |
| 34 | 43 | 0.58 | 0.005 | 0.5 | 0.75 | 0.03 | 64 | 0.549192 | 10 | 2 |
| 34 | 38 | 0.59 | 0.005 | 0.5 | 0.75 | 0.03 | 64 | 0.739426 | 10 | 2 |
| 34 | 38.25 | 0.59 | 0.005 | 0.5 | 0.75 | 0.03 | 64 | 0.74518 | 10 | 2 |
| 34 | 38.5 | 0.59 | 0.005 | 0.5 | 0.75 | 0.03 | 64 | 0.754325 | 10 | 2 |
| 34 | 38.75 | 0.59 | 0.005 | 0.5 | 0.75 | 0.03 | 64 | 0.787261 | 10 | 2 |
| 34 | 39 | 0.59 | 0.005 | 0.5 | 0.75 | 0.03 | 64 | 0.831711 | 10 | 2 |
| 34 | 39.25 | 0.59 | 0.005 | 0.5 | 0.75 | 0.03 | 64 | 0.845879 | 10 | 2 |
| 34 | 39.5 | 0.59 | 0.005 | 0.5 | 0.75 | 0.03 | 64 | 0.832287 | 10 | 2 |
| 34 | 39.75 | 0.59 | 0.005 | 0.5 | 0.75 | 0.03 | 64 | 0.875182 | 10 | 2 |
| 34 | 40 | 0.59 | 0.005 | 0.5 | 0.75 | 0.03 | 64 | 0.901357 | 10 | 2 |

Fig. 12D

| Crown Angle | Pavillion Angle | Table Size | Culet Size | Star Length | Lower Girdle Length | Girdle Thickness | # of Girdle Facets | DCLR2 | Wavelength Sampling Interval (nm) | Brightness Cutoff Threshold Factor |
|---|---|---|---|---|---|---|---|---|---|---|
| 34 | 40.25 | 0.59 | 0.005 | 0.5 | 0.75 | 0.03 | 64 | 0.898708 | 10 | 2 |
| 34 | 40.5 | 0.59 | 0.005 | 0.5 | 0.75 | 0.03 | 64 | 0.876342 | 10 | 2 |
| 34 | 40.75 | 0.59 | 0.005 | 0.5 | 0.75 | 0.03 | 64 | 0.846584 | 10 | 2 |
| 34 | 41 | 0.59 | 0.005 | 0.5 | 0.75 | 0.03 | 64 | 0.799008 | 10 | 2 |
| 34 | 41.25 | 0.59 | 0.005 | 0.5 | 0.75 | 0.03 | 64 | 0.720892 | 10 | 2 |
| 34 | 41.5 | 0.59 | 0.005 | 0.5 | 0.75 | 0.03 | 64 | 0.704356 | 10 | 2 |
| 34 | 41.75 | 0.59 | 0.005 | 0.5 | 0.75 | 0.03 | 64 | 0.690144 | 10 | 2 |
| 34 | 42 | 0.59 | 0.005 | 0.5 | 0.75 | 0.03 | 64 | 0.678995 | 10 | 2 |
| 34 | 42.25 | 0.59 | 0.005 | 0.5 | 0.75 | 0.03 | 64 | 0.644305 | 10 | 2 |
| 34 | 42.5 | 0.59 | 0.005 | 0.5 | 0.75 | 0.03 | 64 | 0.601934 | 10 | 2 |
| 34 | 42.75 | 0.59 | 0.005 | 0.5 | 0.75 | 0.03 | 64 | 0.559082 | 10 | 2 |
| 34 | 43 | 0.59 | 0.005 | 0.5 | 0.75 | 0.03 | 64 | 0.538236 | 10 | 2 |
| 34 | 38 | 0.6 | 0.005 | 0.5 | 0.75 | 0.03 | 64 | 0.715373 | 10 | 2 |
| 34 | 38.25 | 0.6 | 0.005 | 0.5 | 0.75 | 0.03 | 64 | 0.72763 | 10 | 2 |
| 34 | 38.5 | 0.6 | 0.005 | 0.5 | 0.75 | 0.03 | 64 | 0.7517 | 10 | 2 |
| 34 | 38.75 | 0.6 | 0.005 | 0.5 | 0.75 | 0.03 | 64 | 0.796534 | 10 | 2 |
| 34 | 39 | 0.6 | 0.005 | 0.5 | 0.75 | 0.03 | 64 | 0.839021 | 10 | 2 |
| 34 | 39.25 | 0.6 | 0.005 | 0.5 | 0.75 | 0.03 | 64 | 0.844216 | 10 | 2 |
| 34 | 39.5 | 0.6 | 0.005 | 0.5 | 0.75 | 0.03 | 64 | 0.829233 | 10 | 2 |
| 34 | 39.75 | 0.6 | 0.005 | 0.5 | 0.75 | 0.03 | 64 | 0.870356 | 10 | 2 |
| 34 | 40 | 0.6 | 0.005 | 0.5 | 0.75 | 0.03 | 64 | 0.900667 | 10 | 2 |
| 34 | 40.25 | 0.6 | 0.005 | 0.5 | 0.76 | 0.03 | 64 | 0.900702 | 10 | 2 |
| 34 | 40.5 | 0.6 | 0.005 | 0.5 | 0.75 | 0.03 | 64 | 0.877821 | 10 | 2 |
| 34 | 40.75 | 0.6 | 0.005 | 0.5 | 0.75 | 0.03 | 64 | 0.850258 | 10 | 2 |
| 34 | 41 | 0.6 | 0.005 | 0.5 | 0.75 | 0.03 | 64 | 0.79833 | 10 | 2 |
| 34 | 41.25 | 0.6 | 0.005 | 0.5 | 0.75 | 0.03 | 64 | 0.7168 | 10 | 2 |
| 34 | 41.5 | 0.6 | 0.005 | 0.5 | 0.75 | 0.03 | 64 | 0.699282 | 10 | 2 |
| 34 | 41.75 | 0.6 | 0.005 | 0.5 | 0.75 | 0.03 | 64 | 0.684268 | 10 | 2 |
| 34 | 42 | 0.6 | 0.005 | 0.5 | 0.75 | 0.03 | 64 | 0.675258 | 10 | 2 |
| 34 | 42.25 | 0.6 | 0.005 | 0.5 | 0.75 | 0.03 | 64 | 0.642043 | 10 | 2 |
| 34 | 42.5 | 0.6 | 0.005 | 0.5 | 0.75 | 0.03 | 64 | 0.602407 | 10 | 2 |
| 34 | 42.75 | 0.6 | 0.005 | 0.5 | 0.75 | 0.03 | 64 | 0.55821 | 10 | 2 |
| 34 | 43 | 0.6 | 0.005 | 0.5 | 0.75 | 0.03 | 64 | 0.529726 | 10 | 2 |
| 34 | 38 | 0.61 | 0.005 | 0.5 | 0.75 | 0.03 | 64 | 0.707912 | 10 | 2 |
| 34 | 38.25 | 0.61 | 0.005 | 0.5 | 0.75 | 0.03 | 64 | 0.713188 | 10 | 2 |
| 34 | 38.5 | 0.61 | 0.005 | 0.5 | 0.75 | 0.03 | 64 | 0.747195 | 10 | 2 |
| 34 | 38.75 | 0.61 | 0.005 | 0.5 | 0.75 | 0.03 | 64 | 0.802606 | 10 | 2 |
| 34 | 39 | 0.61 | 0.005 | 0.5 | 0.75 | 0.03 | 64 | 0.846035 | 10 | 2 |
| 34 | 39.25 | 0.61 | 0.005 | 0.5 | 0.75 | 0.03 | 64 | 0.840474 | 10 | 2 |
| 34 | 39.5 | 0.61 | 0.005 | 0.5 | 0.75 | 0.03 | 64 | 0.826305 | 10 | 2 |
| 34 | 39.75 | 0.61 | 0.005 | 0.5 | 0.75 | 0.03 | 64 | 0.865902 | 10 | 2 |
| 34 | 40 | 0.61 | 0.005 | 0.5 | 0.75 | 0.03 | 64 | 0.897907 | 10 | 2 |
| 34 | 40.25 | 0.61 | 0.005 | 0.5 | 0.75 | 0.03 | 64 | 0.90003 | 10 | 2 |
| 34 | 40.5 | 0.61 | 0.005 | 0.5 | 0.75 | 0.03 | 64 | 0.875527 | 10 | 2 |
| 34 | 40.75 | 0.61 | 0.005 | 0.5 | 0.75 | 0.03 | 64 | 0.852055 | 10 | 2 |
| 34 | 41 | 0.61 | 0.005 | 0.5 | 0.75 | 0.03 | 64 | 0.796219 | 10 | 2 |
| 34 | 41.25 | 0.61 | 0.005 | 0.5 | 0.75 | 0.03 | 64 | 0.711018 | 10 | 2 |
| 34 | 41.5 | 0.61 | 0.005 | 0.5 | 0.75 | 0.03 | 64 | 0.692775 | 10 | 2 |
| 34 | 41.75 | 0.61 | 0.005 | 0.5 | 0.75 | 0.03 | 64 | 0.678103 | 10 | 2 |
| 34 | 42 | 0.61 | 0.005 | 0.5 | 0.75 | 0.03 | 64 | 0.669315 | 10 | 2 |
| 34 | 42.25 | 0.61 | 0.005 | 0.5 | 0.75 | 0.03 | 64 | 0.639022 | 10 | 2 |
| 34 | 42.5 | 0.61 | 0.005 | 0.5 | 0.75 | 0.03 | 64 | 0.602829 | 10 | 2 |

Fig. 12E

| Crown Angle | Pavillion Angle | Table Size | Culet Size | Star Length | Lower Girdle Length | Girdle Thickness | # of Girdle Facets | DCLR2 | Wavelength Sampling Interval (nm) | Brightness Cutoff Threshold Factor |
|---|---|---|---|---|---|---|---|---|---|---|
| 34 | 42.75 | 0.61 | 0.005 | 0.5 | 0.75 | 0.03 | 64 | 0.557297 | 10 | 2 |
| 34 | 43 | 0.61 | 0.005 | 0.5 | 0.75 | 0.03 | 64 | 0.524737 | 10 | 2 |
| 34 | 38 | 0.62 | 0.005 | 0.5 | 0.75 | 0.03 | 64 | 0.706711 | 10 | 2 |
| 34 | 38.25 | 0.62 | 0.005 | 0.5 | 0.75 | 0.03 | 64 | 0.702224 | 10 | 2 |
| 34 | 38.5 | 0.62 | 0.005 | 0.5 | 0.75 | 0.03 | 64 | 0.743246 | 10 | 2 |
| 34 | 38.75 | 0.62 | 0.005 | 0.5 | 0.75 | 0.03 | 64 | 0.80033 | 10 | 2 |
| 34 | 39 | 0.62 | 0.005 | 0.5 | 0.75 | 0.03 | 64 | 0.853166 | 10 | 2 |
| 34 | 39.25 | 0.62 | 0.005 | 0.5 | 0.75 | 0.03 | 64 | 0.837159 | 10 | 2 |
| 34 | 39.5 | 0.62 | 0.005 | 0.5 | 0.75 | 0.03 | 64 | 0.828614 | 10 | 2 |
| 34 | 39.75 | 0.62 | 0.005 | 0.5 | 0.75 | 0.03 | 64 | 0.863602 | 10 | 2 |
| 34 | 40 | 0.62 | 0.005 | 0.5 | 0.75 | 0.03 | 64 | 0.891697 | 10 | 2 |
| 34 | 40.25 | 0.62 | 0.005 | 0.5 | 0.75 | 0.03 | 64 | 0.896706 | 10 | 2 |
| 34 | 40.5 | 0.62 | 0.005 | 0.5 | 0.75 | 0.03 | 64 | 0.872329 | 10 | 2 |
| 34 | 40.75 | 0.62 | 0.005 | 0.5 | 0.75 | 0.03 | 64 | 0.851519 | 10 | 2 |
| 34 | 41 | 0.62 | 0.005 | 0.5 | 0.75 | 0.03 | 64 | 0.79316 | 10 | 2 |
| 34 | 41.25 | 0.62 | 0.005 | 0.5 | 0.75 | 0.03 | 64 | 0.703072 | 10 | 2 |
| 34 | 41.5 | 0.62 | 0.005 | 0.5 | 0.75 | 0.03 | 64 | 0.685047 | 10 | 2 |
| 34 | 41.75 | 0.62 | 0.005 | 0.5 | 0.75 | 0.03 | 64 | 0.671654 | 10 | 2 |
| 34 | 42 | 0.62 | 0.005 | 0.5 | 0.75 | 0.03 | 64 | 0.663322 | 10 | 2 |
| 34 | 42.25 | 0.62 | 0.005 | 0.5 | 0.75 | 0.03 | 64 | 0.633063 | 10 | 2 |
| 34 | 42.5 | 0.62 | 0.005 | 0.5 | 0.75 | 0.03 | 64 | 0.601153 | 10 | 2 |
| 34 | 42.75 | 0.62 | 0.005 | 0.5 | 0.75 | 0.03 | 64 | 0.554241 | 10 | 2 |
| 34 | 43 | 0.62 | 0.005 | 0.5 | 0.75 | 0.03 | 64 | 0.520811 | 10 | 2 |
| 34 | 38 | 0.63 | 0.005 | 0.5 | 0.75 | 0.03 | 64 | 0.707739 | 10 | 2 |
| 34 | 38.25 | 0.63 | 0.005 | 0.5 | 0.75 | 0.03 | 64 | 0.710567 | 10 | 2 |
| 34 | 38.5 | 0.63 | 0.005 | 0.5 | 0.75 | 0.03 | 64 | 0.737919 | 10 | 2 |
| 34 | 38.75 | 0.63 | 0.005 | 0.5 | 0.75 | 0.03 | 64 | 0.796747 | 10 | 2 |
| 34 | 39 | 0.63 | 0.005 | 0.5 | 0.75 | 0.03 | 64 | 0.848361 | 10 | 2 |
| 34 | 39.25 | 0.63 | 0.005 | 0.5 | 0.75 | 0.03 | 64 | 0.836786 | 10 | 2 |
| 34 | 39.5 | 0.63 | 0.005 | 0.5 | 0.75 | 0.03 | 64 | 0.825664 | 10 | 2 |
| 34 | 39.75 | 0.63 | 0.005 | 0.5 | 0.75 | 0.03 | 64 | 0.860696 | 10 | 2 |
| 34 | 40 | 0.63 | 0.005 | 0.5 | 0.75 | 0.03 | 64 | 0.884747 | 10 | 2 |
| 34 | 40.25 | 0.63 | 0.005 | 0.5 | 0.75 | 0.03 | 64 | 0.889581 | 10 | 2 |
| 34 | 40.5 | 0.63 | 0.005 | 0.5 | 0.75 | 0.03 | 64 | 0.868553 | 10 | 2 |
| 34 | 40.75 | 0.63 | 0.005 | 0.5 | 0.75 | 0.03 | 64 | 0.847611 | 10 | 2 |
| 34 | 41 | 0.63 | 0.005 | 0.5 | 0.75 | 0.03 | 64 | 0.789609 | 10 | 2 |
| 34 | 41.25 | 0.63 | 0.005 | 0.5 | 0.75 | 0.03 | 64 | 0.693305 | 10 | 2 |
| 34 | 41.5 | 0.63 | 0.005 | 0.5 | 0.75 | 0.03 | 64 | 0.677208 | 10 | 2 |
| 34 | 41.75 | 0.63 | 0.005 | 0.5 | 0.75 | 0.03 | 64 | 0.664778 | 10 | 2 |
| 34 | 42 | 0.63 | 0.005 | 0.5 | 0.75 | 0.03 | 64 | 0.657323 | 10 | 2 |
| 34 | 42.25 | 0.63 | 0.005 | 0.5 | 0.75 | 0.03 | 64 | 0.623253 | 10 | 2 |
| 34 | 42.5 | 0.63 | 0.005 | 0.5 | 0.75 | 0.03 | 64 | 0.593124 | 10 | 2 |
| 34 | 42.75 | 0.63 | 0.005 | 0.5 | 0.75 | 0.03 | 64 | 0.551869 | 10 | 2 |
| 34 | 43 | 0.63 | 0.005 | 0.5 | 0.75 | 0.03 | 64 | 0.516824 | 10 | 2 |
| 34 | 38 | 0.64 | 0.005 | 0.5 | 0.75 | 0.03 | 64 | 0.710207 | 10 | 2 |
| 34 | 38.25 | 0.64 | 0.005 | 0.5 | 0.75 | 0.03 | 64 | 0.723086 | 10 | 2 |
| 34 | 38.5 | 0.64 | 0.005 | 0.5 | 0.75 | 0.03 | 64 | 0.732374 | 10 | 2 |
| 34 | 38.75 | 0.64 | 0.005 | 0.5 | 0.75 | 0.03 | 64 | 0.761999 | 10 | 2 |
| 34 | 39 | 0.64 | 0.005 | 0.5 | 0.75 | 0.03 | 64 | 0.840977 | 10 | 2 |
| 34 | 39.25 | 0.64 | 0.005 | 0.5 | 0.75 | 0.03 | 64 | 0.822409 | 10 | 2 |
| 34 | 39.5 | 0.64 | 0.005 | 0.5 | 0.75 | 0.03 | 64 | 0.828563 | 10 | 2 |
| 34 | 39.75 | 0.64 | 0.005 | 0.5 | 0.75 | 0.03 | 64 | 0.856142 | 10 | 2 |

Fig. 12F

| Crown Angle | Pavillion Angle | Table Size | Culet Size | Star Length | Lower Girdle Length | Girdle Thickness | # of Girdle Facets | DCLR2 | Wavelength Sampling Interval (nm) | Brightness Cutoff Threshold Factor |
|---|---|---|---|---|---|---|---|---|---|---|
| 34 | 40 | 0.64 | 0.005 | 0.5 | 0.75 | 0.03 | 64 | 0.879889 | 10 | 2 |
| 34 | 40.25 | 0.64 | 0.005 | 0.5 | 0.75 | 0.03 | 64 | 0.879822 | 10 | 2 |
| 34 | 40.5 | 0.64 | 0.005 | 0.5 | 0.75 | 0.03 | 64 | 0.863085 | 10 | 2 |
| 34 | 40.75 | 0.64 | 0.005 | 0.5 | 0.75 | 0.03 | 64 | 0.840276 | 10 | 2 |
| 34 | 41 | 0.64 | 0.005 | 0.5 | 0.75 | 0.03 | 64 | 0.784399 | 10 | 2 |
| 34 | 41.25 | 0.64 | 0.005 | 0.5 | 0.75 | 0.03 | 64 | 0.683366 | 10 | 2 |
| 34 | 41.5 | 0.64 | 0.005 | 0.5 | 0.75 | 0.03 | 64 | 0.669707 | 10 | 2 |
| 34 | 41.75 | 0.64 | 0.005 | 0.5 | 0.75 | 0.03 | 64 | 0.65738 | 10 | 2 |
| 34 | 42 | 0.64 | 0.005 | 0.5 | 0.75 | 0.03 | 64 | 0.646081 | 10 | 2 |
| 34 | 42.25 | 0.64 | 0.005 | 0.5 | 0.75 | 0.03 | 64 | 0.613999 | 10 | 2 |
| 34 | 42.5 | 0.64 | 0.005 | 0.5 | 0.75 | 0.03 | 64 | 0.581597 | 10 | 2 |
| 34 | 42.75 | 0.64 | 0.005 | 0.5 | 0.75 | 0.03 | 64 | 0.545589 | 10 | 2 |
| 34 | 43 | 0.64 | 0.005 | 0.5 | 0.75 | 0.03 | 64 | 0.510111 | 10 | 2 |
| 34 | 38 | 0.65 | 0.005 | 0.5 | 0.75 | 0.03 | 64 | 0.715558 | 10 | 2 |
| 34 | 38.25 | 0.65 | 0.005 | 0.5 | 0.75 | 0.03 | 64 | 0.736196 | 10 | 2 |
| 34 | 38.5 | 0.65 | 0.005 | 0.5 | 0.75 | 0.03 | 64 | 0.745934 | 10 | 2 |
| 34 | 38.75 | 0.65 | 0.005 | 0.5 | 0.75 | 0.03 | 64 | 0.785599 | 10 | 2 |
| 34 | 39 | 0.65 | 0.005 | 0.5 | 0.75 | 0.03 | 64 | 0.833372 | 10 | 2 |
| 34 | 39.25 | 0.65 | 0.005 | 0.5 | 0.75 | 0.03 | 64 | 0.802325 | 10 | 2 |
| 34 | 39.5 | 0.65 | 0.005 | 0.5 | 0.75 | 0.03 | 64 | 0.822724 | 10 | 2 |
| 34 | 39.75 | 0.65 | 0.005 | 0.5 | 0.75 | 0.03 | 64 | 0.85561 | 10 | 2 |
| 34 | 40 | 0.65 | 0.005 | 0.5 | 0.75 | 0.03 | 64 | 0.874749 | 10 | 2 |
| 34 | 40.25 | 0.65 | 0.005 | 0.5 | 0.75 | 0.03 | 64 | 0.871053 | 10 | 2 |
| 34 | 40.5 | 0.65 | 0.005 | 0.5 | 0.75 | 0.03 | 64 | 0.856115 | 10 | 2 |
| 34 | 40.75 | 0.65 | 0.005 | 0.5 | 0.75 | 0.03 | 64 | 0.831199 | 10 | 2 |
| 34 | 41 | 0.65 | 0.005 | 0.5 | 0.75 | 0.03 | 64 | 0.775398 | 10 | 2 |
| 34 | 41.25 | 0.65 | 0.005 | 0.5 | 0.75 | 0.03 | 64 | 0.674185 | 10 | 2 |
| 34 | 41.5 | 0.65 | 0.005 | 0.5 | 0.75 | 0.03 | 64 | 0.66234 | 10 | 2 |
| 34 | 41.75 | 0.65 | 0.005 | 0.5 | 0.75 | 0.03 | 64 | 0.649616 | 10 | 2 |
| 34 | 42 | 0.65 | 0.005 | 0.5 | 0.75 | 0.03 | 64 | 0.625126 | 10 | 2 |
| 34 | 42.25 | 0.65 | 0.005 | 0.5 | 0.75 | 0.03 | 64 | 0.606534 | 10 | 2 |
| 34 | 42.5 | 0.65 | 0.005 | 0.5 | 0.75 | 0.03 | 64 | 0.573906 | 10 | 2 |
| 34 | 42.75 | 0.65 | 0.005 | 0.5 | 0.75 | 0.03 | 64 | 0.538178 | 10 | 2 |
| 34 | 43 | 0.65 | 0.005 | 0.5 | 0.75 | 0.03 | 64 | 0.510028 | 10 | 2 |

Fig. 23

| | | Table Size | | | | | | DCLR 4 | | |
|---|---|---|---|---|---|---|---|---|---|---|
| 34 | 40.5 | 0.45 | 0.005 | 0.5 | 0.75 | 0.03 | 64 | 6.282853 | 10 | 4 |
| 34 | 40.5 | 0.46 | 0.005 | 0.5 | 0.75 | 0.03 | 64 | 6.143581 | 10 | 4 |
| 34 | 40.5 | 0.47 | 0.005 | 0.5 | 0.75 | 0.03 | 64 | 6.036705 | 10 | 4 |
| 34 | 40.5 | 0.48 | 0.005 | 0.5 | 0.75 | 0.03 | 64 | 5.914933 | 10 | 4 |
| 34 | 40.5 | 0.49 | 0.005 | 0.5 | 0.75 | 0.03 | 64 | 5.823898 | 10 | 4 |
| 34 | 40.5 | 0.5 | 0.005 | 0.5 | 0.75 | 0.03 | 64 | 5.744799 | 10 | 4 |
| 34 | 40.5 | 0.51 | 0.005 | 0.5 | 0.75 | 0.03 | 64 | 5.69719 | 10 | 4 |
| 34 | 40.5 | 0.52 | 0.005 | 0.5 | 0.75 | 0.03 | 64 | 5.719851 | 10 | 4 |
| 34 | 40.5 | 0.53 | 0.005 | 0.5 | 0.75 | 0.03 | 64 | 5.667448 | 10 | 4 |
| 34 | 40.5 | 0.54 | 0.005 | 0.5 | 0.75 | 0.03 | 64 | 5.599147 | 10 | 4 |
| 34 | 40.5 | 0.55 | 0.005 | 0.5 | 0.75 | 0.03 | 64 | 5.428893 | 10 | 4 |
| 34 | 40.5 | 0.56 | 0.005 | 0.5 | 0.75 | 0.03 | 64 | 5.266954 | 10 | 4 |
| 34 | 40.5 | 0.57 | 0.005 | 0.5 | 0.75 | 0.03 | 64 | 5.037557 | 10 | 4 |
| 34 | 40.5 | 0.58 | 0.005 | 0.5 | 0.75 | 0.03 | 64 | 4.934068 | 10 | 4 |
| 34 | 40.5 | 0.59 | 0.005 | 0.5 | 0.75 | 0.03 | 64 | 4.934716 | 10 | 4 |
| 34 | 40.5 | 0.6 | 0.005 | 0.5 | 0.75 | 0.03 | 64 | 4.923382 | 10 | 4 |
| 34 | 40.5 | 0.61 | 0.005 | 0.5 | 0.75 | 0.03 | 64 | 4.922016 | 10 | 4 |
| 34 | 40.5 | 0.62 | 0.005 | 0.5 | 0.75 | 0.03 | 64 | 4.819245 | 10 | 4 |
| 34 | 40.5 | 0.63 | 0.005 | 0.5 | 0.75 | 0.03 | 64 | 4.80074 | 10 | 4 |
| 34 | 40.5 | 0.64 | 0.005 | 0.5 | 0.75 | 0.03 | 64 | 4.76932 | 10 | 4 |
| 34 | 40.5 | 0.65 | 0.005 | 0.5 | 0.75 | 0.03 | 64 | 4.686667 | 10 | 4 |
| 34 | 40.5 | 0.66 | 0.005 | 0.5 | 0.75 | 0.03 | 64 | 4.56382 | 10 | 4 |
| 34 | 40.5 | 0.67 | 0.005 | 0.5 | 0.75 | 0.03 | 64 | 4.486941 | 10 | 4 |
| 34 | 40.5 | 0.68 | 0.005 | 0.5 | 0.75 | 0.03 | 64 | 4.509926 | 10 | 4 |
| 34 | 40.5 | 0.69 | 0.005 | 0.5 | 0.75 | 0.03 | 64 | 4.57587 | 10 | 4 |
| 34 | 40.5 | 0.7 | 0.005 | 0.5 | 0.75 | 0.03 | 64 | 4.516473 | 10 | 4 |
| 34 | 40.5 | 0.71 | 0.005 | 0.5 | 0.75 | 0.03 | 64 | 4.50992 | 10 | 4 |
| 34 | 40.5 | 0.72 | 0.005 | 0.5 | 0.75 | 0.03 | 64 | 4.644815 | 10 | 4 |
| 34 | 40.5 | 0.73 | 0.005 | 0.5 | 0.75 | 0.03 | 64 | 4.482011 | 10 | 4 |
| 34 | 40.5 | 0.74 | 0.005 | 0.5 | 0.75 | 0.03 | 64 | 4.410741 | 10 | 4 |
| 34 | 40.5 | 0.75 | 0.005 | 0.5 | 0.75 | 0.03 | 64 | 4.096369 | 10 | 4 |

Fig. 24

| | | | | | LG | | | LG | DCLR4 | | |
|---|---|---|---|---|---|---|---|---|---|---|---|
| 34 | 40.5 | 0.56 | 0.005 | 0.5 | 0.45 | 0.03 | 64 | 0.45 | 3.624814 | 10 | 4 |
| 34 | 40.5 | 0.56 | 0.005 | 0.5 | 0.5 | 0.03 | 64 | 0.5 | 3.768429 | 10 | 4 |
| 34 | 40.5 | 0.56 | 0.005 | 0.5 | 0.55 | 0.03 | 64 | 0.55 | 3.976636 | 10 | 4 |
| 34 | 40.5 | 0.56 | 0.005 | 0.5 | 0.6 | 0.03 | 64 | 0.6 | 4.319326 | 10 | 4 |
| 34 | 40.5 | 0.56 | 0.005 | 0.5 | 0.65 | 0.03 | 64 | 0.65 | 4.695213 | 10 | 4 |
| 34 | 40.5 | 0.56 | 0.005 | 0.5 | 0.7 | 0.03 | 64 | 0.7 | 4.955746 | 10 | 4 |
| 34 | 40.5 | 0.56 | 0.005 | 0.5 | 0.75 | 0.03 | 64 | 0.75 | 5.266954 | 10 | 4 |
| 34 | 40.5 | 0.56 | 0.005 | 0.5 | 0.8 | 0.03 | 64 | 0.8 | 5.418637 | 10 | 4 |
| 34 | 40.5 | 0.56 | 0.005 | 0.5 | 0.85 | 0.03 | 64 | 0.85 | 5.623973 | 10 | 4 |
| 34 | 40.5 | 0.56 | 0.005 | 0.5 | 0.9 | 0.03 | 64 | 0.9 | 5.607077 | 10 | 4 |
| 34 | 40.5 | 0.56 | 0.005 | 0.5 | 0.95 | 0.03 | 64 | 0.95 | 5.548603 | 10 | 4 |
| | | | | | | | | LG | DCLR 3 | | |
| 34 | 40.5 | 0.56 | 0.005 | 0.5 | 0.45 | 0.03 | 64 | 0.45 | 1.70454 | 10 | 3 |
| 34 | 40.5 | 0.56 | 0.005 | 0.5 | 0.5 | 0.03 | 64 | 0.5 | 1.831406 | 10 | 3 |
| 34 | 40.5 | 0.56 | 0.005 | 0.5 | 0.55 | 0.03 | 64 | 0.55 | 1.874035 | 10 | 3 |
| 34 | 40.5 | 0.56 | 0.005 | 0.5 | 0.6 | 0.03 | 64 | 0.6 | 1.889197 | 10 | 3 |
| 34 | 40.5 | 0.56 | 0.005 | 0.5 | 0.65 | 0.03 | 64 | 0.65 | 2.057588 | 10 | 3 |
| 34 | 40.5 | 0.56 | 0.005 | 0.5 | 0.7 | 0.03 | 64 | 0.7 | 2.188972 | 10 | 3 |
| 34 | 40.5 | 0.56 | 0.005 | 0.5 | 0.75 | 0.03 | 64 | 0.75 | 2.345421 | 10 | 3 |
| 34 | 40.5 | 0.56 | 0.005 | 0.5 | 0.8 | 0.03 | 64 | 0.8 | 2.378217 | 10 | 3 |
| 34 | 40.5 | 0.56 | 0.005 | 0.5 | 0.85 | 0.03 | 64 | 0.85 | 2.365716 | 10 | 3 |
| 34 | 40.5 | 0.56 | 0.005 | 0.5 | 0.9 | 0.03 | 64 | 0.9 | 2.272546 | 10 | 3 |
| 34 | 40.5 | 0.56 | 0.005 | 0.5 | 0.95 | 0.03 | 64 | 0.95 | 2.09303 | 10 | 3 |
| | | | | | | | | LG | DCLR 2 | | |
| 34 | 40.5 | 0.56 | 0.005 | 0.5 | 0.45 | 0.03 | 64 | 0.45 | 0.6471 | 10 | 2 |
| 34 | 40.5 | 0.56 | 0.005 | 0.5 | 0.5 | 0.03 | 64 | 0.5 | 0.677515 | 10 | 2 |
| 34 | 40.5 | 0.56 | 0.005 | 0.5 | 0.55 | 0.03 | 64 | 0.55 | 0.679215 | 10 | 2 |
| 34 | 40.5 | 0.56 | 0.005 | 0.5 | 0.6 | 0.03 | 64 | 0.6 | 0.690058 | 10 | 2 |
| 34 | 40.5 | 0.56 | 0.005 | 0.5 | 0.65 | 0.03 | 64 | 0.65 | 0.708702 | 10 | 2 |
| 34 | 40.5 | 0.56 | 0.005 | 0.5 | 0.7 | 0.03 | 64 | 0.7 | 0.781613 | 10 | 2 |
| 34 | 40.5 | 0.56 | 0.005 | 0.5 | 0.75 | 0.03 | 64 | 0.75 | 0.863241 | 10 | 2 |
| 34 | 40.5 | 0.56 | 0.005 | 0.5 | 0.8 | 0.03 | 64 | 0.8 | 0.905219 | 10 | 2 |
| 34 | 40.5 | 0.56 | 0.005 | 0.5 | 0.85 | 0.03 | 64 | 0.85 | 0.890675 | 10 | 2 |
| 34 | 40.5 | 0.56 | 0.005 | 0.5 | 0.9 | 0.03 | 64 | 0.9 | 0.85178 | 10 | 2 |
| 34 | 40.5 | 0.56 | 0.005 | 0.5 | 0.95 | 0.03 | 64 | 0.95 | 0.79999 | 10 | 2 |

DCLR versus Culet Size

Fig. 26A

| | | Culet Size | | | | | Culet Size | DCLR4 | DCLR3 | DCLR2 | | |
|---|---|---|---|---|---|---|---|---|---|---|---|---|
| 34 | 41 | 0.56 | 0 | 0.5 | 0.75 | 0.03 | 64 | 0 | 5.284192 | 2.355428 | 0.868906 | 10 | 4 |
| 34 | 41 | 0.56 | 0.01 | 0.5 | 0.75 | 0.03 | 64 | 0.01 | 5.25454 | 2.335876 | 0.857219 | 10 | 4 |
| 34 | 41 | 0.56 | 0.02 | 0.5 | 0.75 | 0.03 | 64 | 0.02 | 5.213373 | 2.316395 | 0.844447 | 10 | 4 |
| 34 | 41 | 0.56 | 0.03 | 0.5 | 0.75 | 0.03 | 64 | 0.03 | 5.174934 | 2.293616 | 0.830896 | 10 | 4 |
| 34 | 41 | 0.56 | 0.04 | 0.5 | 0.75 | 0.03 | 64 | 0.04 | 5.119718 | 2.258964 | 0.816658 | 10 | 4 |
| 34 | 41 | 0.56 | 0.05 | 0.5 | 0.75 | 0.03 | 64 | 0.05 | 5.046029 | 2.224922 | 0.802315 | 10 | 4 |
| 34 | 41 | 0.56 | 0.06 | 0.5 | 0.75 | 0.03 | 64 | 0.06 | 4.980114 | 2.194238 | 0.787939 | 10 | 4 |
| 34 | 41 | 0.56 | 0.07 | 0.5 | 0.75 | 0.03 | 64 | 0.07 | 4.915477 | 2.168457 | 0.772775 | 10 | 4 |
| 34 | 41 | 0.56 | 0.08 | 0.5 | 0.75 | 0.03 | 64 | 0.08 | 4.875271 | 2.149683 | 0.756819 | 10 | 4 |
| 34 | 41 | 0.56 | 0.09 | 0.5 | 0.75 | 0.03 | 64 | 0.09 | 4.826089 | 2.133423 | 0.740934 | 10 | 4 |
| 34 | 41 | 0.56 | 0.1 | 0.5 | 0.75 | 0.03 | 64 | 0.1 | 4.78476 | 2.111817 | 0.726574 | 10 | 4 |
| 34 | 41 | 0.56 | 0.11 | 0.5 | 0.75 | 0.03 | 64 | 0.11 | 4.761126 | 2.0903 | 0.713786 | 10 | 4 |
| 34 | 41 | 0.56 | 0.12 | 0.5 | 0.75 | 0.03 | 64 | 0.12 | 4.744847 | 2.065745 | 0.702585 | 10 | 4 |
| 34 | 41 | 0.56 | 0.13 | 0.5 | 0.75 | 0.03 | 64 | 0.13 | 4.717384 | 2.049073 | 0.693117 | 10 | 4 |
| 34 | 41 | 0.56 | 0.14 | 0.5 | 0.75 | 0.03 | 64 | 0.14 | 4.671139 | 2.018712 | 0.686312 | 10 | 4 |
| 34 | 41 | 0.56 | 0.15 | 0.5 | 0.75 | 0.03 | 64 | 0.15 | 4.604082 | 1.974939 | 0.680394 | 10 | 4 |
| 34 | 41 | 0.56 | 0.16 | 0.5 | 0.75 | 0.03 | 64 | 0.16 | 4.520027 | 1.921601 | 0.67369 | 10 | 4 |
| 34 | 41 | 0.56 | 0.17 | 0.5 | 0.75 | 0.03 | 64 | 0.17 | 4.449352 | 1.870071 | 0.667312 | 10 | 4 |
| 34 | 41 | 0.56 | 0.18 | 0.5 | 0.75 | 0.03 | 64 | 0.18 | 4.357821 | 1.830536 | 0.662123 | 10 | 4 |
| 34 | 41 | 0.56 | 0.19 | 0.5 | 0.75 | 0.03 | 64 | 0.19 | 4.306298 | 1.802996 | 0.656936 | 10 | 4 |
| 34 | 41 | 0.56 | 0.2 | 0.5 | 0.75 | 0.03 | 64 | 0.2 | 4.264232 | 1.795603 | 0.650635 | 10 | 4 |
| | | | | | | | | | DCLR3 | | | |
| 34 | 41 | 0.56 | 0 | 0.5 | 0.75 | 0.03 | 64 | 0 | 2.355428 | | 10 | 3 |
| 34 | 41 | 0.56 | 0.01 | 0.5 | 0.75 | 0.03 | 64 | 0.01 | 2.335876 | | 10 | 3 |
| 34 | 41 | 0.56 | 0.02 | 0.5 | 0.75 | 0.03 | 64 | 0.02 | 2.316395 | | 10 | 3 |
| 34 | 41 | 0.56 | 0.03 | 0.5 | 0.75 | 0.03 | 64 | 0.03 | 2.293616 | | 10 | 3 |
| 34 | 41 | 0.56 | 0.04 | 0.5 | 0.75 | 0.03 | 64 | 0.04 | 2.258964 | | 10 | 3 |
| 34 | 41 | 0.56 | 0.05 | 0.5 | 0.75 | 0.03 | 64 | 0.05 | 2.224922 | | 10 | 3 |
| 34 | 41 | 0.56 | 0.06 | 0.5 | 0.75 | 0.03 | 64 | 0.06 | 2.194238 | | 10 | 3 |
| 34 | 41 | 0.56 | 0.07 | 0.5 | 0.75 | 0.03 | 64 | 0.07 | 2.168457 | | 10 | 3 |
| 34 | 41 | 0.56 | 0.08 | 0.5 | 0.75 | 0.03 | 64 | 0.08 | 2.149683 | | 10 | 3 |
| 34 | 41 | 0.56 | 0.09 | 0.5 | 0.75 | 0.03 | 64 | 0.09 | 2.133423 | | 10 | 3 |
| 34 | 41 | 0.56 | 0.1 | 0.5 | 0.75 | 0.03 | 64 | 0.1 | 2.111817 | | 10 | 3 |
| 34 | 41 | 0.56 | 0.11 | 0.5 | 0.75 | 0.03 | 64 | 0.11 | 2.0903 | | 10 | 3 |
| 34 | 41 | 0.56 | 0.12 | 0.5 | 0.75 | 0.03 | 64 | 0.12 | 2.065745 | | 10 | 3 |
| 34 | 41 | 0.56 | 0.13 | 0.5 | 0.75 | 0.03 | 64 | 0.13 | 2.049073 | | 10 | 3 |
| 34 | 41 | 0.56 | 0.14 | 0.5 | 0.75 | 0.03 | 64 | 0.14 | 2.018712 | | 10 | 3 |
| 34 | 41 | 0.56 | 0.15 | 0.5 | 0.75 | 0.03 | 64 | 0.15 | 1.974939 | | 10 | 3 |
| 34 | 41 | 0.56 | 0.16 | 0.5 | 0.75 | 0.03 | 64 | 0.16 | 1.921601 | | 10 | 3 |
| 34 | 41 | 0.56 | 0.17 | 0.5 | 0.75 | 0.03 | 64 | 0.17 | 1.870071 | | 10 | 3 |
| 34 | 41 | 0.56 | 0.18 | 0.5 | 0.75 | 0.03 | 64 | 0.18 | 1.830536 | | 10 | 3 |
| 34 | 41 | 0.56 | 0.19 | 0.5 | 0.75 | 0.03 | 64 | 0.19 | 1.802996 | | 10 | 3 |
| 34 | 41 | 0.56 | 0.2 | 0.5 | 0.75 | 0.03 | 64 | 0.2 | 1.795603 | | 10 | 3 |

| Fig. 26B | | | | | | | | | | | | |
|---|---|---|---|---|---|---|---|---|---|---|---|---|
| | | | | | | | | DCLR2 | | | | |
| 34 | 41 | 0.56 | 0 | 0.5 | 0.75 | 0.03 | 64 | 0 | 0.868906 | 10 | 2 | |
| 34 | 41 | 0.56 | 0.01 | 0.5 | 0.75 | 0.03 | 64 | 0.01 | 0.857219 | 10 | 2 | |
| 34 | 41 | 0.56 | 0.02 | 0.5 | 0.75 | 0.03 | 64 | 0.02 | 0.844447 | 10 | 2 | |
| 34 | 41 | 0.56 | 0.03 | 0.5 | 0.75 | 0.03 | 64 | 0.03 | 0.830896 | 10 | 2 | |
| 34 | 41 | 0.56 | 0.04 | 0.5 | 0.75 | 0.03 | 64 | 0.04 | 0.816658 | 10 | 2 | |
| 34 | 41 | 0.56 | 0.05 | 0.5 | 0.75 | 0.03 | 64 | 0.05 | 0.802315 | 10 | 2 | |
| 34 | 41 | 0.56 | 0.06 | 0.5 | 0.75 | 0.03 | 64 | 0.06 | 0.787939 | 10 | 2 | |
| 34 | 41 | 0.56 | 0.07 | 0.5 | 0.75 | 0.03 | 64 | 0.07 | 0.772775 | 10 | 2 | |
| 34 | 41 | 0.56 | 0.08 | 0.5 | 0.75 | 0.03 | 64 | 0.08 | 0.756819 | 10 | 2 | |
| 34 | 41 | 0.56 | 0.09 | 0.5 | 0.75 | 0.03 | 64 | 0.09 | 0.740934 | 10 | 2 | |
| 34 | 41 | 0.56 | 0.1 | 0.5 | 0.75 | 0.03 | 64 | 0.1 | 0.726574 | 10 | 2 | |
| 34 | 41 | 0.56 | 0.11 | 0.5 | 0.75 | 0.03 | 64 | 0.11 | 0.713786 | 10 | 2 | |
| 34 | 41 | 0.56 | 0.12 | 0.5 | 0.75 | 0.03 | 64 | 0.12 | 0.702585 | 10 | 2 | |
| 34 | 41 | 0.56 | 0.13 | 0.5 | 0.75 | 0.03 | 64 | 0.13 | 0.693117 | 10 | 2 | |
| 34 | 41 | 0.56 | 0.14 | 0.5 | 0.75 | 0.03 | 64 | 0.14 | 0.686312 | 10 | 2 | |
| 34 | 41 | 0.56 | 0.15 | 0.5 | 0.75 | 0.03 | 64 | 0.15 | 0.680394 | 10 | 2 | |
| 34 | 41 | 0.56 | 0.16 | 0.5 | 0.75 | 0.03 | 64 | 0.16 | 0.67369 | 10 | 2 | |
| 34 | 41 | 0.56 | 0.17 | 0.5 | 0.75 | 0.03 | 64 | 0.17 | 0.667312 | 10 | 2 | |
| 34 | 41 | 0.56 | 0.18 | 0.5 | 0.75 | 0.03 | 64 | 0.18 | 0.662123 | 10 | 2 | |
| 34 | 41 | 0.56 | 0.19 | 0.5 | 0.75 | 0.03 | 64 | 0.19 | 0.656936 | 10 | 2 | |
| 34 | 41 | 0.56 | 0.2 | 0.5 | 0.75 | 0.03 | 64 | 0.2 | 0.650633 | 10 | 2 | |

SYSTEM AND METHODS FOR EVALUATING THE APPEARANCE OF A GEMSTONE

BACKGROUND OF THE INVENTION

The quality and value of faceted gem diamonds are often described in terms of the "four C's": carat weight, color, clarity, and cut. Weight is the most objective, because it is measured directly on a balance. Color and clarity are factors for which grading standards have been established by GIA, among others. Clamor for the standardization of cut, and calls for a simple cut grading system, have been heard sporadically over the last 27 years, gaining strength recently (Shor, 1993, 1997; Nestlebaum, 1996, 1997). Unlike color and clarity, for which diamond trading, consistent teaching, and laboratory practice have created a general consensus, there are a number of different systems for grading cut in round brilliants. As described in greater detail herein, these systems are based on relatively simple assumptions about the relationship between the proportions and appearance of the round brilliant diamond. Inherent in these systems is the premise that there is one set (or a narrow range) of preferred proportions for round brilliants, and that any deviation from this set of proportions diminishes the attractiveness of a diamond. However, no system described to date has adequately accounted for the rather complex relationship between cut proportions and two of the features within the canonical description of diamond appearance—fire and scintillation.

Diamond manufacturing has undergone considerable change during the past century. For the most part, diamonds have been cut within very close proportion tolerances, both to save weight while maximizing appearance and to account for local market preferences (Caspi, 1997). Differences in proportions can produce noticeable differences in appearance in round-brilliant-cut diamonds. Within this single cutting style, there is substantial debate—and some strongly held views—about which proportions yield the best face-up appearance (Federman, 1997). Yet face-up appearance depends as well on many intrinsic physical and optical properties of diamond as a material, and on the way these properties govern the paths of light through the faceted gemstone. (Other properties particular to each stone, such as polish quality, symmetry, and the presence of inclusions also effect the paths of light through the gemstone).

Diamond appearance is described chiefly in terms of brilliance (white light returned through the crown), fire (the visible extent of light dispersion into spectral colors), and scintillation (flashes of light reflected from the crown). Yet each of these terms cannot be expressed mathematically without making some assumptions and qualifications. Many aspects of diamond evaluation with respect to brilliance are described in "Modeling the Appearance of the Round Brilliant Cut Diamond: An Analysis of Brilliance." Gems & Gemology, Vol. 34, No. 3, pp. 158–183 (which is hereby incorporated by reference).

Several analyses of the round brilliant cut have been published, starting with Wade (1916). Best known are Tolkowsky's (1919) calculations of the proportions that he believed would optimize the appearance of the round-brilliant-cut diamond. However, Tolkowsky's calculations involved two-dimensional images as graphical and mathematical models. These were used to solve sets of relatively simple equations that described what was considered to be the brilliance of a polished round brilliant diamond. (Tolkowsky did include a simple analysis of fire, but it was not central to his model).

The issues raised by diamond cut are beneficially resolved by considering the complex combination of physical factors that influence the appearance of a faceted diamond (e.g., the interaction of light with diamond as a material, the shape of a given polished diamond, the quality of its surface polish, the type of light source, and the illumination and viewing conditions), and incorporating these into an analysis of that appearance.

Diamond faceting began in about the 1400s and progressed in stages toward the round brilliant we know today (see Tillander, 1966, 1995). In his early mathematical model of the behavior of light in fashioned diamonds, Tolkowsky (1919) used principles from geometric optics to explore how light rays behave in a prism that has a high refractive index. He then applied these results to a two-dimensional model of a round brilliant with a knife-edge girdle, using a single refractive index (that is, only one color of light), and plotted the paths of some illustrative light rays.

Tolkowsky assumed that a light ray is either totally internally reflected or totally refracted out of the diamond, and he calculated the pavilion angle needed to internally reflect a ray of light entering the stone vertically through the table. He followed that ray to the other side of the pavilion and found that a shallower angle is needed there to achieve a second internal reflection. Since it is impossible to create substantially different angles on either side of the pavilion in a symmetrical round brilliant diamond, he next considered a ray that entered the table at a shallow angle. Ultimately, he chose a pavilion angle that permitted this ray to exit through a bezel facet at a high angle, claiming that such an exit direction would allow the dispersion of that ray to be seen clearly. Tolkowsky also used this limiting case of the ray that enters the table at a low angle and exits through the bezel to choose a table size that he claimed would allow the most fire. He concluded by proposing angles and proportions for a round brilliant that he believed best balanced the brilliance and fire of a polished diamond, and then he compared them to some cutting proportions that were typical at that time. However, since Tolkowsky only considered one refractive index, he could not verify the extent to which any of his rays would be dispersed. Nor did he calculate the light loss through the pavilion for rays that enter the diamond at high angles.

Over the next 80 years, other researchers familiar with this work produced their own analyses, with varying results. It is interesting (and somewhat surprising) to realize that despite the numerous possible combinations of proportions for a standard round brilliant, in many cases each researcher arrived at a single set of proportions that he concluded produced an appearance that was superior to all others. Currently, many gem grading laboratories and trade organizations that issue cut grades use narrow ranges of proportions to classify cuts, including what they consider to be best.

Several cut researchers, but not Tolkowsky, used "Ideal" to describe their sets of proportions. Today, in addition to systems that incorporate "Ideal" in their names, many people use this term to refer to measurements similar to Tolkowsky's proportions, but with a somewhat larger table (which, at the same crown angle, yields a smaller crown height percentage). This is what we mean when we use "Ideal" herein.

Numerous standard light modeling programs have also been long available for modeling light refractive objects.

E.g., Dadoun, et al., The Geometry of Beam Tracing, ACM Symposium on Computational Geometry, 1985, p. 55–61; Oliver Devillers, Tools to Study the Efficiency of Space Subdivision for Ray Tracing; Proceedings of PixIm '89 Conference; Pub. Gagalowicz, Paris; Heckbert, Beam Tracing Polygonal Objects, Ed. Computer Graphics, SIGGRAPH '84 Proceedings, Vol. 18, No. 3, p. 119–127; Shinya et al., Principles and Applications of Pencil Tracing, SIGGRAPH '87 Proceedings, Vol. 21, No. 4, p. 45–54; Analysis of Algorithm for Fast Ray Tracing Using Uniform Space Subdivision, Journal of Visual Computer, Vol. 4, No. 1, p. 65–83. However, regardless of what standard light modeling technique is used, the diamond modeling programs to date have failed to define effective metrics for diamond cut evaluation. See e.g., (Tognoni, 1990) (Astric et al., 192) (Lawrence, 1998) (Shor 1998). Consequently, there is a need for a computer modeling program that enables a user to make a cut grade using a meaningful diamond analysis metric. Previously, Dodson (1979) used a three-dimensional model of a fully faceted round brilliant diamond to devise metrics for brilliance, fire, and "sparkliness" (scintillation). His mathematical model employed a full sphere of approximately diffuse illumination centered on the diamond's table. His results were presented as graphs of brilliance, fire, and sparkliness for 120 proportion combinations. They show the complex interdependence of all three appearance aspects on pavilion angle, crown height, and table size. However, Dodson simplified his model calculations by tracing rays from few directions and of few colors. He reduced the model output to one-dimensional data by using the reflection-spot technique of Rosch (S. Rosch, 1927, Zeitschrift Kristallographie, Vol. 65, pp. 46–48.), and then spinning that computed pattern and evaluating various aspects of the concentric circles that result. Spinning the data in this way greatly reduces the richness of information, adversely affecting the aptness of the metrics based on it. Thus, there is a need for diamond evaluation that comprises fire and scintillation analysis.

SUMMARY OF THE INVENTION

According to one embodiment described herein, a system models interaction of light with a faceted diamond and analyzes the effect of cut on appearance. To this end, computer graphics simulation techniques were used to develop the model presented here, in conjunction with several years of research on how to express mathematically the interaction of light with diamond and also the various appearance concepts (i.e., brilliance, fire, and scintillation). The model serves as an exemplary framework for examining cut issues; it includes mathematical representations of both the shape of a faceted diamond and the physical properties governing the movement of light within the diamond.

One mathematical model described herein uses computer graphics to examine the interaction of light with a standard (58 facet) round-brilliant-cut diamond with a fully faceted girdle. For any chosen set of proportions, the model can produce images and numerical results for an appearance concept (by way of a mathematical expression). To compare the appearance concepts of brilliance, fire, and scintillation in round brilliants of different proportions, we prefer a quantity to measure and a relative scale for each concept. A specific mathematical expression (with its built-in assumptions and qualifications) that aids the measurement and comparison of a concept such as fire is known as a metric. In one embodiment, the metric for fire considers the total number of colored pixels, color distribution of the pixels, length distribution of colored segments (as a function of angular position), density distribution of colored segments, angular distribution of colored segments, the distribution of colors over both azimuthal and longitudinal angle, and/or the vector nature (directionality) of colored segments. A more preferred embodiment uses the following metric to evaluate fire: sum (over wavelength) of the sum (over the number of ray traces) of the differential area of each ray trace that exceeds a power density threshold cutoff, multiplied by the exit-angle weighting factor. This may be calculated as follows:

$$DCLR = \Sigma_{wavelengths} \Sigma_{rays} (dArea * \sigma * Weighting\ Factor).$$

In this preferred embodiment, if the power density of a trace is greater than the threshold cutoff, $\sigma=1$; otherwise $\sigma=0$ and the ray (or other incident light element) is not summed. In a most preferred embodiment, comprising a point light source, the metric considers the total number of colored pixels (sum of rays), the length distribution of colored segments (because with a point source, length approximates differential area), angular distribution of colored segments (the weighting factor) and a threshold cutoff ($\sigma=0$ or 1) for ray (or other incident light element) power density. Although other factors (e.g., bodycolor or inclusions) may also influence how much fire a particular diamond provides, dispersed-color light return (DCLR) is an important component of a diamond fire metric.

The systems and methods described herein may further be used to specifically evaluate how fire and scintillation are affected by cut proportions, including symmetry, lighting conditions, and other factors. In addition to the cut proportions expressly including in the tables, other proportions, such as crown height and pavilion depth may be derived from the tables, and used as the basis for optical evaluation and cut grade using the methods and systems disclosed herein. Other embodiments and applications include an apparatus and system to grade a faceted diamonds, new methods of providing target proportions for cutting diamonds, new types of diamonds cuts and new methods for cutting diamonds.

Within the mathematical model, all of the factors considered important to diamond appearance—the diamond itself, its proportions and facet arrangement, and the lighting and observation conditions—can be carefully controlled, and fixed for a given set of analyses. However, such control is nearly impossible to achieve with actual diamonds. The preferred model described herein also enables a user to examine thousands of sets of diamond proportions that would not be economically feasible to create from diamond rough. Thus, use of the model allows the user to determine how cut proportions affect diamond appearance in a more comprehensive way than would be possible through observation of actual diamonds. In one preferred embodiment, the system, method and computer programs use to model the optical response of a gemstone use Hammersley numbers to choose the direction and color for each element of light refracted into a model gemstone (which defines the gemstone facets) to be eventually reflected by the model gemstone's virtual facets, and eventually exited from the model gemstone to be measured by a model light detector. The gemstone is then ultimately graded for its optical properties based on the measurement of said exited light elements from the gemstone model.

In another preferred embodiment, the system determines the grade of a cut using certain assumptions—best brilliance, best fire, best balance of the two, best scintillation, best weight retention, best combination—that can be achieved from a particular piece of rough. In addition, an instrument may also measure optical performance in real diamonds based on the models described. The models of light diamond interaction disclosed herein can also be used to compare and contrast different metrics and different lighting and observation conditions, as well as evaluate the dependence of those metrics on proportions, symmetry, or any other property of diamond included in the model.

BRIEF DESCRIPTION OF THE DRAWINGS

FIG. 1 is a drawing and table that outlines the assumptions on which a preferred model is based. Diamond model reference proportions in this patent application, unless otherwise specified, are table 56%, crown angle 34°, pavilion angle 40.5°, girdle facet 64, girdle thickness 3.0%, star facet length 50%, lower girdle length 75%, culet size 0.5%.

FIGS. 2A to 2C are a plot of DCLR versus crown angle over three thresholds for a modeled round brilliant diamond along with the table of corresponding data.

FIGS. 3A to 3C are a plot of DCLR versus pavilion angle over three thresholds for a modeled round brilliant diamond along with the table of corresponding data.

FIGS. 4A to 4C are a plot and table of DCLR with reference to crown angle and table size for a low power density threshold cutoff modeling system.

FIGS. 5A to 5C are a plot and table of DCLR with reference to crown angle and table size for a medium power density threshold cutoff modeling system.

FIGS. 6A to 6C are a plot and table of DCLR with reference to crown angle and table size for a high power density threshold cutoff modeling system.

FIGS. 7A and 7b are a table of DCLR rating for various diamond proportions, varying by star facet length, for 3 values of crown angle.

FIG. 8 is a table of DCLR ratings for various diamond proportions, varying by star facet length, for a medium power density threshold cutoff modeling system.

FIG. 9 is a table of DCLR ratings for various diamond proportions, varying by star facet length, for a low power density threshold cutoff modeling system.

FIGS. 10A to 10F are a table of DCLR ratings for various diamond proportions, varied by pavilion angle and table size, for a high power density threshold cutoff modeling system.

FIGS. 11A to 11F are a table of DCLR ratings for various diamond proportions, varied by pavilion angle and table size, for a medium power density threshold cutoff modeling system.

FIGS. 12A to 12F are a table of DCLR ratings for various diamond proportions, varied by pavilion angle and table size, for a low power density threshold cutoff modeling system.

FIG. 23 is a table of DCLR rating for certain diamond proportions, varying by table size.

FIG. 24 is a table of DCLR rating for certain diamond proportions, varying by lower girdle size.

FIGS. 26A and 26B are a table of DCLR rating for certain diamond proportions, varying by culet size.

DESCRIPTION OF THE INVENTION

Figure 2A:
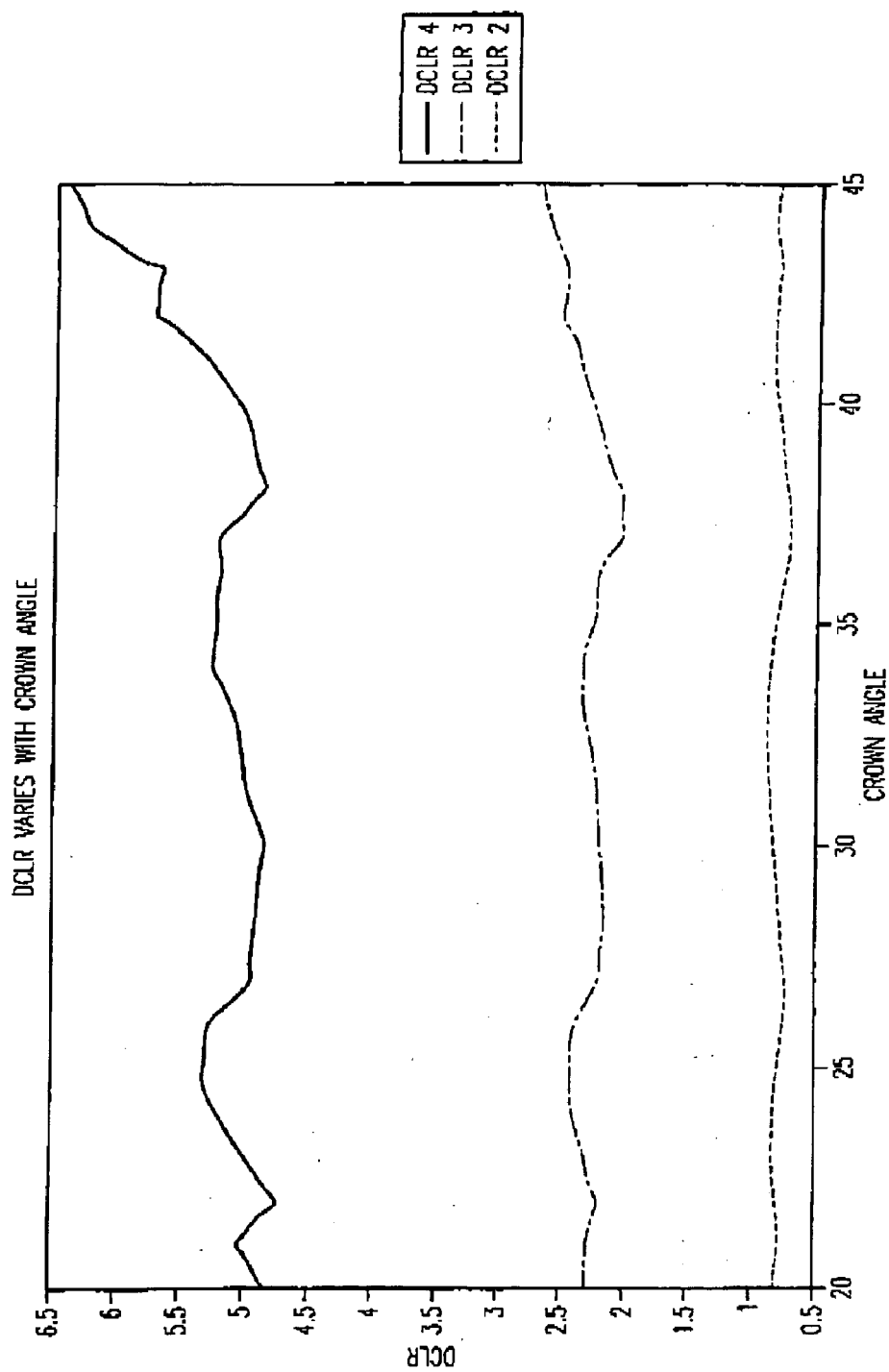

Assumptions and Methods. The mathematical model presented here creates a fresh structure for examining nearly all aspects of the influence that cut has on a diamond's appearance. FIG. 1 provides the assumptions on which a preferred model may be based: a detailed list of the physical properties included in the model, a mathematical description of the proportions of the round brilliant, and a description of the lighting condition used in this study. The details of the lighting conditions affect the specific numerical values we present here. The model traces light from the modeled light source through a mathematical representation of a round brilliant of any chosen proportions (referred to hereafter as the "virtual" diamond) to produce two kinds of results: (1) digital images of the virtual diamond, and (2) a numerical evaluation of an appearance concept (in this case, fire).

The metrics disclosed herein may be run on any computer, such as a Pentium-based PC using standard light refraction modeling techniques and light elements, including those used in CAD Programs, as are known in the art.

The preferred metric for fire, Dispersed Colored Light Return (DCLR), is an original product the development of which required considerable creative thought. DCLR describes the maximum extent to which a given set of proportions can disperse light toward an observer; the value is defined using a point light source at infinite distance and a hemispherical observer also located at infinity. (In general, observed dispersion depends strongly on the light source and observation geometry: as the distance between the observer and diamond increases, the observer sees less white light and more dispersed colors).

Another metric, describing scintillation, may consider both the static view (amount and degree of contrast) and the dynamic view (how the contrast pattern changes with movement), and may factor in parts of brilliance (how the spatial resolution of the contrast interacts with human vision to affect how "bright" an object looks, and the effects of glare), and describe what most diamond cutters call "life," and Dodson (1979) calls "sparkliness." The relevant scintillation factors for the static view include the number of edges seen across the face of the round brilliant, the distribution of distances between those edges, the shapes made by them, the contrast in output power across those edges (e.g. black against white or medium gray against pale gray), and the visual impact of colored rays on the appearance of the black and white pattern. All these aspects are present in the "view-from infinity" (VFI) diagrams of the model output; See FIGS. 13–22, however, they are also discernable in a head-on photo or direct observation of a diamond. The relationship between the positions of exit rays at infinity and the shapes they form on an image plane above the stone (parallel to the table) at some distance, enables a user of the model to calculate a scintillation metric from the raw data at any chosen distance. The factors listed above change in numerical value with differences in vertical distance. Thus, the metric may be based on a vertical distance or distances suitable to approximate the experience of a standard observer.

The metrics for fire and scintillation may also incorporate dynamic aspects. Dynamic aspects into the preferred fire metric, DCLR, are obtained by placing the observer at infinity and weighting the contributions of rays by their exit angle with a cosine-squared function. Another way to explore dynamic shifts is to move the light source—such that the incoming rays are perpendicular to a bezel or star facet rather than the table, and compare the output (both the diagram and DCLR value) to that obtained with the light source directly over the table. The dynamic aspects of scintillation likewise involve changes in the black-and-white pattern with motion of the stone, light source, or observer.

The details of human vision may also be incorporated in each of these metrics. Thus, DCLR preferably incorporates a threshold for the amplitude range of human vision with "ordinary" background illumination. (Humans see considerably more than the 256 levels of gray used by a computer monitor). The scintillation metric incorporates human vision aspects related to contrast intensity and spatial resolution of contrasting light levels and colors and considers how colored rays look against different patterns. These aspects of human vision also come into play in the design of a human observation exercise, wherein a number of people will observe a fixed set of diamonds under one or more fixed viewing conditions, and compare their brilliance, brightness, fire, and scintillation, as a check on the predictions from modeling.

Although the human visual system can detect as few as 7 photons when Lit is fully adapted to the dark, far more light is required to stimulate a response in an ordinarily bright room. The specific range of the human visual system in ordinary light has; not been definitively measured, but professional estimates suggest detection of up to 10,000 gray levels. (A computer monitor uses 256 levels, and high-quality photographic film has just under 1000). Thus it is uncertain how much of fire to take into consideration to match the capacity of human vision: Accordingly, one embodiment of the metric comprises a threshold power density cutoff to approximate human vision. Furthermore, the power density threshold may be weighted to account for differentiation in human eye sensitivity to different parts of visual spectrum (e.g., use a higher threshold cutoff for green light because humans have lower sensitivity for green as compared This to blue light). This principle also applies with force to the scintillation metric. As disclosed herein, DCLR values may be calculated using ranges of 2, 3, and 4 orders of magnitude (i.e. including rays down to 100 (fire 2), 1000 (fire 3), and 10,000 (fire 4) times weaker than the brightest ones). In the preferred embodiment, DCLR is a directly computed value, and traces all light from the source so there is no convergence and no error. The results are shown as DCLR values graphed against various proportion parameters. See FIGS. 2A to 2C through 6A to 6C. Fire 2 means that a threshold eliminates refracted light elements at less than 1% of the brightest light elements. Fire 3 uses a cut off of 0.1% off and Fire 4 uses a 0.01% cut off. The obvious result from this initial data is that DCLR (and thus fire) does not have a monotonic dependence on only the clown proportions, as Tolkowaky's 1919 work claimed, but shows a multi-valued dependence on several proportions, including the pavilion angle. In other words, DCLR like WLR, can be maximized in a number of ways.

Different lighting geometries emphasize different aspects of a diamond's appearance. Thus, although the lighting and observing conditions must be specified for a given metric, these conditions can be varied and used in calculation of similar metrics.

Likewise, in a preferred embodiment, the model assumes a fully faceted girdle, perfect symmetry, perfect polish, no color, no fluorescence, no inclusions, and no strain. Actual diamonds may have bruted girdles, asymmetries (e.g. culet off center, or table not parallel to girdle), scratches and polishing lines, color, blue or yellow fluorescence of varying strengths, a variety of inclusions, and a strain in a variety of distributions. Each of these properties affects the movement of light and the actual expression of the appearance aspects. Many of these aspects may be incorporated into the model. In another embodiment, the invention contemplates the use of a device (or devices, one for each metric) that measures the various appearance metrics for actual diamonds, including each one's particular oddities.

Although the DCLR may be calculated for the idealized set of average proportions, they may also be calculated for that of a particular stone. Thus, in another embodiment a low end grade may be used for the diamond industry and jewelers; the metrics disclosed herein readily identify sets of proportions with poor optical performance. See FIGS. 2A to 2C through 6A to 6C.

Defining Metrics: FIRE.

One advantage of using a computer model is the capability it gives us to examine thousands of proportion variations. To make sense of so much data, however, we needed to define a metric for fire, and use it to compare the performance of the different proportion combinations. A variety of mathematical expressions can be created to describe such light. Each expression requires explicit or implicit assumptions about what constitutes fire and about light sources, viewing geometry, response of the human eye, and response of the human brain. The mathematical definition of fire may represent one viewing geometry—that is, a "snapshot"—or, more preferably, represent an average over many viewing situations.

Dispersed-Colored Light Return. A preferred metric described herein is called Dispersed Colored Light Return (DCLR); it is specific to each set of modeled diamond proportions with the chosen illumination. After examining a variety of possible metrics for fire, DCLR represents the best way to evaluate fire using a viewing model that looks at the stone from an infinite distance to achieve maximum dispersion.

According to this preferred embodiment, the metric for fire, DCLR, uses an approach that is completely different than the approach Dodson (1979) used. Starting with a point light source at infinity and a hemispherical observer, also at infinity, the preferred metric takes into account the size, brightness, exit angle, number and color of all incident light elements that exit the crown using the following equation:

$$DCLR = \Sigma_{wavelengths} \Sigma_{light\ elements} (dArea * Weighting\ Factor).$$

In a more preferred embodiment, the method uses the same weighting factor, the square of the cosine of the exit angle, as in the Weighted Light Return Model discussed in Gems and Gemology Vol. 34, No. 3. pp. 158–183, Fall 1998 (e.g. rays that exit the modeled diamond vertically (90%) have a weighting factor of 1, and rays that exit at 65° have a weighting factor of 0.82). This weighting numerically mimics the common industry practice of rocking a stone back and forth and from side to side while observing it, through an angular sweep of about 35–40% from the vertical. The light elements may be pencils, bundles, rays or any other light unit element known in the light modeling art.

The light elements to be included in DCLR may be also required to meet a power density threshold cutoff. Thus, in a most preferred embodiment, the DCLR is a sum (over wavelength) of the sum (over the number of light element traces) of the differential area of each light element trace that surpasses a threshold power density cutoff (most preferably 1% of the brightest element) times an exit-angle weighting factor.

The most preferred embodiment may beneficially trace pencils of light forward through the gemstone model and then trace rays backwards through the model to measure the optical properties of a gemstone. Each of the gemstone illumination models used herein may also include the use of Hammersley numbers to determine the direction and color for each light element directed at the gemstone model.

Dodson (1979) evaluated his metrics for 3 crown heights (10, 15, and 20%), 4 table sizes (40, 50, 60, 70%), and 10 pavilion angles between 38 and 55%, a total of 120 proportion combinations, and showed that his three metrics yielded wide variations across these proportions. In contrast, the present description includes a calculated DCLR for 2148 combinations of 6 proportions: crown angle, pavilion angle, table size, star facet length, lower girdle length, and culet size (This range includes both common commercial proportions and values of crown angles and star facet lengths that are very rarely cut). See FIGS. 7A and 7B through 12A to 12F. These metrics are computed functions of the 8 independent shape variables, and each data set forms a surface over the 6 shape variables we have varied to date. We have explored the topography of the DCLR surface with standard graphical and numerical techniques, to find all those combinations that yield high DCLR, and to reveal relationships between proportions and brightness.

Moreover, using previously published WLR data, a user can also compare the DCLR data set with the previously described Weighted Light Return set (see Gem & Gemology Vol. 34, No. 3, pp. 158–183) or other brilliance data to find proportions that yield an attractive balance of brilliance and fire.

Results

In the preferred model, a point light source at infinite distance shines on the table of a virtual diamond of chosen proportions; because the light source is so far away all the entering rays are parallel. These rays refract and reflect, and all those that refract out of the crown fall on the observer, a hemisphere at infinite distance. Because the observer is so far away, all the light that falls on it is fully dispersed; thus, there is no "white" output. DCLR results are shown in FIGS. 2–12. The VFI diagrams are direct output resulting from the model, with the background color reversed from black to white for greater ease in viewing and printing. See FIGS. 13–22. A VFI diagram is one fourth of the observer hemisphere, unrolled onto the page or screen; the point is the overhead center of the hemisphere (light exiting perpendicular to the table, and the rounded border is the edge of the hemisphere (light exiting parallel to the girdle).

All static aspects of fire and scintillation are contained within this output. However, of the qualities we considered relevant to fire; only 3 of those 7 ended up in the most preferred metric (total number, length distribution [changed to differential area], and angular distribution) and we added a new concept, that of the threshold for power density. That concept comes from making the VFI diagrams because the number of colored segments changed so noticeably as a function of power density.

Images and DCLR. The calculations made with our model also may be used to produce realistic digital images of virtual diamonds. Thus, computer-generated images can reproduce the patterns of light and dark seen in actual round brilliant diamonds under lighting conditions similar to those used with the model. The model can generate a variety of digital images, from different perspectives and with different lighting conditions. However, the details of how fire changes with proportions can be better studied by comparing a metric, such as DCLR values, than by visually examining thousands of images, whether VFI diagrams or virtual diamonds themselves.

Results for Key Individual Parameters. Our Investigation of the dependence of DCLR on crown angle, pavilion angle, star facet length, and table size, began with an examination of how DCLR varies with each of these three parameters while the remaining seven parameters are held constant. Except where otherwise noted, we fixed these parameters at the reference proportions (see FIG. 1). See FIGS. 7A and 7B through 12A to 12F.

Figure 2B:
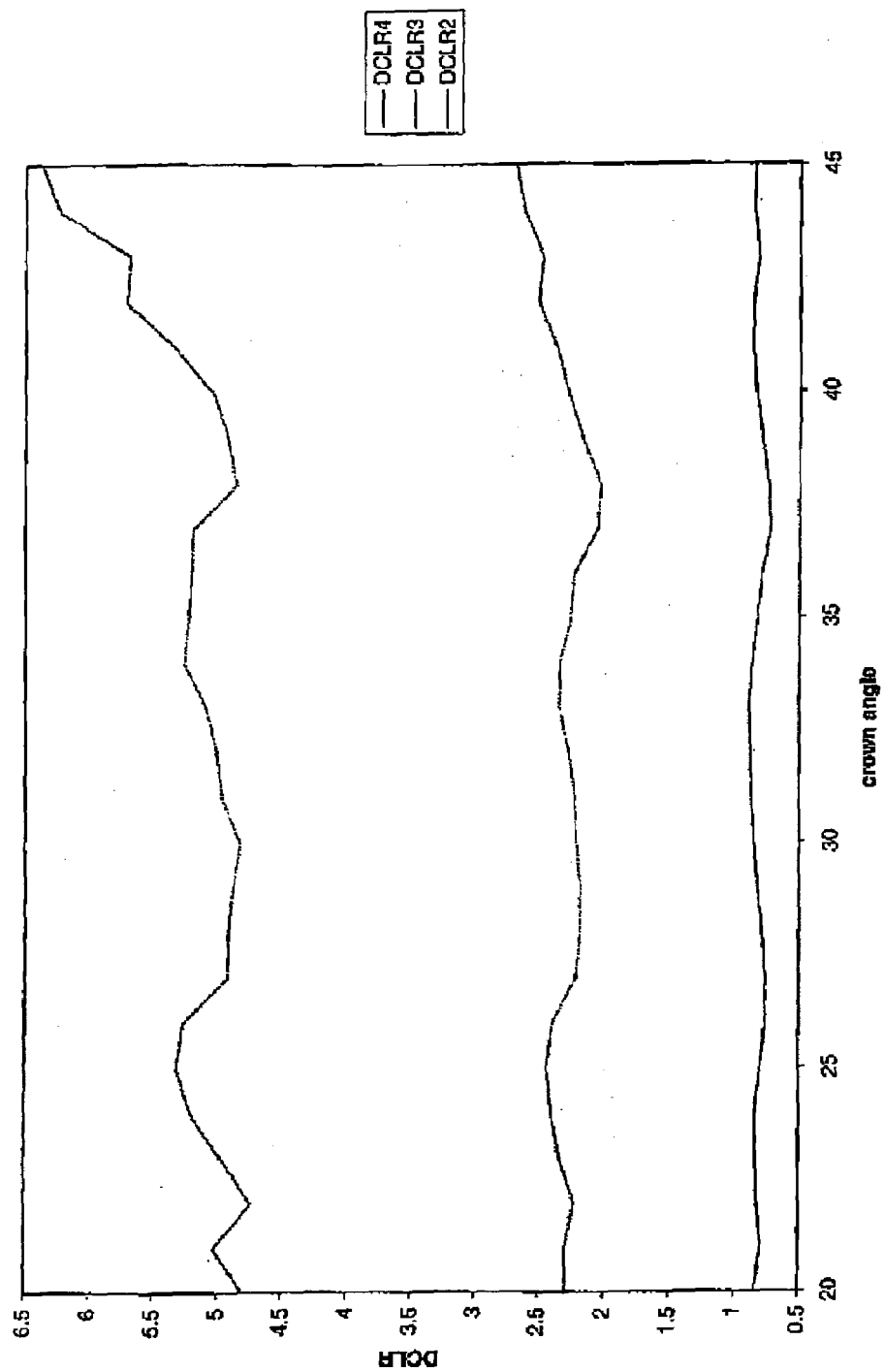

Crown Anale. In general, DCLR increases as crown angle increases; but, as FIGS. 2A to 2C show, there are two local maxima in DCLR across the range of angles, at about 25° and 34–35°, and a rise in values at crown angles greater than 41°. However, moderately high crown angles of 36–40° yield a lower DCLR value than either of the local maxima. The same topography is seen at each of the three thresholds, although the numerical range of each data set (the difference between the maximum and minimum values) decreases as the threshold is raised.

Figure 3B:
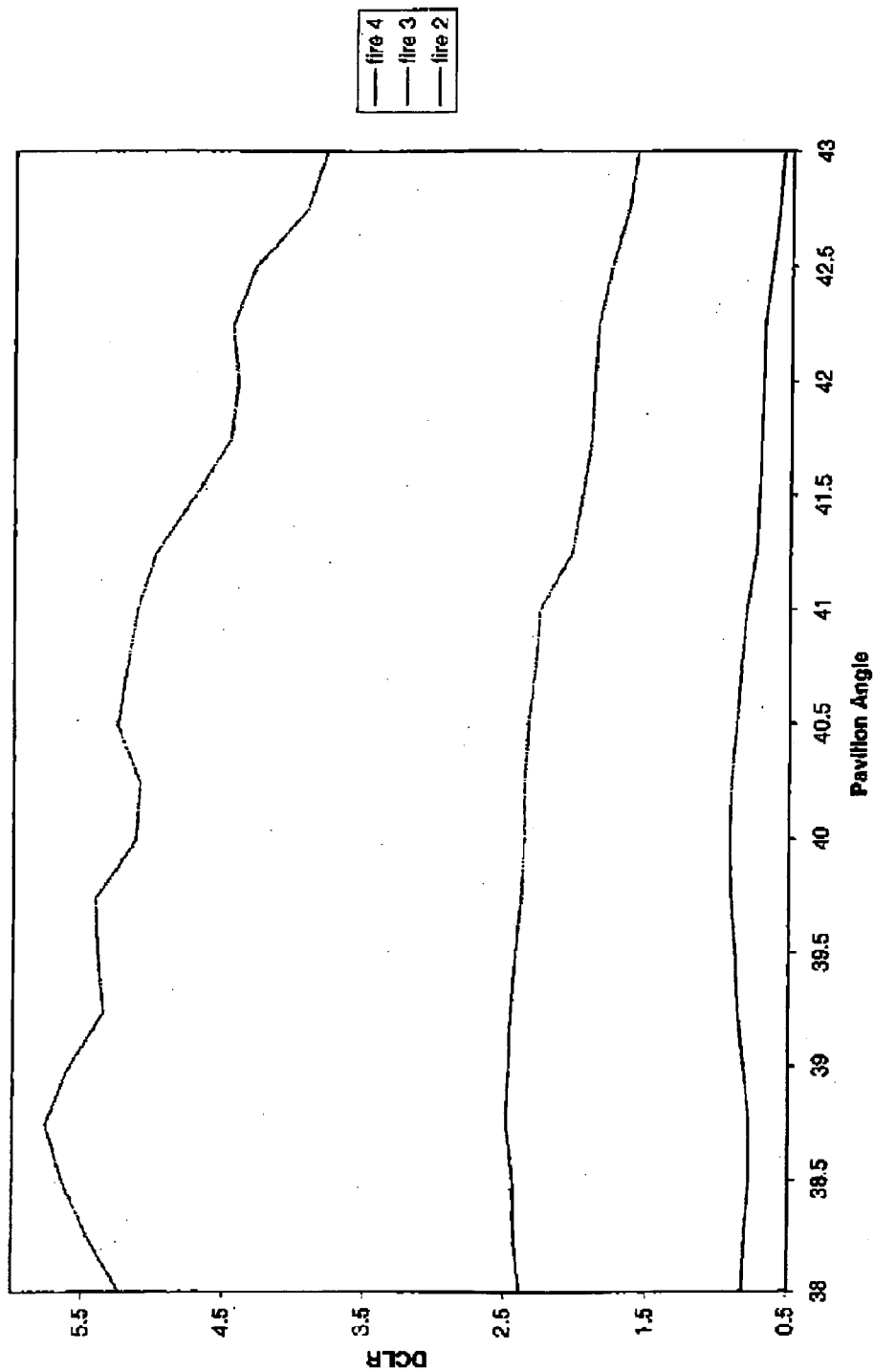

Pavilion Angle. This is often cited by diamond manufacturers as the parameter that matters most in terms of brilliance (e.g., G. Kaplan, pers. comm., 1998), but we surprisingly found the greatest variation in DCLR for changes in pavilion angle. FIGS. 3A to 3C show an overall decrease in DCLR (calculated with the lowest threshold) with increasing pavilion angle, with a true maximum at 38.75°, and local maxima at 40–41° and 42.25°. Unlike crown angle, pavilion angles are typically manufactured in a fairly narrow range; the peak from 40–41° covers a broad range for this parameter. Similar topography is seen for the intermediate threshold, but the peak at low pavilion angle is absent from DCLR calculated at the highest threshold.

Star Facet Length. We calculated the variation of DCLR (with the lowest threshold) with changes in the length of the star facet for three values of the crown angle: 34°, 36°, and 25°. The range in DCLR values is relatively small, but as seen in FIGS. 7A and 7B, 8, and 9 there is a primary maximum in each array. At the reference crown angle of 34°, a star facet length of 0.56 yields the highest DCLR. This maximum shifts to about 0.58 for a crown angle of 36°, and increases substantially to a star facet length of 0.65–0.65 for a crown angle of 25°. Longer star facet length means that the star facet is inclined at a steeper angle relative to the table (and girdle, in a symmetrical round brilliant), and thus these results imply that the star facets act similarly to the bezel facets with regard to the production of fire. Also, as with crown angle, similar topography is seen in the arrays calculated with higher thresholds but with significantly reduced range of DCLR values.

Two of the high-threshold arrays (34° and 36° crown angle) and the medium-threshold data show secondary maxima at star facet lengths of 0.3, 0.32 and 0.36 respectively. Neither such short stars, nor the longer stars indicated by the primary maxima, are commonly used in the production of round brilliant diamonds.

Table Size. DCLR shows a bi-modal response to variations in table size, as shown in FIGS. 10A to 10F, 11A to 11F, and 12A to 12F. For the low and medium thresholds, DCLR is approximately constant for tables less than 0.55, rapidly decreases for tables of 0.56 and 0.57, and then remains approximately constant for tables of; 0.58 and greater. For the highest threshold, DCLR is approximately constant across the entire range of table sizes. See, e.g., FIG. 23.

Lower Girdle. The variation of DCLR with lower girdle facet length is moderate, similar in magnitude to the variation found with crown angle. For all three thresholds, longer lower girdle facets are favored, with broad maxima at 0.80–0.85. Lower girdle facets form an angle with the girdle plane that is less than the pavilion angle; the longer these facets are the closer their angle becomes to the pavilion angle. See FIG. 24.

Figure 25:
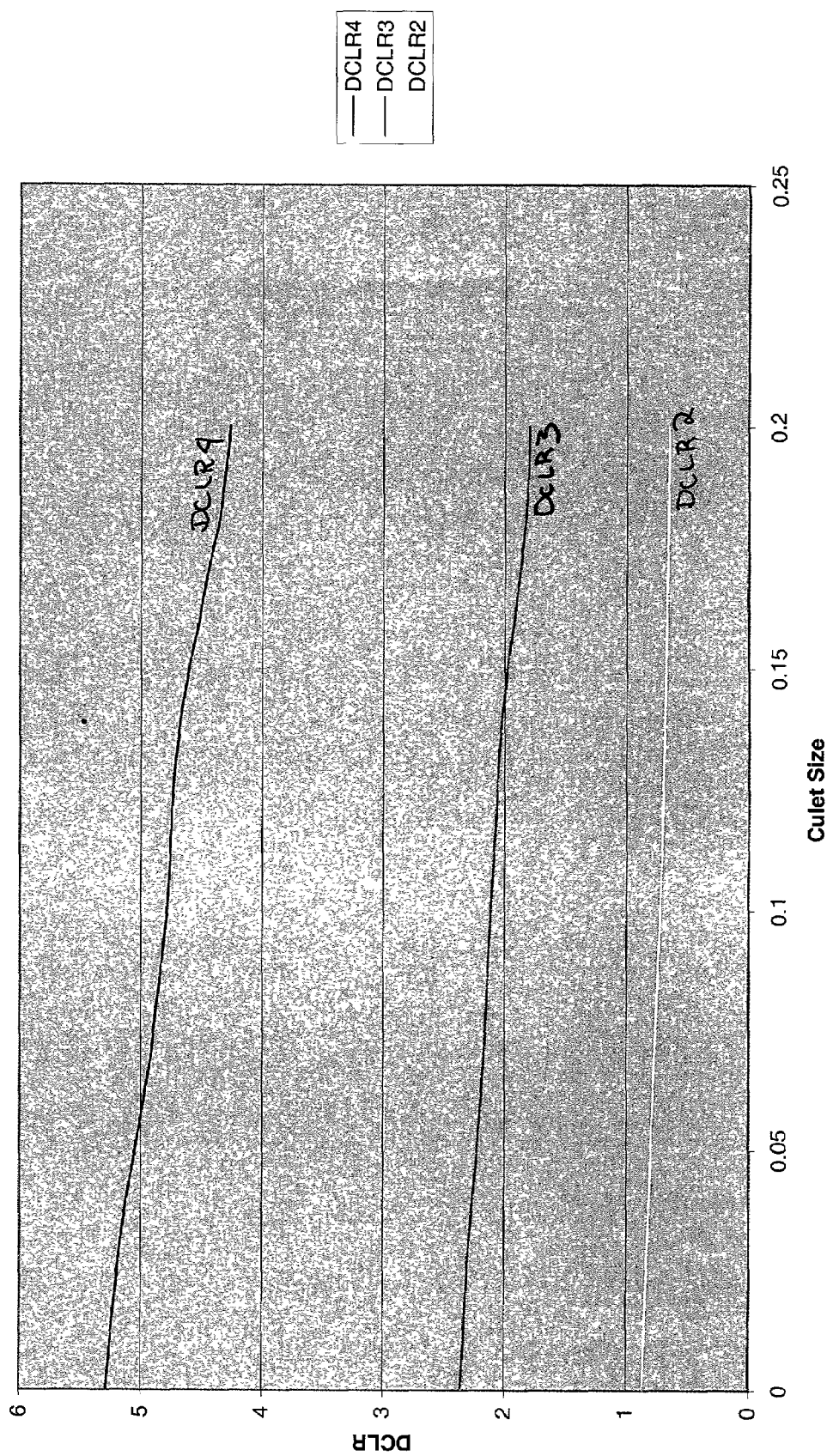
FIG. 25 is a plot of DCLR versus culet size corresponding to FIGS. 26A and 26B.

Culet Size. Unlike WLR, which showed little dependence on culet size, DCLR decreases significantly with increasing culet size. This decrease is smooth and monotonic, and for the lowest threshold the DCLR value decreases by 25%. See FIGS. 25, 26A and 26B.

Thus, as shown in the tables and figures disclosed herein, a cut grade that considers fire can be made by reference to enter star facet length, lower girdle length, and culet size. For example, as shown in FIGS. 2–6, the cut grade may be based on a fire peak within 40–41° pavilion angle, but also recognize fire peaks substantially at 38.75° and 42.5°.

Combined Effects. Some of the interactions between crown angle, pavilion angle, and table size—and their combined effects on DCLR values—can be seen when these proportion parameters are examined two at a time. One way to visualize these effects is to draw them to look like a topographic map (which shows the differences in elevation of an area of land). We can draw subsets of the data as cross-sections (slices) through the data set with one parameter held constant, and the WLR values can then be expressed as contours. These cross-sections can be read in the same manner as topographic maps; but instead of mountains, these "peaks" show proportion combinations that produce the highest calculated DCLR values.

Figure 4A:
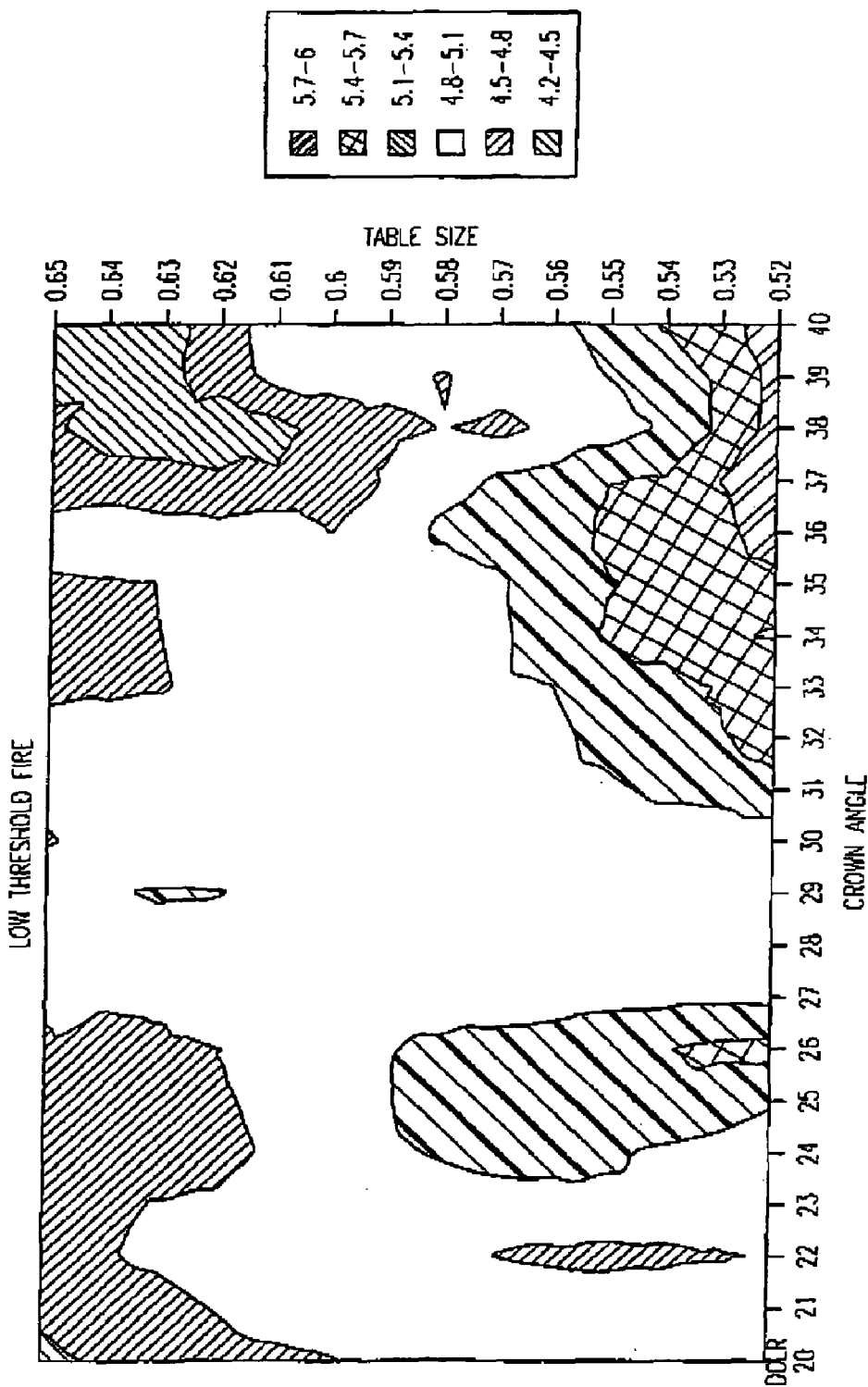
Figure 4B:
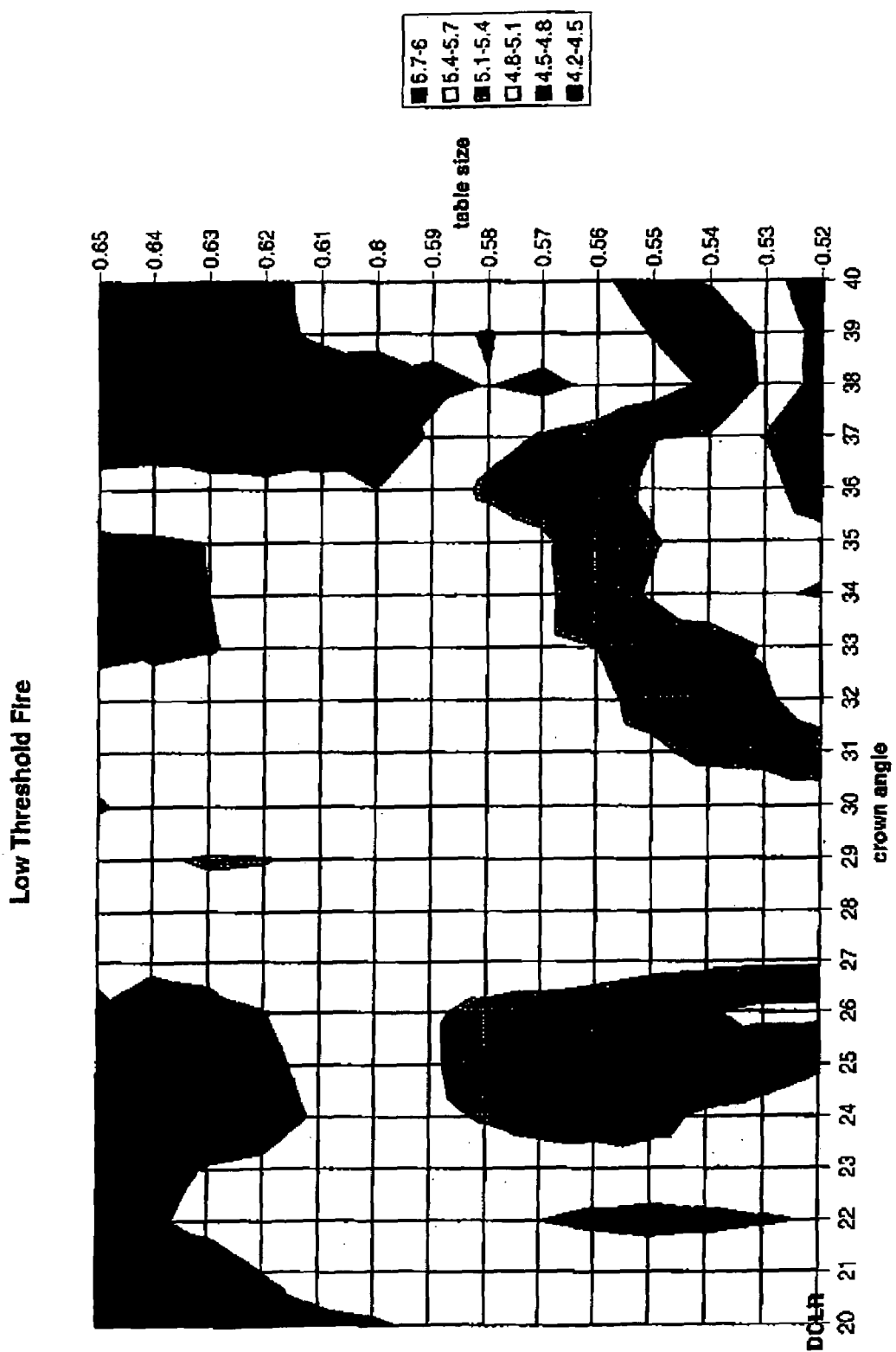

FIGS. 4A to 4C shows such a contour map for DCLR (calculated with the lowest threshold) with variation in both crown angle and table size. Two "ridges" of rapidly varying DCLR values are evident at crown angles of 25–26° and crown angles greater than or equal to 34°. This latter ridge is broad and shows convoluted topography. These ridges become gullies with decreasing table size; that is, at these crown angles, table sizes of 0.58 and less yield high DCLR values, but larger table sizes yield lower DCLR values than are found at other crown angles. In particular, there is a local maximum in DCLR for tables of 0.65–0.63 and a crown angle of 29°.

Figure 5A:
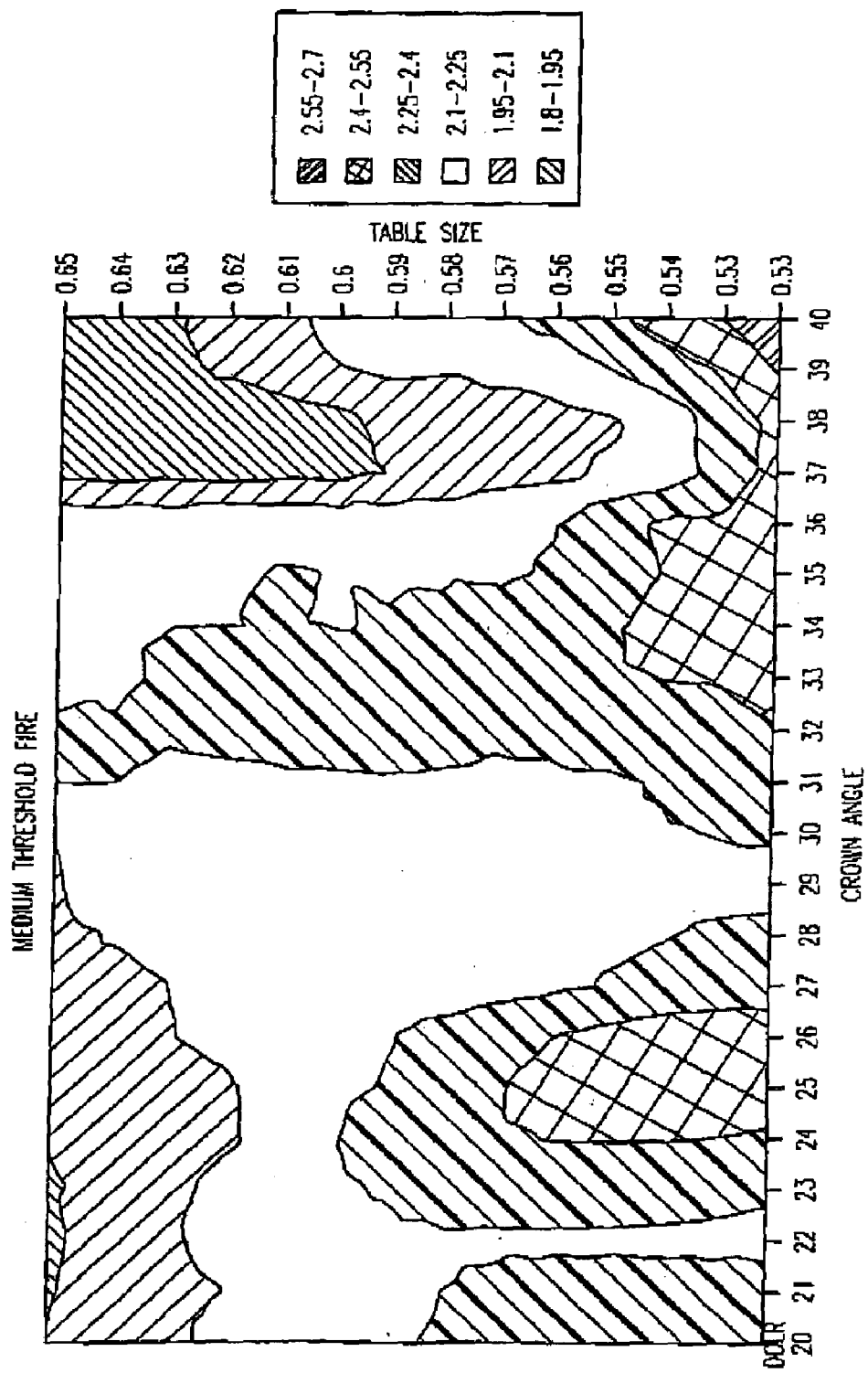
Figure 5B:
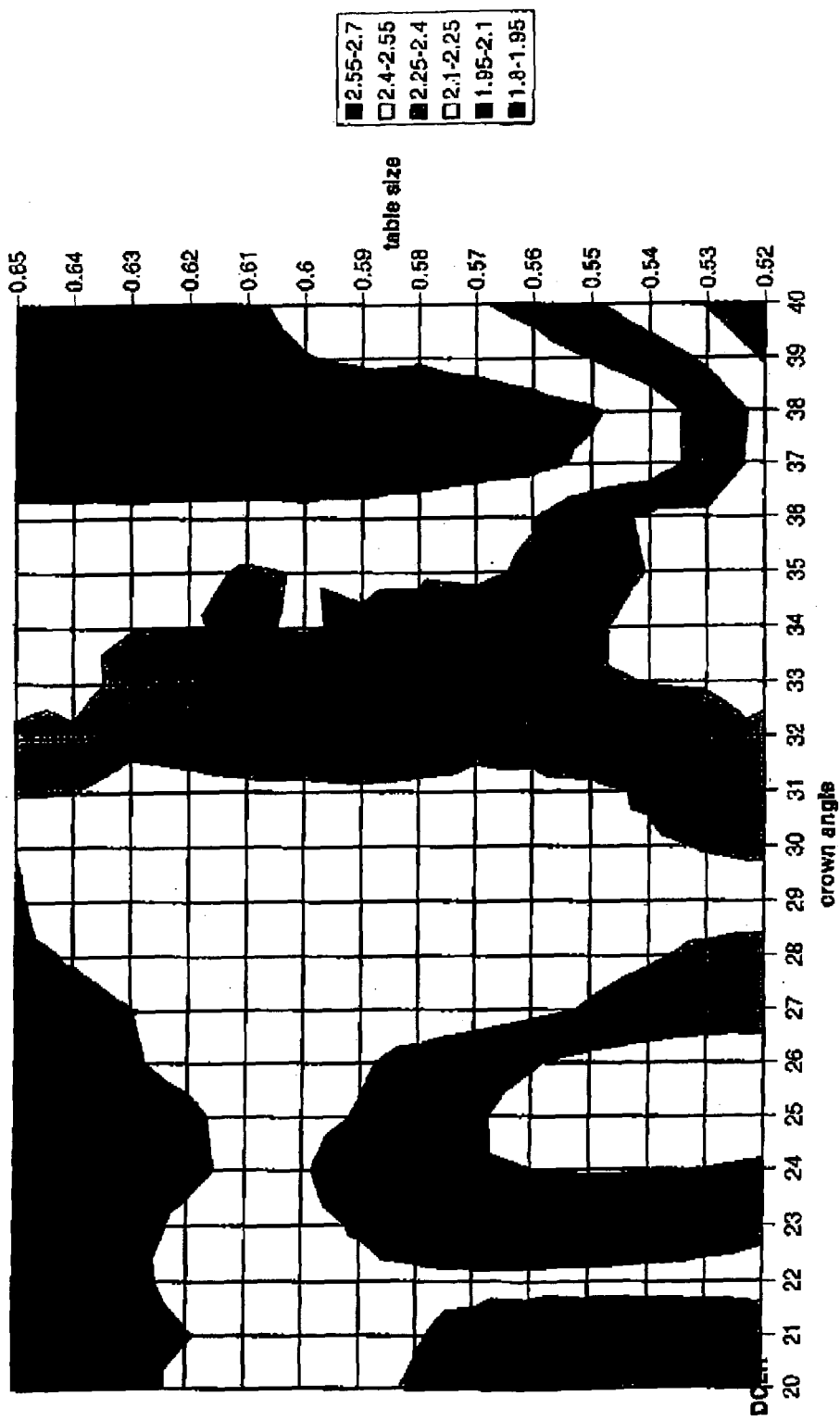
Figure 6A:
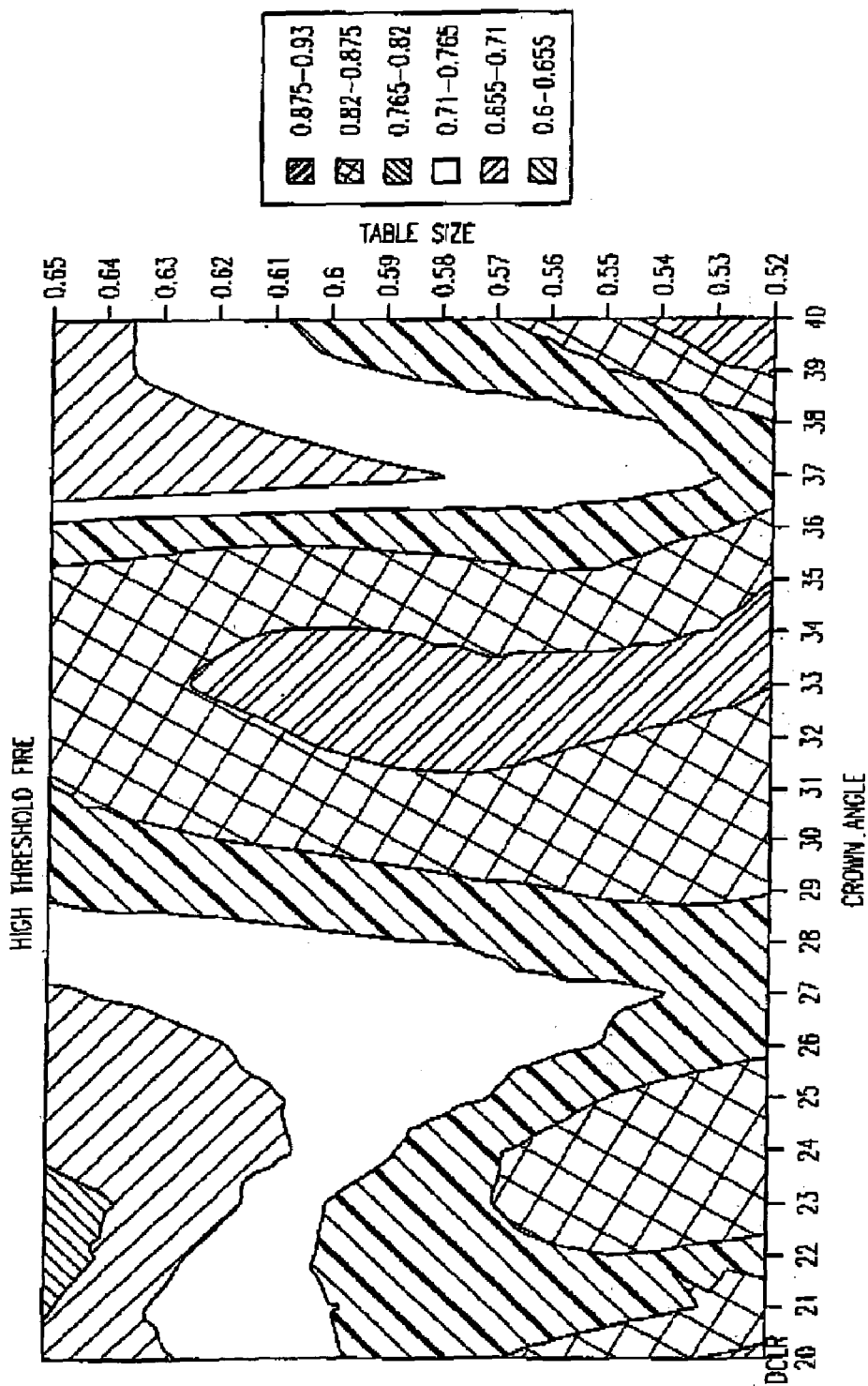
Figure 6B:
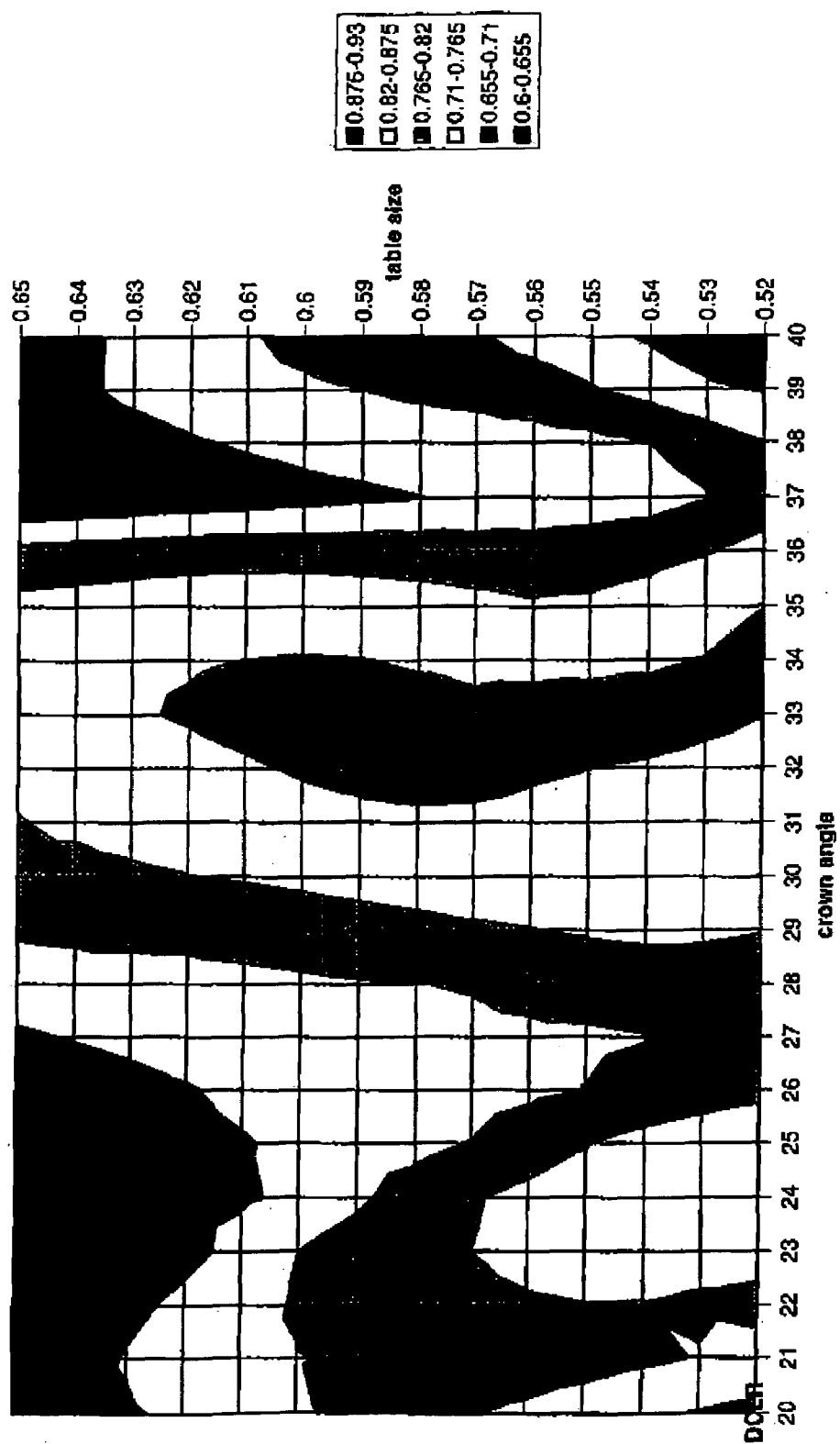
Figure 13:
FIG. 13 is a diagram of one fourth of the view from infinity of the totally dispersed light for a diamond of 33.5° crown angle, 4.0° pavilion angle, and table 0.55 with 64 girdle facets, a 3% girdle thickness, a 50% star facet length, 75% lower-girdle length and a 0.5% culet size.
Figure 14:
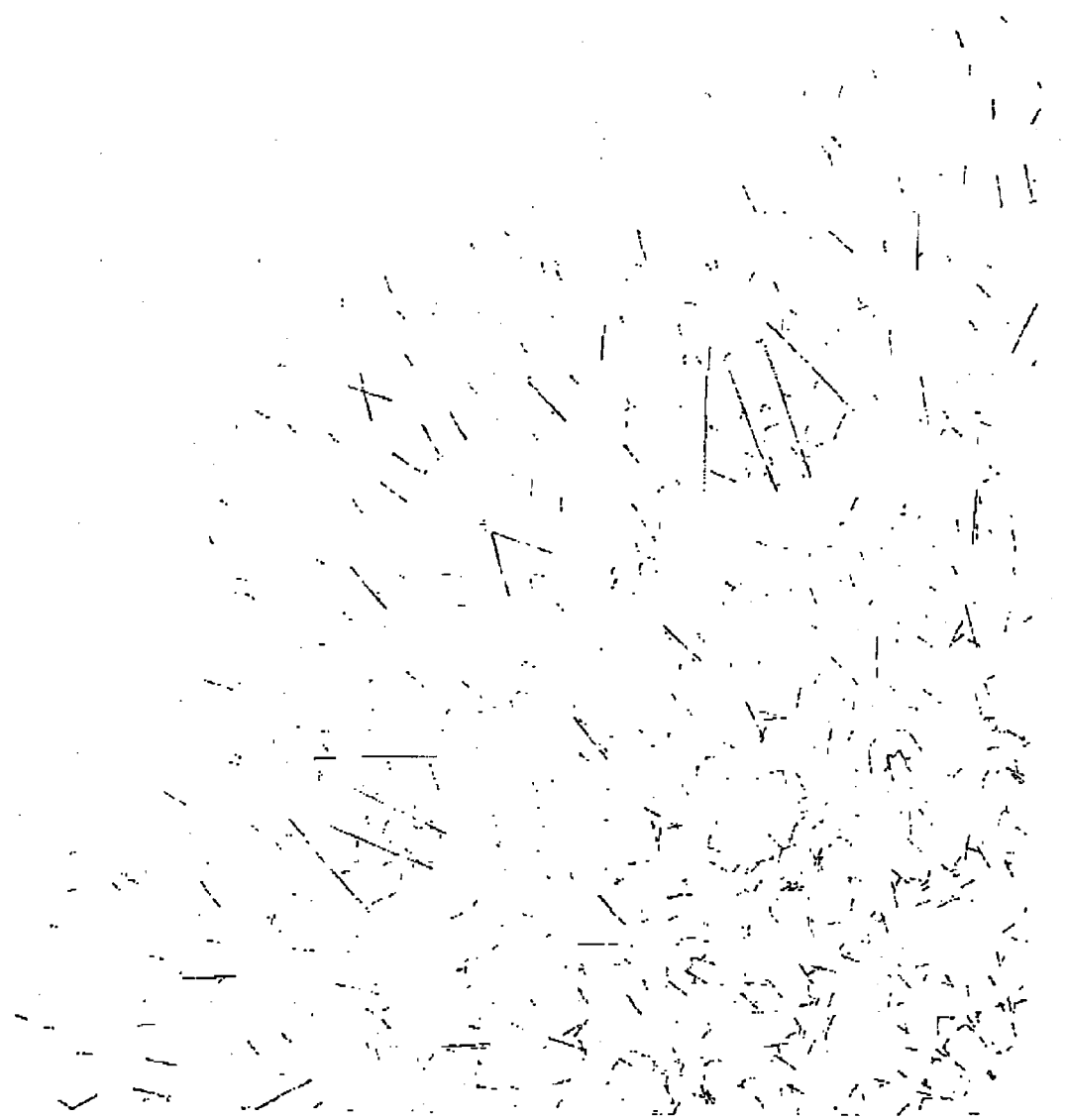
FIG. 14 is a diagram of one fourth of the view from infinity of the totally dispersed light for a diamond of 31.5° crown angle, 38.70 pavilion angle, and table 0.52 with 64 girdle facets, a 3% girdle thickness, a 50% star facet length, 75% lower-girdle length and a 0.5% culet size.
Figure 15:
FIG. 15 is a diagram of one fourth of the view from infinity of the totally dispersed light for a diamond of 31.5° crown angle, 40.7° pavilion angle, and table 0.52 with 64 girdle facets, a 3% girdle thickness, a 50% star facet length, 75% lower-girdle length and a 0.5% culet size.
Figure 16:
FIG. 16 is a diagram of one fourth of the view from infinity of the totally dispersed light for a diamond of 31.5° crown angle, 42.7° pavilion angle, and table 0.52 with 64 girdle facets, a 3% girdle thickness, a 50% star facet length, 75% lower-girdle length and a 0.5% culet size.
Figure 17:
FIG. 17 is a diagram of one fourth of the view from infinity of the totally dispersed light for a diamond 33.5° crown angle, 40.7° pavilion angle, and table 0.60 with 64 girdle facets, a 3% girdle thickness, a 50% star facet length, 75% lower-girdle length and a 0.5% culet size.
Figure 18:
FIG. 18 is a diagram of one fourth of the view from infinity of the totally dispersed light for a diamond 35.3° crown angle, 40.0° pavilion angle, and table 0.56 with 64 girdle facets, a 3% girdle thickness, a 50% star facet length, 75% lower-girdle length and a 0.5% culet size.
Figure 19:
FIG. 19 is a diagram of one fourth of the view from infinity of the totally dispersed light for a diamond 28.5° crown angle, 40.7° pavilion angle, and table 0.53 with 64 girdle facets, a 3% girdle thickness, a 50% star facet length, 75% lower-girdle length and a 0.5% culet size.
Figure 20:
FIG. 20 is a diagram of one fourth of the view from infinity of the totally dispersed light for a diamond 28.5°, crown angle, 40.7°pavilion angle, and table 0.63 with 64 girdle facets, a 3% girdle thickness, a 50% star facet length, 75% lower-girdle length and a 0.5% culet size.
Figure 21:
FIG. 21 is a diagram of one fourth of the view from infinity of the totally dispersed light for a diamond 34.5°, crown angle, 40.7° pavilion angle, and table 0.57 with 64 girdle facets, a 3% girdle thickness, a 50% star facet length, 75% lower-girdle length and a 0.5% culet size.
Figure 22:
FIG. 22 is a diagram of one fourth of the view from infinity of the totally dispersed light for a diamond 32.7°, crown angle, 41.5° pavilion angle, and table 0.60 with 64 girdle facets, a 3% girdle thickness, a 50% star facet length, 75% lower-girdle length and a 0.5% culet size.

Somewhat similar topography is observed in FIGS. 5 and 6, contour maps of DCLR over crown angle and table size for the medium and high thresholds, respectively. At the medium threshold, crown angles of 37–38° yield significantly lower DCLR at all table sizes greater than 0.57, while crown angles of 32–33° yield moderate DCLR across the whole range of table sizes. There is a large ridge across shallow crown angles and all table sizes in the plot for the highest threshold, although for this data the numerical range of the values is quite small.

FIGS. 10A to 10F, 11A to 10F and 12A to 10F give the data for variation in DCLR as pavilion angle and table size each vary, for the three thresholds. The topography becomes much more complex as the threshold is lowered, and the range of values increases considerably. For the lowest threshold, there is a small ridge at a pavilion angle of 38.25 and table sizes of 0.56 and lower, and for all three thresholds there is a long ridge at a pavilion angle of 39.25 across the whole range of tablet sizes. This ridge appears more broad at the highest threshold, covering pavilion angles from 39–41°.

Importantly, the FIGS. 4A to 4C through 6A to 6C and 10A to 10F through 12A to 12F demonstrate that preferred "fire" proportions based on the disclosed proportion parameters can serve as guides or even ranges in a cut grade determination.

Using DCLR Data to Evaluate Fire. The DCLR surfaces that we have calculated as a function of crown angle, pavilion angle, and table size are irregular, with a number of maxima, rather than a single maximum. These multiple "peaks" are a principal result of this extensive three-dimensional analysis. Their existence supports a position taken by many in the trade in terms of dispersed light return, or fire there are many combinations of parameters that yield equally "attractive" round brilliant diamonds. Neither the internal dispersion of light nor the interaction between the proportion parameters is taken into account by existing cut-grading systems, which are based on Tolkowsky's analysis at a single refractive index, and examine each parameter separately.

It is especially important to note that some proportion combinations that yield high DCLR values are separated from one another and not contiguous, as shown in the cross-sections of the DCLR surfaces. Thus, for some given values of two proportions, changes in the third proportion in a single direction may first worsen DCLR and then improve it again. This variation in DCLR with different proportion combinations makes the characterization of the "best" diamonds, in terms of fire, a great challenge. Even for one simple shape—the round brilliant cut—and variation of only two proportion parameters at a time, the surfaces of constant DCLR are highly complex.

The specific proportion combinations that produce high DCLR values have a variety of implications for diamond manufacturing. Because many combinations of proportions yield similarly high DCLR values, diamonds can be cut to many choices of proportions with the same fire, which suggests a better utilization of rough.

Evaluation of "Superior" Proportions Suggested by Earlier Researchers. A gem diamond should display an optimal combination of brilliance, fire, and pleasing scintillation. Many previous researchers have suggested proportions that they claim achieve this aim, but none but Dodson have proposed a measure or test to compare the fire or scintillation of two sets of proportions. A list of "superior" proportions and their calculated WLR value was presented in Hemphill et al. (1998), and we have calculated DCLR for some of these proportions as well. The highest value we found was for Suzuki's Dispersion Design (1970), with a DCLR (at the lowest threshold, as are all the values presented in this discussion) of 6.94; however this set of proportions had yielded a very low WLR value of 0.205. Eppler's Ideal Type II proportions yielded a relatively high DCLR value of 5.04, and a moderately high WLR value of 0.281. Dodson's suggestion for most fiery was bright (WLR=0.287) but yielded a low DCLR of 4.32. Dodson's proportions for the most sparkliness yielded a higher DCLR of 5.18, but with a low WLR value of 0.247. His suggestion for brightest had yielded an average WLR of 0.277, and a moderately low DCLR of 4.51.

Work by Shannon and Wilson, as described in the trade press (Shor, 1998), presented four sets of proportions that they claimed gave "outstanding performance" in terms of their appearance. Previously we calculated typical to moderately high WLR values for these proportions, and now we find moderate to moderately high DCLR values of 4.63–5.24. In comparison, Rosch's suggestion for "Ideal" proportions had yielded a low WLR value of 0.251, but produce high DCLR of 5.94. Tolkowsky's suggested proportions, including the knife-edge girdle and a 53% table, yield a DCLR value of 5.58, but this value is reduced significantly as the table size or girdle thickness increases.

Implications for Existing Cut-Grading Systems. Our results disagree with the concepts on which the proportion grading systems currently in use by various laboratories appear to be based. In particular, they do not support the idea that all deviations from a narrow range of crown angles and table sizes should be given a lower grade. Nor do they support the premises that crown proportions matter most for fire.

Arguments that have been made for downgrading diamonds with lower crown angles or larger tables on the basis that they do not yield enough fire are in part refuted by the results of our modeling. Our results show more agreement with those of Dodson (1979): that fire depends on combinations of proportions, rather than on any single parameter. However, our results are at a finer scale than those of Dodson, and show distinct trends for certain ranges of proportion combinations.

REFERENCES

Astric B., Merigoux H., Zecchini P. (1992) Etude de la variation de l'aspect de pierres taillèes à l'aide d'images de synthèse. La Gemmologia, Vol. 17, No. 1, pp. 7–31.

Bergheimer H. (1938) Die Schleifrichtungen auf den Facetten des Diamantbrillanten. Neues Jahrbuch für Mineralogie, Geo-logie, und Paläontologie, Vol. 75A, pp. 145–158.

Caspi A. (1997) Modern diamond cutting and polishing. Gems & Gemology, Vol. 33, No. 2, pp. 102–121.

Connellan M., Pozzibon L. (1984) The Australian ideal design for round brilliants. Australian Gemmologist, Vol. 24, pp. 219–226, 243–246.

Crowningshield G. R., Moses T. (1997) Diamond: Damaged from wear. Gem Trade Lab Notes, Gems & Gemology, Vol. 33, No. 1, pp. 55–56.

Dodson J. S. (1979) The statistical brilliance, sparkliness and fire of the round brilliant-cut diamond. Diamond Research, pp. 13–17.

Elbe M. G. (1972) Erstaunliche Schmuckeffekte an Brillanten. Zeitschrift der Deutschen Gemmologischen Gesellschaft, Vol. 21, No. 4, pp. 189–212.

Eppler W. F. (1933) Der Diamant und seine Bearbeitung. Wilhelm Diebener GmbH, Leipzig, 68 pp.

Eppler W. F. (1938) Die Ideal-Schleifformen durchsichtiger Edelsteine. Zentralblatt fër Mineralogie, Geologie, und Paläontologie, Abteilung A, pp. 1–5.

Eppler W. F. (1939) Die Brillanz durchsichtiger Edelsteine. Fortschritte der Mineralogie, Kristallographie, und Petrographie, Vol. 23, pp. 1–40.

Eppler W. F. (1940) Beitrag zum Brillanzproblem II. Zentralblatt für Mineralogie, Geologie, und Paläontologie, Abteilung A, No. 4, pp. 93–96.

Eppler W. F. (1973) Praktische Gemmologie. Rühle-Diebener Verlag KG, Stuttgart.

Eppler W. F., Klüppelberg E. (1940) Die praktische Brillantschliff des Diamanten. Neues Jahrbuch für Mineralogie, Geologie, und Paläontologie, Vol. 75A, pp. 135–144.

Eulitz W. R. (1972) Die rechnerische Ermittlung der optimalen Brillanz der Brillanten. Zeitschrift der Deutschen Gemmologischen Gesellschaft, Vol. 21, No. 1, pp. 13–43.

Federman D. (1997) Make believe. Modern Jeweler, Vol. 96, No. 9, pp. 23–38, 62–63.

Foley J. D., Ed. (1996) Computer Graphics: Principles and Practice, 2nd ed. in C, Addison-Wesley Publishing Co., Reading, Mass.

GIA Diamond Dictionary, 3rd ed. (1993) Gemological Institute of America, Santa Monica, Calif., 275 pp.

GIA Jeweler's Manual (1989) Gemological Institute of America, Santa Monica, Calif., 327 pp.

Gilbertson A. (1998) Letting Light Speak for Itself. Diamond Profile Inc., Portland, Oreg., 14 pp. plus appendices.

Gilbertson A., Walters C. (1997) The measure of beauty. Rapaport Diamond Report, Vol. 20, No. 6, pp. 43, 45–46.

Johnsen A. (1926) Form und Brillanz der Brillanten. Sitzungsberichte der Preussischen Akademie der Wissenschaften, Physikalische-Mathematische Klasse, Vol. 23, pp. 322–330.

Lawrence J. (1998) Just how much sparkle? Diamond International, No. 53, pp. 77–78.

Maier W. (1936) Brillanz geschliffener Edelsteine. Neues Jahrbuch fër Mineralogie, Geologie, und Paläontologie, Vol. 71A, pp. 458–491.

Maier W. (1938) Vollreflexbrillanten. Zentralblatt für Mineralogie, Geologie, und Paläontologie, Abteilung A, pp. 230–239.

Nassau K. (1983) The Physics and Chemistry of Color—The Fifteen Causes of Color. Wiley Interscience, New York, 454 pp.

Nestlebaum K. (1996) New AGS lab stakes its claim on cut grade. Rapaport Diamond Report, Vol. 19, No. 17, pp. 15–17.

Nestlebaum K. (1997) Ideals: Worth the trouble to those who cut them. Rapaport Diamond Report, Vol. 20, No. 10, pp. 18–19.

Papadopoulos A. D, Anastassakis E. (1991) Optical properties of diamond. Physical Review B, Vol. 43, No. 6, pp. 5090–5097.

Rösch S. (1926) Die Brillanzwirkung des geschliffenen Diamanten. Deutsche Goldschmiede Zeitung, No. 5, pp. 45–48; No. 7, pp. 65–67; No. 9, pp. 88–90.

Rösch S. (1927) Beitrag zum Brillanzproblem IV. Zeitschrift fuir Kristallographie, Vol. 65, pp. 46–68.

Scandinavian Diamond Nomenclature Committee (1979) The Scandinavian Diamond Nomenclature and Grading Standards: Official Version. Trade Associations of Jewellers in Denmark, Finland, Norway and Sweden, 50 pp.

Schlossmacher K. (1969) Edelsteine und Perlen, 5 Auflage. E. Schweizerbart'sche Verlagsbuchhandlung, Stuttgart.

Shor R. (1993) Cutting grades-new complications. Jewelers'Circular-Keystone, Vol. 164, No. 4, pp. 52–55.

Shor R. (1997) Consumers who care about cut: A small, but growing group. Jewelers'Circular-Keystone, Vol. 168, No. 6, pp. 124–126.

Shor R. (1998) Computer engineers create proportion grade program. New York Diamonds, Vol. 44, pp. 26–28.

Stoephasius A. (1931) Lässt sich das Gewicht gefasster Brillanten sicher berechnen? Deutsche Goldschmiede Zeitung, No. 45, pp. 470–474.

Suzuki S. (1970) A new design for brilliance plus dispersion. Australian Gemmologist, Vol. 10, No. 10, pp. 13–24.

Tillander H. (1966) Six centuries of diamond design. Gems & Gemology, Vol. 12, No. 3, pp. 77–95.

Tillander H. (1995) Diamond Cuts in Historical Jewellery: 1381–1910. Art Books International, London.

Tognoni C. (1990) An automatic procedure for computing the optimum cut proportions of gems. La Gemmologia, Vol. 25, No. 3–4, pp. 23–32.

Tolkowsky G. (1996) Cutting the Edges. Diamond Insight, Vol. 9, No. 2, pp. 9–10.

Tolkowsky M. (1919) Diamond Design: A Study of the Reflection and Refraction of Light in a Diamond. E. & F. N. Spon, London.

Wade F. B. (1916) Diamonds: A Study of the Factors that Govern Their Value. G. P. Putnam's Sons, New York.

Ware, J. W. (1936) New diamond cuts break more easily. Gems & Gemology, Vol. 2, No. 4, p. 68.

Watermeyer B. (1991) Diamond Cutting, 4th ed. Preskor Doornfontein, Johannesburg, 406 pp.

Wright, W. D. (1969) The Measurement of Colour, 4th ed., Van Nostrand, New York.

Box A:

DETAILED DESCRIPTION OF ONE DIAMOND MODEL EMBODIMENT

In one embodiment, the diamond model describes a faceted diamond as a convex polyhedron, a three-dimensional object with a surface that is bounded by flat planes and straight edges, with no indentations or clefts. The model requires that all surfaces be faceted, including the girdle, and currently excludes consideration of indented naturals or cavities. To date, we have focused our calculations on the round brilliant cut because of its dominant position in the market, but this model can be used for nearly any fully faceted shape. Our modeled round brilliant has mathematically perfect symmetry; all facets are perfectly shaped, pointed, and aligned. Also, all facet junctions are modeled with the same sharpness and depth.

Because our modeled round brilliant has perfect eight-fold symmetry, only eight numbers (proportion parameters) are required to specify the convex polyhedron that describes its shape (FIG. A-1). (Modeling other shapes or including asymmetries requires additional parameters). We defined these eight parameters as:

| | |
|---|---|
| Crown angle | Angle (in degrees) between the bezel facets and the girdle plane |
| Pavilion angle | Angle (in degrees) between the pavilion mains and the girdle plane |
| Table size | Table width (as percent of girdle diameter) |
| Culet size | Culet width (as percent of girdle diameter) |
| Star facet length | The ratio of the length of the star facets to the distance between the table edge and girdle edge, as projected into the table plane |
| Lower-girdle length | The ratio of the length of the lower-girdle facets to the distance between the center of the culet and girdle edge, as projected into the table plane |
| Girdle thickness | Measured between bezel and pavilion main facets (the thick part of the girdle) and expressed as a percentage of girdle diameter. This differs from the typical use of the term girdle thickness (see, e.g., GIA Diamond Dictionary, 1993) |
| Girdle facets | Total number of girdle facets |

Other proportions, such as the crown height, pavilion depth, and total depth (expressed as percentages of the girdle diameter) can be directly calculated from these eight parameters, using these formulas:

Crown height=1 2(100–table size)×tan(crown angle)

Pavilion depth=1 2(100–culet size)×tan(pavilion angle)

Total depth=(Crown height+pavilion depth+girdle thickness)

For the results in this application, the diamond simulated in our calculations (called a "virtual" diamond) has no inclusions, is perfectly polished, and is completely colorless. It has a polished girdle, not a bruted one, so that the girdle facets refract light rays in the same way that other facets do. The virtual diamond is non-dimensionalized, i.e. it has relative proportions but no absolute size—that is, no specific carat weight. The principles governing the way light moves through a colorless diamond do not vary with size, but some aspects of viewing a diamond do depend on its absolute size. A specific diameter can be applied to the virtual diamond for such purposes, or for others such as the application of a color or fluorescence spectrum.

We then chose modelled light sources to illuminate our virtual diamond. Results for brilliance (Hemphill et al., 1998) used a diffuse hemisphere of even, white light (D65 daylight illumination) shining on the crown. That illumination condition averages over the many different ambient light conditions in which diamonds are seen and worn, from the basic trading view of a diamond face-up in a tray next to large north-facing windows, to the common consumer experience of seeing a diamond worn outdoors or in a well-lit room. Such diffuse illumination emphasizes the return of white light, but it is a poor lighting condition for examining other fire and scintillation. These aspects are maximized by directed light, such as direct sunlight or the small halogen track lights common in many jewelry stores. Directed light is readily modeled as one or more point light sources at infinity or as a collimated finite-size spot at some other distance. For calculation of DCLR we used a D65 point light source at infinite distance, centered over the table. This illumination condition samples the maximum extent to which the round brilliant can disperse light. This same modelled lighting can be used to examine some aspects of scintillation, although other aspects, particularly dynamic ones, will require more than one lighting position.

Next we examined mathematically how millions of rays of light from the source interact with the transparent, three-dimensional, colorless, fully faceted round brilliant specified by our choice of proportion parameters. Diamond is a dispersive material; the refractive index is different for different wavelengths of light. Since the angle of refraction depends on the refractive index, white light entering the virtual diamond is spread (dispersed) into rays of different colors, and each of these variously colored rays takes a slightly different path through the stone. We used Sellmeier's formula (see Nassau, 1983 [p. 211]; or, for a more thorough explanation, see Papadopoulos and Anastassakis, 1991) to incorporate this dispersion into the model. With this formula, we obtained the correct refractive index for each of the different colored rays (taken at 1 nm intervals from 360 to 830 min), so that each ray could be traced (followed) along its correct path as it moved through the stone. Very few rays follow simple paths with only a few internal reflections; most follow complex three-dimensional paths (FIG. A-2).

Each time a ray strikes a facet, some combination of reflection and refraction takes place, depending on the angle between the ray and the facet, the refractive index at the wavelength of the ray, and the polarization state of the ray. Although the rays from our point light source are initially unpolarized, a light ray becomes partly polarized each time it bounces off a facet. The degree and direction of polarization affect how much of the ray is internally reflected, rather than refracted out the next time it intersects a facet. (For example, about 18% of a light ray approaching a diamond facet from the inside at an angle of 5° from the perpendicular is reflected, regardless of the polarization. But at an incidence of 70°, rays with polarization parallel to the plane of incidence are completely lost from the stone, while 55% of a ray polarized perpendicular to the plane of incidence is reflected back into the stone). The model traces each ray until 99.95% of its incident energy has exited the diamond. The end result of this ray tracing can be an image of the virtual diamond (seen from a short distance or from infinity) or the value of a metric for that stone.

Although modifications and changes may be suggested by those skilled in the art, it is the intention of the inventors to embody within the patent warranted hereon all changes and modifications as reasonable and properly come within the scope of their contribution to the art.

What is claimed is:

1. A method for providing a cut grade for a gemstone, comprising:
   illuminating a gemstone model with a point light source at infinite distance;
   refracting light elements, originating from the point light source, through the gemstone model;
   evaluating the fire of the gemstone model using a metric, wherein evaluating the fire includes a calculation of the Dispersed Color Light Return.

2. The method of claim 1 wherein DCLR is the sum (over wavelength of the light elements) of the sum (over the number of light elements) of the differential area of each light element that exceeds a power density threshold criterion, multiplied by an exit angle weighting factor.

3. The method of claim 2, wherein said exit angle weighting factor is the square of the cosine of the exit angle.

4. The method of claim 2, wherein the sum of the number of light elements only counts refracted light elements that exceed a power density threshold based on the color sensitivity of the human eye.

5. The method of claim 2 wherein the power density threshold cutoff for a refracted light element is approximately 1% of the power density of the brightest light element.

6. The method of claim 2 wherein the power density threshold cutoff for a refracted light element is approximately 0.1% of the power density of the brightest light element.

7. The method of claim 2 wherein the power density threshold cutoff for a refracted light element is approximately 0.01% of the power density of the brightest light element.

8. A method for providing a cut grade for a gemstone comprising:
   analyzing cut proportions of a gemstone;
   comparing the cut proportions of the gemstone with a list of proportion grades that depend, at least in part, on a calculation of dispersed color light return;
   providing a grade for the gemstone based on said list of proportion grades, wherein the grade is a fire grade.

* * * * *